US 10,568,929 B2

United States Patent
Antalis et al.

(10) Patent No.: US 10,568,929 B2
(45) Date of Patent: Feb. 25, 2020

(54) ENGINEERED ANTHRAX PROTECTIVE ANTIGEN PROTEINS FOR CANCER THERAPY

(71) Applicant: UNIVERSITY OF MARYLAND, BALTIMORE, Baltimore, MD (US)

(72) Inventors: Toni Antalis, Potomac, MD (US); Erik Martin, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 15/747,255

(22) PCT Filed: Aug. 19, 2016

(86) PCT No.: PCT/US2016/047854
§ 371 (c)(1),
(2) Date: Jan. 24, 2018

(87) PCT Pub. No.: WO2017/031455
PCT Pub. Date: Feb. 23, 2017

(65) Prior Publication Data
US 2018/0214511 A1    Aug. 2, 2018

Related U.S. Application Data

(60) Provisional application No. 62/207,100, filed on Aug. 19, 2015.

(51) Int. Cl.
| | |
|---|---|
| C07K 14/32 | (2006.01) |
| C07K 16/38 | (2006.01) |
| A61K 38/48 | (2006.01) |
| A61K 38/51 | (2006.01) |
| A61K 38/16 | (2006.01) |
| A61P 35/04 | (2006.01) |
| A61P 35/00 | (2006.01) |
| A61K 38/00 | (2006.01) |

(52) U.S. Cl.
CPC ........ *A61K 38/164* (2013.01); *A61K 38/4886* (2013.01); *A61K 38/51* (2013.01); *A61P 35/00* (2018.01); *A61P 35/04* (2018.01); *C07K 14/32* (2013.01); *C07K 16/38* (2013.01); *A61K 38/00* (2013.01); *C07K 2319/50* (2013.01)

(58) Field of Classification Search
None
See application file for complete search history.

(56) References Cited

U.S. PATENT DOCUMENTS

2005/0255083 A1   11/2005  Leppla et al.

FOREIGN PATENT DOCUMENTS

| WO | 01/21656 | 3/2001 |
|---|---|---|
| WO | 2005/090393 | 9/2005 |
| WO | 2008/076939 | 6/2008 |
| WO | 2014/031861 | 2/2014 |

OTHER PUBLICATIONS

Liu et al., "Capillary Morphogenesis Protein-2 is the Major Receptor Mediating Lethality of Anthrax Toxin in vivo", PNAS, 106(30): 12424-12429 (2009).
Su et al., "Systematic Urokinase-Activated Anthrax Toxin Therapy Produces Regressions of Subcutaneous Human Non-Small Cell Lung Tumor in Athymic Nude Mice", Cancer Res, 67(7): 3329-3336 (2007).
Wigelsworth et al., "Binding Stoichiometry and Kinetics of the Interaction of a Human Anthrax Toxin Receptor, CMG2, with Protective Antigen", Journal of Biological Chemistry, 279(22): 23349-23356 (2004).
Liu et al., "Potent antitumor activity of a urokinase-activated engineered anthrax toxin", PNAS, 100(2): 657-662 (2003).
Alfano et al., "Cytotoxicity of the matrix metalloproteinase-activated anthrax lethal toxin is dependent on gelatinase expression and B-RAF status in human melanoma cells", Molecular Cancer Therapy, 7(5): 1218-1226 (2008).
Venkatraman et al., "A Sequence and Structure Based Method to Predict Putative Substrates, Functions and Regulatory Networks of Endo Proteases", PLoS One, 4(5): e5700 (2009).
Martin et al., "Targeting the membrane-anchored serine protease testisin with a novel engineered anthrax toxin prodrug to kill tumor cells and reduce tumor burden", Oncotarget, 6(32): 33534-33553 (2015).
International Search Report and Written Opinion of the International Searching Authority, dated Jan. 24, 2017 in corresponding International Patent Application No. PCT/US16/47854.
Extended European Search Report dated Jan. 3, 2019 in corresponding European Application No. 16837927.9.
Liu et al., "Targeting of tumor cells by cell surface urokinase plasminogen activator-dependent anthrax toxin", Journal of Biological Chemistry 276(21):17976-17984 (2001).

*Primary Examiner* — Padmavathi Baskar
(74) *Attorney, Agent, or Firm* — Wenderoth, Lind & Ponack, L.L.P.

(57) ABSTRACT

Engineered anthrax protective antigen (PrAg) proteins are provided wherein the native furin activation site is replaced by the activation site of a membrane-anchored serine protease. These engineered PrAg proteins retain the ability to bind to cell surface PrAg receptors and be proteolytically activated. The proteins also retain the ability to form membrane pores. These engineered PrAg proteins can be used in methods of inducing pore formation in a cell, methods of inducing translocation of a selected compound or co-factor into a cell, and methods of treating disease, such as cancer, in a subject.

5 Claims, 17 Drawing Sheets
Specification includes a Sequence Listing.

| | PrAg-WT | PrAg-PAS | PrAg-PCIS | PrAg-TAS | PrAg-UAS |
|---|---|---|---|---|---|
| | testisin / matriptase / hepsin / prostasin | testisin / matriptase / hepsin / prostasin | testisin / matriptase / hepsin / prostasin | testisin / matriptase / hepsin / prostasin | testisin / matriptase / hepsin / prostasin |

-83 kDa
-63 kDa

B

| | PrAg-PCIS | PrAg-PAS | PrAg-UAS | PrAg-WT |
|---|---|---|---|---|
| | 0 15 30 60 150 | 0 15 30 60 150 | 0 15 30 60 150 | 0 15 30 60 150 minutes |
| testisin | | | | | -83 kDa / -63 kDa |
| matriptase | | | | | -83 kDa / -63 kDa |
| hepsin | | | | | -83 kDa / -63 kDa |
| furin | | | | | -83 kDa / -63 kDa |

Average abdominal photon count 8.0 E+06
6.0 E+06
4.0 E+06
2.0 E+06
0.0 E+00

1   4   9
Day of treatment

□ vehicle
□ PrAg-PAS toxin
▨ PrAg-U7 toxin
■ PrAg-IC toxin

B   Day 1 of treatment   Day 9 of treatment vehicle

PrAg-PAS toxin

PrAg-U7 toxin

PrAg-IC toxin

A

B

ENGINEERED ANTHRAX PROTECTIVE ANTIGEN PROTEINS FOR CANCER THERAPY

This invention was made with government support under Grant Numbers HL118390 and HL084387 awarded by the National Institutes of Health. The government has certain rights in the invention.

SEQUENCE LISTING

A sequence listing in electronic (ASCII text file) format is filed with this application and incorporated herein by reference. The name of the ASCII text file is "2016_0823A_ST25.txt"; the file was created on Aug. 18, 2016; the size of the file is 74 KB.

BACKGROUND

Proteolytic enzymes and their regulatory networks, including cofactors, activators, and endogenous inhibitors, are frequently dysregulated in tumors resulting in increased protease activities that contribute to progression of disease [1]. Manipulation of tumor-promoting proteases is a promising approach for the development of anti-tumor therapies [2,3]. While the targeting of proteases has been approached in several ways [4], prodrug-like protease substrates that are activated by overexpressed proteases are an extremely efficient approach to increasing selectivity and efficacy while reducing off-target effects [5].

Anthrax toxins requiring proteolytic activation have been engineered to target proteases overexpressed by tumor cells. Anthrax toxin is a cytotoxic pore-forming exotoxin secreted by *Bacillus anthracis*. Consisting of protective antigen (PrAg), lethal factor (LF), and edema factor (EF), the toxin (the combination of PrAg and LF and/or EF) causes cellular cytotoxicity through a well-characterized mechanism [6], whereas individually these proteins are non-toxic. PrAg binds to either of two cell-surface receptors, tumor endothelial marker-8 (TEM8, ANTXR1) and capillary morphogenesis gene-2 (CMG2, ANTXR2), of which CMG2 is expressed on nearly all cell types. PrAg (83 kDa) bound to its cell-surface receptor(s) is proteolytically cleaved and activated by the protease furin (FURIN) or furin-like proprotein convertases in an exposed flexible loop to generate an active C-terminal 63-kDa PrAg fragment.

The newly-generated 63-kDa PrAg fragment remains receptor bound and catalyzes the formation of a PrAg/receptor oligomer that presents docking sites to enable up to four molecules of LF or EF to bind and translocate into the cytosol of a cell, through an endosomal PrAg-formed pore, wherein LF/EF then have potent cytotoxic effects [7].

As a highly efficient protease-activated delivery system, PrAg can be engineered to deliver different payloads or co-factors into the cytosol [8-14]. Additionally, PrAg can be engineered to be activated specifically by proteases other than furin. Since furin is ubiquitously expressed, it is advantageous to narrow the cellular protease targets for drug delivery applications. Alteration of the furin protease cleavage site within PrAg to amino acid sequences recognized by either urokinase-type plasminogen activator (uPA, PLAU) [15], matrix metalloproteinase 2 (MMP2), or matrix metalloproteinase 9 (MMP9) [16] renders PrAg a potent uPA- or MMP2/9-activated prodrug that has been shown to target tumors that overexpress any of these proteases [17-26]. An engineered anthrax inter-complementing toxin has also been created that requires combined activation by these protease systems for function and killing of tumor cells [20,27].

While such uPA- or MMP2/9-activated prodrugs may be useful in some applications, in addition to their roles in tumor biology the uPA and MMP protease systems play leading roles in immune regulation and physiological tissue remodeling [4,28]. Therefore, while these engineered anthrax protein prodrugs are effective when used to target tumors in vivo, it is possible that paracrine association of the tumor-secreted proteases with other non-tumor cells in or near the tumor microenvironment could contribute to off-target effects of these toxin systems. Therefore, the use of existing protease-activated PrAg proteins is limited, and the development of new, targeted proteins is needed. The present application is directed to this and to other important goals.

BRIEF SUMMARY

The present application provides engineered, protease-activated, anthrax toxin protective antigen (PrAg) protein prodrugs and means for their use in therapeutic applications. These engineered PrAg protein prodrugs can be targeted to cells overexpressing membrane-anchored serine proteases, such as many tumor cells. As demonstrated herein, the targeting of such cells allows for a highly-specific, more efficient approach to directed cell targeting and tumor cell killing by engineered anthrax toxins than previous in systems.

In a first aspect, the invention generally relates to engineered PrAg proteins comprising the native anthrax PrAg amino acid sequence where the furin activation site is replaced by a membrane-anchored serine protease activation site. These activation sites are domains within the proteins that are recognized and cleaved by membrane-anchored serine proteases. The engineered PrAg proteins of the invention thus comprise the amino acid sequence set forth in SEQ ID NO:1, wherein the furin activation site is replaced by a membrane-anchored serine protease activation site. The PrAg protein includes an N-terminal, 29 amino acid signal peptide. Therefore, the engineered PrAg proteins of the invention also comprise the amino acid sequence set forth in SEQ ID NO:1, wherein the furin activation site is replaced by a membrane-anchored serine protease activation site and wherein the N-terminal, 29 amino acid signal peptide has been removed. The engineered PrAg proteins of the invention further include sequence variants having 90% or more sequence identity over their entire length to one of the engineered PrAg proteins defined herein. In aspects of the invention, the furin activation site consists of amino acids 193-200 of SEQ ID NO:1. In other aspects, the membrane-anchored serine protease activation site is one or more sequences selected from the group consisting of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6).

In a second aspect, the invention generally relates to methods of inducing pore formation in a cell using the engineered PrAg proteins described herein. The invention thus includes methods of inducing pore formation in a cell comprising contacting a cell with an engineered PrAg protein, as defined herein, under conditions promoting pore formation in the cell, where the cell expresses an anthrax toxin PrAg protein receptor and a membrane-anchored serine protease. The receptor may be, but is not limited to, one or more of tumor endothelial marker-8 (TEM8) and capillary morphogenesis gene-2 (CMG2). The membrane-anchored serine protease may be, but is not limited to, one or more of testisin, hepsin, and matriptase.

In a third aspect, the invention generally relates to methods of inducing translocation of a selected co-factor into a cell using the engineered PrAg proteins described herein. The invention thus includes methods of inducing translocation of a selected co-factor into a cell, comprising (a) contacting a cell with an engineered PrAg protein, as defined herein, under conditions promoting pore formation in the cell, wherein the cell expresses an anthrax toxin PrAg protein receptor and a membrane-anchored serine protease, and (b) contacting the cell of (a) with a selected co-factor under conditions promoting translocation of the selected co-factor into the cell. The receptor may be, but is not limited to, one or more of tumor endothelial marker-8 (TEM8) and capillary morphogenesis gene-2 (CMG2). The membrane-anchored serine protease may be, but is not limited to, one or more of testisin, hepsin, and matriptase. The selected co-factor may be, but is not limited to, a diagnostic co-factor or a therapeutic co-factor. Exemplary diagnostic co-factors include, but are not limited to, imaging agents and markers. The therapeutic co-factor may be a cytotoxic co-factor or a non-cytotoxic co-factor. Exemplary cytotoxic co-factors include, but are not limited to, one or more of LF, EF, FP59, and LFn-CdtB. Exemplary non-cytotoxic co-factors include, but are not limited to, one or more of peptide fragments, antigens and epitopes, growth factors, enzymes, and antibodies and functional fragments or mimetics thereof.

In a fourth aspect, the invention generally relates to methods of treating cancer in a subject using the engineered PrAg proteins described herein and a co-factor that has a cytotoxic effect on a cancer cell. The invention thus includes methods of treating cancer in a subject comprising administering a pharmaceutical formulation to a subject in need thereof wherein the pharmaceutical formulation comprises a therapeutically effective amount of an engineered PrAg protein, as defined herein, and a therapeutically effective amount of a therapeutic co-factor, thereby treating cancer in the subject. The method may also be practiced by administering the engineered PrAg protein and the therapeutic co-factor in separate formulations. The invention thus includes methods of treating cancer in a subject comprising (a) administering a first pharmaceutical formulation to a subject in need thereof wherein the first pharmaceutical formulation comprises a therapeutically effective amount of an engineered PrAg protein, as defined herein, and (b) administering a second pharmaceutical formulation to the subject of (a) wherein the second pharmaceutical formulation comprises a therapeutically effective amount of a therapeutic co-factor, thereby treating cancer in the subject. In particular aspects, the cancer is a cancer characterized by cells expressing an anthrax toxin PrAg protein receptor and a membrane-anchored serine protease. The receptor may be, but is not limited to, one or more of tumor endothelial marker-8 (TEM8) and capillary morphogenesis gene-2 (CMG2). The membrane-anchored serine protease may be, but is not limited to, one or more of testisin, hepsin, and matriptase. The cancer may be, but is not limited to ovarian cancer, cervical cancer, pancreatic cancer, prostate cancer, and lung cancer. The cancer may be a benign cancer or a metastatic cancer. The cancer may be one that is resistant to other treatments, such as a cancer resistant to radiotherapy or chemotherapy. The therapeutic co-factor may be, but is not limited to, one or more cytotoxic co-factors selected from the group consisting of EF, LF, FP59 and LFn-CdtB.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1A) Protein C inhibitor (PCI) is a serine protease inhibitor (serpin) and is a testisin substrate. Testisin cleaves PCI at the P1-P1' sequence of the serpin reactive center loop (RCL). Recombinant testisin was incubated with recombinant PCI for various times up to 30 minutes. Individual reactions were stopped at indicated times and immunoblotted using anti-PCI antibody. The blot is representative of two independent experiments. FIG. 1B) PrAg-PCIS is resistant to furin cleavage, while PrAg-PCIS and PrAg-WT are susceptible to proteolytic cleavage by various recombinant serine proteases. PrAg-PCIS and PrAg-WT were incubated with furin, the recombinant catalytic domains of membrane-anchored serine proteases, or recombinant pericellular serine proteases for 2.5 hours. Reactions were immunoblotted using anti-PrAg antibody to detect PrAg activation cleavage. The blot is representative of two independent experiments. FIG. 1C) PrAg-PCIS and PrAg-WT toxin-induced human tumor cell cytotoxicity. The indicated tumor cell lines were incubated with PrAg proteins (0-500 ng/mL) and FP59 (50 ng/mL) for 48 hours, after which cell viability was evaluated by MTT assay. Values are the means calculated from two independent experiments performed in triplicate. FIG. 1D and FIG. 1E) PrAg-PCIS toxin targets serine proteases on the surface of ES-2 and DU-145 tumor cells. Cells were pre-incubated in the presence of a final concentration of 100 µM aprotinin for 30 minutes prior to treatment with the indicated concentrations of PrAg-PCIS and FP59 (50 ng/mL) for 2 hours. Cell viability was evaluated by MTT assay 48 hours later. Values are the means calculated from two independent experiments performed in triplicate. *p<0.05.

FIG. 2A) PrAg-PCIS and FIG. 2B) PrAg-WT were incubated with recombinant testisin, hepsin, matriptase, or furin for various intervals up to 2.5 hours. Reactions were immunoblotted using anti-PrAg antibody. Each blot is representative of at least two independent experiments.

FIG. 3A) Recombinant hepsin or FIG. 3B) recombinant matriptase were incubated with PCI, at room temperature prior to immunoblotting with anti-PCI, anti-hepsin, or anti-matriptase antibodies. Full-length PCI, cleaved PCI, and serpin-protease inhibitory complexes are as indicated. Each blot is representative of at least two independent experiments. FIG. 3C) PCI inhibits hepsin and matriptase catalytic activities. Recombinant testisin, hepsin, and matriptase were incubated with the peptide substrate, Suc-AAPR-pNA, in the presence or absence of PCI and the changes in absorbance monitored over the course of 15 minutes. The data is representative of at least two independent experiments.

FIG. 4A) Cell-expressed testisin increases processing of PrAg-PCIS. HEK293T cells stably expressing wild-type testisin (HEK/GPI-testisin) or vector alone (HEK/

PrAg-PCIS 5 µg, and PrAg-PCIS 10 µg.

(FIG. 8A-FIG. 8D) Histology and immunohistochemical analyses performed on serial sections of tumors resected from mice treated with PrAg-PCIS 1 PrAg-PCIS 5 µg, and PrAg-PCIS 10 µg or vehicle alone (PBS/LF). Representative serial sections and high power magnified fields are shown to reveal gross tumor morphology, overall tumor staining, and regions of necrosis and proliferation, as well as antibody specificity. (FIG. 8E-FIG. 8H) Composite images compiled from each stained section were analyzed to determine % tumor viability (H&E), % tumor cell proliferation (Ki67), % apoptosis (activated caspase-3), and % vessel density (CD31), as indicated. Tumors: n=4 vehicle; n=3 PrAg-PCIS 1 µg; n=2 PrAg-PCIS 5 µg; n=3 PrAg-PCIS 10 µg. *p<0.05.

FIGS. 9A-9B. The mutant PrAg proteins are cleaved by testisin, hepsin, and matriptase. Testisin, hepsin, and matriptase cleave the mutant PrAg and wild-type PrAg proteins to activated forms. FIG. 9A) The mutant or wild-type PrAg proteins (1 µM) were incubated with recombinant testisin, hepsin, matriptase, or prostasin (50 nM) for 2.5 hours. Reactions were immunoblotted using anti-PrAg antibody. Each blot is representative of at least two independent experiments. FIG. 9B) The mutant or wild-type PrAg proteins (1 µM) were incubated with recombinant testisin, hepsin, matriptase, or furin (50 nM) for various intervals of time up to 2.5 hours. Reactions were immunoblotted using anti-PrAg antibody to detect the inactive full-length PrAg (83 kDa) and the cleaved PrAg activated form (63 kDa). Each blot is representative of at least two independent experiments and contains 15 µg of each PrAg protein loaded into each lane of the gel (after dilution).

FIGS. 12A-12C. PrAg-PAS toxin requires proteolytic activation to reduce ovarian tumor burden. Cohorts of mice (n=5) bearing ES-2-luc i.p. xenograft tumors received four treatments of vehicle (PBS), PrAg-PAS toxin (15 µg PrAg-PAS and 5 µg LF), PrAg-U7 toxin (15 µg PrAg-U7 and 5 µg LF), or PrAg-IC toxin (combination of 7.5 µg PrAg-U2 and 7.5 µg PrAg-L1, and 5µg LF). Tumor burden, as measured by luciferase activity levels, was monitored using the IVIS system. Quantitative data are represented as mean values with their respective standard errors (+/−SEM). p<0.01, *p<0.001. FIG. 12A) Ovarian tumor burden was reduced, as indicated by reduced average luciferase activity levels, in mice treated with PrAg-PAS toxin as well as PrAg-IC toxin, but not in mice treated with PrAg-U7 toxin, relative to vehicle treated mice. FIG. 12B) Images representing the peak luciferase activity levels in the individual mice treated with vehicle, PrAg-PAS toxin, PrAg-U7 toxin, or PrAg-IC toxin. Images show the increase in tumor burden over time in mice treated with vehicle or PrAg-U7 toxin, and a decrease in tumor burden in mice treated with PrAg-PAS toxin or PrAg-IC toxin. FIG. 12C) Upon performing necropsies, ES-2-luc tumor burden was widespread in mice treated with vehicle or PrAg-U7 toxin. Tumor cells covered the diaphragm, and multiple tumor nodules were dispersed throughout the abdominal cavity with tumor nodules occasionally observed attached to organs. Substantially fewer tumor cells and tumor nodules were observed in mice treated with PrAg-PAS toxin or PrAg-IC toxin. Arrows indicate areas of substantial tumor burden or tumor nodules. Necropsy images are representative of the tumor burden in each of the respective cohorts of mice.

FIG. 13A) Cleavage of the peptide by the different tumor cell lines when ~90% confluent. FIG. 13B) Cleavage of the peptide by the different tumor cell lines when ~40% confluent. Fluorescence values were normalized to average cell number for each tumor cell line after the assay was complete.

FIG. 15G) Ovarian tumor cell line expression of hepsin, matriptase, anthrax toxin receptors, and serine protease inhibitors. Ovarian tumor cell lines that were treated with the PrAg toxins were subject to qPCR analysis to measure their relative expression levels of hepsin, matriptase, anthrax toxin receptors (ANTXR1, ANTXR2), and serine protease inhibitors (HAI-1, HAI-2, PCI). mRNA expression was normalized to beta-actin or GAPDH, and expressed relative to the mRNA levels detected in ES-2 cells. Quantitative data are represented as mean values with their respective standard errors (+/−SEM).

DETAILED DESCRIPTION

I. Definitions

Figures 1A, 1B, 1C, 1D, 1E:
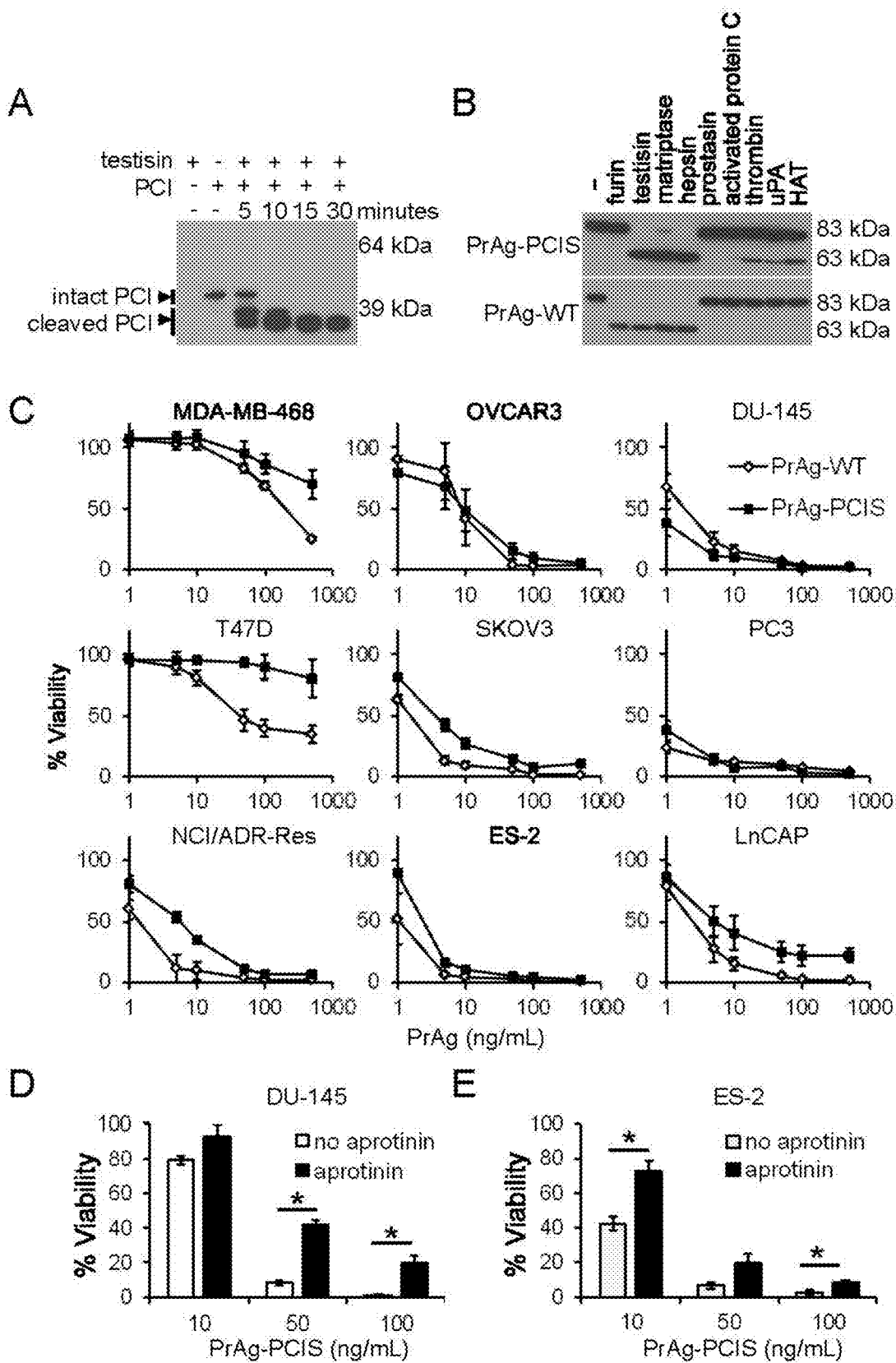
FIGS. 1A-1E. The engineered PrAg-PCIS targets tumor cell serine proteases.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein, when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Membrane-anchored serine proteases are a unique group of trypsin-like serine proteases that are tethered to the surface of a cell via transmembrane domains or GPI-anchors [29,30]. Overexpressed in ovarian and other tumors, with pro-tumorigenic properties, they are attractive targets for anti-tumor therapies [31-48]. However, developed drugs targeted against the catalytic mechanism of serine proteases can lead to unacceptable non-target effects due to involvement of the proteases in many essential physiological processes [92]. Presented herein is an alternative approach for exploiting these enzymes in the therapeutic targeting of tumors and the treatment of cancer.

Rather that blocking the activity of membrane-anchored serine proteases expressed by tumor cells, this alternative approach relies on the protease activity of the enzymes. By taking advantage of the fact that protease overexpression is associated with many types of tumor cells, the prodrugs disclosed herein can have a targeted effect on tumor cells. In particular, the prodrugs disclosed herein are activated by these overexpressed membrane-anchored serine proteases. Because activation is largely centered on tumor cells, cytotoxic co-factors that function in concert with the prodrugs can be functionally restricted to the tumor cell microenvironment.

These prodrugs are engineered, anthrax toxin protective antigen (PrAg) proteins. Anthrax toxin is a cytotoxic pore-forming exotoxin secreted by *Bacillus anthracis*. Consisting of protective antigen (PrAg), lethal factor (LF), and edema factor (EF), the toxin (the combination of PrAg and LF and/or EF) causes cellular cytotoxicity. PrAg binds to either of two cell-surface receptors, tumor endothelial marker-8 (TEM8,ANTXR1) and capillary morphogenesis gene-2 (CMG2, ANTXR2), of which CMG2 is expressed on nearly all cell types. Upon receptor binding, PrAg (83 kDa) is proteolytically cleaved and activated by the protease furin (FURIN) or furin-like proprotein convertases at an activation site to generate an active C-terminal 63-kDa PrAg fragment. The newly-generated 63-kDa fragment remains receptor bound and catalyzes the formation of a PrAg/receptor oligomer that presents docking sites to enable up to four molecules of LF or EF to bind and translocate into the cytosol of a cell, through an endosomal PrAg-formed pore, wherein LF/EF then have potent cytotoxic effects [7].

The engineered PrAg proteins disclosed herein are based on the native anthrax PrAg polypeptide, but possess an activation site recognized and cleaved by a selected membrane-anchored serine protease in place of the furin activation site. Upon application to tumor cells in vitro or administration to a subject having cancer, activation of the engineered PrAg proteins via the membrane-anchored serine protease activation site is concentrated on tumor cells overexpressing the corresponding serine protease. The engineered PrAg proteins disclosed herein are bound by the same cell surface receptors as native anthrax PrAg (e.g., TEM8 and CMG2). Furthermore, once activated the engineered PrAg proteins exhibit the same activity as the native protein which includes catalyzing the formation of a PrAg/receptor oligomer pores in the cell that allow translocation of co-factors, such as LF and EF, into the cell. Thus, when a cytotoxic co-factor such as LF or EF is administered with the engineered PrAg proteins, the co-factors can induce a tumoricidal effect.

Engineered PrAg Proteins

The present invention is thus directed, in part, to engineered PrAg proteins. The engineered PrAg proteins of the invention include polypeptides comprising the amino acid sequence of the native anthrax PrAg protein, wherein the furin activation site has been replaced by a membrane-anchored serine protease activation site. The engineered PrAg proteins of the invention also include sequence variants of these polypeptides.

The full-length *Bacillus anthracis* anthrax toxin PrAg protein is shown in SEQ ID NO:1 and it comprises 764 amino acids. The polypeptide undergoes processing to release a 29 amino acid, N-terminal signal peptide. The resulting mature PrAg protein comprises 735 amino acids and it is set forth in SEQ ID NO:3. The polynucleotide sequence encoding the full-length anthrax toxin PrAg protein is shown in SEQ ID NO:2.

The engineered PrAg proteins of the invention include both full-length and mature anthrax PrAg proteins in which the furin activation site has been replaced by a membrane-anchored serine protease activation site. For sake of convenience, the engineered PrAg proteins of the invention are generally defined herein based on the sequence of the full-length anthrax PrAg protein set forth in SEQ ID NO:1. It should be understood that the engineered PrAg proteins of the invention also include mature forms where the 29 amino acid signal sequence has been removed.

The furin activation site (i.e., the domain within native PrAg recognized and cleaved by the protease furin) may be generally defined as encompassing amino acids 189-204 of SEQ ID NO:1 (i.e., the full-length PrAg protein). The furin activation site may also be defined as encompassing amino acids 189-203, amino acids 189-202, amino acids 189-201, amino acids 189-200, amino acids 190-204, amino acids 190-203, amino acids 190-202, amino acids 190-201, amino acids 190-200, amino acids 191-204, amino acids 191-203, amino acids 191-202, amino acids 191-201, amino acids 191-200, amino acids 192-204, amino acids 192-203, amino acids 192-202, amino acids 192-201, amino acids 192-200, amino acids 193-204, amino acids 193-203, amino acids 193-202, amino acids 193-201, or amino acids 193-200 of SEQ ID NO:1. In a particular aspect of the invention, the furin activation site is RKKRSTSA (SEQ ID NO:56), which consists of amino acids 193-200 of SEQ ID NO:1 (amino acids 164-171 of SEQ ID NO:3).

The identity of the membrane-anchored serine protease activation site that is used in place of the furin activation site in the engineered PrAg proteins is limited only in that it confers on the engineered PrAg protein the ability to be cleaved and activated by a selected membrane-anchored serine protease. Suitable membrane-anchored serine protease activation sites include activation sites recognized by one or more of the membrane-anchored serine proteases shown in Table 1. In particular aspects, the engineered PrAg proteins of the invention contain protease activation sites recognized by one or more of testisin, hepsin, and matriptase.

TABLE 1

|   | Name | Other names | GENE NAME |
|---|---|---|---|
| 1 | Testisin | PRSS21, TESP, TEST1, ESP-1, tryptase 4 | PRSS21 |
| 2 | Prostasin | CAP1, PRSS8 | PRSS8 |
| 3 | Tryptase Gamma 1 | TMT/TPSG1, PRSS31 | TPSG1 |
| 4 | HAT | Human airway tryptase | TMPRSS11D |
| 5 | DESC1 | TMPRSS11E | TMPRSS11E |
| 6 | HATL1 | HAT-like 1, TMPRSS11A, DESC3 | TMPRSS11A |
| 7 | HATL4 | TMPRSS11F | TMPRSS11F |
| 8 | HATL5 | TMPRSS11B | TMPRSS11B |
| 9 | Hepsin | TMPRSS1 | HPN |
| 10 | TMPRSS2 | Epitheliasin | TMPRSS2 |
| 11 | TMPRSS3 | TADG-12, TMPRSS3, ECHOS1 | TMPRSS3 |
| 12 | TMPRSS4 | MT-SP2, CAP2 | TMPRSS4 |
| 13 | TMPRSS5 | Spinesin | TMPRSS5 |
| 14 | TMPRSS13 | MSPL | TMPRSS13 |
| 15 | Matriptase | MT-SP1, CAP3, TADG-15, PRSS14, ST14, SNC19, epithin (mouse) | ST14 |
| 16 | Matriptase 2 | TMPRSS6 | TMPRSS6 |
| 17 | Matriptase 3 | TMPRSS7 | TMPRSS7 |
| 18 | Polyserase-1 | TMPRSS9 | TMPRSS9 |
| 19 | Enteropeptidase | PRSS7, Enterokinase | PRSS7 |
| 20 | Corin | LRP4, ATC2, TMPRSS10 | CORIN |

Non-limiting examples of membrane-anchored serine protease activation sites that may be used in the engineered PrAg proteins of the invention include those shown in Table 2. This table provides two groups of activation sites, i.e., domains that are recognized and cleaved by one or more of the membrane-anchored serine protease of Table 1. The first group encompasses the activation sites defined as SEQ ID NOs:4-27. These are zymogen activation sites of various proteases. The second group encompasses the activation sites defined as SEQ ID NOs:28-47. These are reactive center loop sites of various serpins. In particular aspects, the membrane-anchored serine protease activation sites are one or more of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6).

TABLE 2

Membrane-anchored Serine Protease Activation Sites

| Sequence | SEQ ID NO: | Name | Abbreviation | SERPIN # |
|---|---|---|---|---|
| IPSRIVGG | 4 | Testisin Zymogen Activation | TAS | |
| PQARITGG | 5 | Prostasin Zymogen Activation | PAS | |
| PRFRITGG | 6 | uPA Zymogen Activation | UAS | |
| DDDKIVGG | 7 | Trypsin Zymogen Activation | TrAS | |
| ITSRIVGG | 8 | Testisin Zymogen Activation | TAS-2 | |
| AGGRIVG | 9 | Tryptase Gamma 1 Zymogen Activation | TrGAS | |
| RQARVVG | 10 | Matriptase Zymogen Activation | MAS | |

TABLE 2-continued

Membrane-anchored Serine Protease Activation Sites

| Sequence | SEQ ID NO: | Name | Abbreviation | SERPIN # |
|---|---|---|---|---|
| PSSRIVGG | 11 | Matriptase 2 Zymogen Activation | M2AS | |
| ALHRIIGG | 12 | Matriptase 3 Zymogen Activation | M3AS | |
| ITPKIVGG | 13 | Enteropeptidase Zymogen Activation | EAS | |
| MNKRILGG | 14 | Corin Zymogen Activation | CAS | |
| PVDRIVGG | 15 | Hepsin Zymogen Activation | HAS | |
| RQSRIVGG | 16 | TMPRSS2 Zymogen Activation | T2AS | |
| YSSRIVGG | 17 | TMPRSS3 Zymogen Activation | T3AS | |
| KTPRVVGV | 18 | TMPRSS4 Zymogen Activation | T4AS | |
| LASRIVGG | 19 | Spinesin Zymogen Activation | SAS | |
| MAGRIVGG | 20 | TMPRSS9 Zymogen Activation | T9AS | |
| QSLRIVGG | 21 | DESC1 Zymogen Activation | D1AS | |
| NVNRASG | 22 | DESC3 Zymogen Activation | D3AS | |
| TGNKIVNG | 23 | TMPRSS11B Zymogen Activation | T11bAS | |
| SEQRILGG | 24 | HAT (TMPRSS11D) Zymogen Activation | T11dAS | |
| MTGRIVGG | 25 | MSPL (TMPRSS13) Zymogen Activation | T13AS | |
| STQRIVQG | 26 | TMPRSS11F Zymogen Activation | T11fAS | |
| QGSRIIGG | 27 | TMPRSS12 Zymogen Activation | T12AS | |
| FTFRSARL | 28 | Protein C Inhibitor (PCI) | PCIS | SERPINA5 |
| AIPMSIPP | 29 | $\alpha_1$-Antitrypsin | $\alpha$1AT | SERPINA1 |
| EKAWSKYQ | 30 | $\alpha_1$-Antitrypsin Related Protein | ATRP | SERPINA2 |
| ITLLSALV | 31 | $\alpha_1$-Antichymotrypsin | ACT | SERPINA3 |
| IKFFSAQT | 32 | Kallistatin | KST | SERPINA4 |
| LNLTSKPI | 33 | Corticosteroid Binding Globulin | CBG | SERPINA6 |
| LSDQPENT | 34 | Thyroxin Binding Globulin | TBG | SERPINA7 |
| NKPEVLEV | 35 | Angiotensiogen | AGT | SERPINA8 |
| FIVRSKDG | 36 | Centerin | CTN | SERPINA9 |
| ITAYSMPP | 37 | Protein Z-dependent Protease Inhibitor | ZPI | SERPINA10 |
| LTPMETPL | 38 | Vaspin | VPN | SERPINA12 |
| MTGRTGHG | 39 | Plasminogen Activator Inhibitor-2 | PAI2 | SERPINB2 |
| ILQHKDEL | 40 | Maspin | MPN | SERPINB5 |
| IAGRSLNP | 41 | Antithrombin | ATH | SERPINC1 |
| FMPLSTQV | 42 | Heparin Cofactor II | HC2 | SERPIND1 |
| VSARMAPE | 43 | Plasminogen Activator Inhibitor-1 | PAI1 | SERPINE1 |
| LIARSSPP | 44 | Protease Nexin 1 | PN1 | SERPINE2 |
| AMSRMSLS | 45 | $\alpha_2$-Antiplasmin | $\alpha$1AP | SERPINF2 |
| AISRMAVL | 46 | Neuroserpin | NSP | SERPINI1 |
| IPVIMSLA | 47 | Myoepithelium-derived Serine Proteinase Inhibitor | MEPI | SERPINI2 |

In particular aspects, the engineered PrAg proteins of the invention comprise the amino acid sequence set forth in SEQ ID NO:1 where the furin activation site consisting of amino acids 193-200 is replaced by a membrane-anchored serine protease activation site selected from the group consisting of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6), and sequence variants thereof having about 90% or more sequence identity over their entire length. The engineered PrAg proteins of the invention also can be defined a comprising the amino acid sequences set forth in: SEQ ID NO:54 (PrAg-PCIS), SEQ ID NO:48 (PrAg-TAS), SEQ ID NO:50 (PrAg-PAS), and SEQ ID NO:52 (PrAg-UAS).

As indicated above, the invention includes engineered PrAg proteins may defined based on the mature form of the PrAg protein lacking the signal peptide and thus the engineered PrAg proteins of the invention also comprise the amino acid sequence set forth in SEQ ID NO:3 where the furin activation site consisting of amino acids 164-171 is replaced by a membrane-anchored serine protease activation site selected from the group consisting of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6), and sequence variants thereof having about 90% or more sequence identity over their entire length.

Sequence Variants

Because amino acid alterations to the native anthrax PrAg protein and the protease activation sites can often be made without adversely affecting the activity of the engineered PrAg proteins, sequence variants of the engineered PrAg proteins disclosed herein are encompassed within the scope of the invention. The sequence variants have amino acid alterations that include individual amino acid insertions, substitutions (e.g., conservative and/or non-conservative), and/or additions, and combinations thereof.

Examples of conservative substitutions within different groups of amino acids include basic amino acid substitutions (i.e. between arginine, lysine and histidine), acidic amino acid substitutions (i.e. between glutamic acid and aspartic acid), polar amino acid substitutions (i.e. between glutamine and asparagine), hydrophobic amino acid substitutions (i.e. between leucine, isoleucine and valine), aromatic amino acid substitutions (i.e. between phenylalanine, tryptophan and tyrosine), and small amino acid substitutions (i.e. between glycine, alanine, serine, threonine and methionine). Amino acid substitutions known to have minimal effect on specific activity are described [93]. Specific exchanges included within the scope of the invention include Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to conservative and non-conservative substitutions, amino acids used in the preparation of the sequence variants include non-standard amino acids (e.g., 4-hydroxyproline, 6-N-methyl lysine, 2-aminoisobutyric acid, isovaline, and alpha-methyl serine) and unnatural amino acids, e.g., those that have been modified after protein synthesis, and/or have a chemical structure in their side chain(s) different from that of the standard amino acids. Unnatural amino acids include, but are not limited to, pipecolic acid, thiazolidine carboxylic acid, dehydroproline, 3- and 4-methylproline, and 3,3-dimethylproline.

Amino acids essential for the structure and activity of the engineered PrAg proteins can be identified according to procedures known in the art, such as site-directed mutagenesis or alanine-scanning mutagenesis [94,95]. Sites of protein interaction can also be determined by physical analysis of structure, as determined by such techniques as nuclear magnetic resonance, crystallography, electron diffraction, or photoaffinity labeling, in conjunction with mutation of putative contact site amino acids [96-98]. The identities of essential amino acids can also be inferred from analysis of identities with polypeptides which are related to an engineered PrAg protein disclosed herein.

Alternations to the amino acid sequence of the engineered PrAg proteins may be accomplished via a number of techniques known to those of ordinary skill in the art, including mutagenesis, recombination, and/or shuffling, which can be confirm be sequencing or other relevant screening procedures [99-102].

The invention thus includes sequence variants of the engineered PrAg proteins disclosed herein, wherein the sequence variants have about 90% or more sequence identity over the entire length of the amino acid sequence to the amino acid sequence of an engineered PrAg protein defined herein. The sequence variants also include those having about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity over the entire length of the amino acid sequence to the amino acid sequence of an engineered PrAg protein defined herein.

The amino acid alterations in the sequence variants can be limited to particular regions or domains of the proteins. For example, amino acid alterations may be excluded from the protease activation sites. Alternatively, or in addition, the amino acid alterations may be excluded from PrAg receptor binding sites.

The sequence variants of the invention retain the ability to be activated by a membrane-anchored serine protease, to be bound by an anthrax PrAg receptor, and to form PrAg/receptor oligomer pores in a cell for translocation of co-factors.

Co-Factors

The engineered PrAg proteins of the invention, by themselves, are generally benign and non-toxic. But because these proteins form pores in a cell, they can be used to introduce one or more selected co-factors (as they work in conjunction with the engineered PrAg proteins) into a cell. Co-factors can be selected based on the activity they have once inside of a cell. Relevant activities include, but are not limited to, signaling, therapeutic, and cytotoxic activities on or in the cell. It will be apparent that the co-factors can be used in diagnostic and therapeutic applications, thus the co-factors can be diagnostics and therapeutics.

As shown in the Examples provided herein, engineered PrAg proteins can bind to tumor cells where they are activated by the enzymatic activities of cell surface serine proteases. When introduced to the cells along with a cytotoxic co-factor, the combination induces death of the tumor cells. Moreover, the Examples demonstrate the several different engineered PrAg proteins have been established that are cytotoxic in combination with the co-factors to multiple human tumors, including pancreatic, prostate, lung and ovarian tumors, that each express variable levels of membrane-anchored serine proteases.

The co-factors that may be used in combination with the engineered PrAg proteins of the invention are only limited in that (i) they can enter a cell through a PrAg-induced cellular pore, and (ii) they have a desired effect once in the cytosol.

The co-factors may be, but are not limited to, diagnostic co-factors and therapeutic co-factor.

Exemplary diagnostic co-factors include, but are not limited to, imaging agents such as green fluorescent protein and AlexaFluor545, as well as markers, such as a radioactive moiety. The diagnostic co-factors are commonly administered in the context of a chaperone. For example, a non-cytotoxic variant of LF or EF can be conjugated to or labeled with an imaging agent or a marker.

The therapeutic co-factor may be a cytotoxic co-factor or a non-cytotoxic co-factor. Cytotoxic co-factors induce cell death, while non-cytotoxic co-factors alter a selected characteristic or activity of a cell, but do not kill the cell. The cytotoxic co-factors include those that are cytotoxic only after entry into the cytosol, as well as cytotoxic co-factors that are active both outside and inside of a cell.

Cytotoxic co-factors include, but are not limited to, anthrax toxin lethal factor (LF) and anthrax toxin edema factor (EF). Cytotoxic co-factors also include fusions between LF or EF, or functional portions thereof, and agents that have a lethal effect in or on a cell. As an example, FP59 is a fusion protein consisting of LF and the catalytic domain of *Pseudomonas aeruginosa* exotoxin A that has a cytotoxic effect when translocated into a cell via a PrAg/receptor oligomeric pore [67]. Additional fusions between LF or EF, or functional portions thereof, include fusions with one or more of diphtheria toxin A chain (DTA), Shiga toxin A chain (STA), listeriolysin O epitope (LLO), ricin toxin A chain, cytolethal distending toxin B (CdtB), doxorubicin, monomethyl auristatin F, docetaxel, and antibodies and functional fragments or mimetics thereof. See also the listing provided in Table 1 of [103]. Functional portions of LF include the N-terminal domain of LF (LFn, comprising amino acids 1-254 of the protein). In one example, a fusion between LFn and CdtB (LFn-CdtB) may be used.

Non-cytotoxic co-factors include, but are not limited to, beta-lactamase, dihydrofolate reductase (DHFR), gp120, peptide fragments, antigens and epitopes, growth factors, enzymes, and antibodies and functional fragments or mimetics thereof. Such non-cytotoxic co-factors will commonly be fused to a functional fragment of EF or LF, such as LFn.

Methods of Inducing Pore Formation

It will be apparent to the skilled artisan that the engineered PrAg proteins of the invention can be used in a number of different applications. In one aspect, the engineered PrAg proteins are used to induce formation of pores in a cell, both in vitro as well as in vivo. Alteration of the furin activation site of the native anthrax PrAg protein does not affect the ability of the engineered PrAg proteins disclosed herein to oligomerize with PrAg receptors on the cell surface and to form membrane pores.

The invention thus includes methods for inducing pore formation in a cell. The methods comprise contacting a cell with an engineered PrAg protein, as defined herein, under conditions promoting pore formation in the cell. It will be apparent that cells on which the method may be practiced are cells that express an anthrax toxin PrAg protein receptor as well as a membrane-anchored serine protease that acts on the activation site engineered into the PrAg protein. When the method is practiced in vitro, conditions promoting pore formation in a cell include culture conditions typical associated with the cell culture in vitro, such as 5% $CO_2$, 95% relative humidity, and 37° C.

Suitable PrAg protein receptors include, but are not limited to, tumor endothelial marker-8 (TEM8) and capillary morphogenesis gene-2 (CMG2).

Suitable membrane-anchored serine proteases include, but are not limited to, one or more of testisin, hepsin, and matriptase.

Methods of Inducing Translocation of Selected Factors

In another aspect, the engineered PrAg proteins are used to induce translocation of co-factors into a cell. The engineered PrAg proteins disclosed herein retain the ability to oligomerize with PrAg receptors on the cell surface and to form membrane pores. They also retain the ability to induce translocation of selected co-factors into the cytosol of the cell.

The invention thus includes methods for inducing translocation of a selected co-factor into a cell, comprising contacting a cell with an engineered PrAg protein, as defined herein, under conditions promoting pore formation in the cell, and then contacting the cell with a selected co-factor under conditions promoting translocation of the selected co-factor into the cell. These methods can be practiced on cells in vitro and in vivo. It will be apparent that cells on which the method may be practiced are cells that express an anthrax toxin PrAg protein receptor as well as a membrane-anchored serine protease that acts on the activation site engineered into the PrAg protein. When the method is practiced in vitro, conditions promoting pore formation in a cell include culture conditions typical associated with the cell culture in vitro, such as 5% $CO_2$, 95% relative humidity, and 37° C.

Suitable PrAg protein receptors include, but are not limited to, tumor endothelial marker-8 (TEM8) and capillary morphogenesis gene-2 (CMG2).

Suitable membrane-anchored serine proteases include, but are not limited to, one or more of testisin, hepsin, and matriptase.

The selected co-factor is only limited in that it can enter a cell through PrAg-induced cellular pores and have a desired effect therein. The selected co-factor may be, but is not limited to, a diagnostic co-factor or a therapeutic co-factor. Exemplary diagnostic co-factors include, but are not limited to, imaging agents and markers. The therapeutic co-factor may be a cytotoxic co-factor or a non-cytotoxic co-factor. Exemplary cytotoxic co-factors include, but are not limited to, one or more of LF, EF, FP59, and LFn-CdtB. Exemplary non-cytotoxic co-factors include, but are not limited to, one or more of peptide fragments, antigens and epitopes, growth factors, enzymes, and antibodies and functional fragments or mimetics thereof.

Methods of Treatment

In a further aspect, the engineered PrAg proteins are used in therapeutic applications, e.g., methods of medical treatment of a subject. Because tumor cells have been shown to overexpress certain membrane-anchored serine proteases, the engineered PrAg proteins of the invention are especially suitable for methods of treating diseases such as cancer in a subject. However, it should be apparent that the engineered PrAg proteins may also be used in methods of treating other disease and conditions.

The methods of treatment encompassed by the invention include methods where the engineered PrAg proteins alone are administered to a subject. The methods of treatment encompassed by the invention also include methods where the engineered PrAg proteins and a one or more selected co-factors are administered to a subject. When also administered to the subject, the identity of the co-factors will depend on the particular disease or condition to be treated.

Methods of treatment encompassed by the invention include those that comprise administering a therapeutically effective amount of an engineered PrAg protein, as defined herein, to a subject in need thereof, such as a subject having a disease or condition, including, but not limited to, cancer. Methods of treatment encompassed by the invention also include those that comprise administering a therapeutically effective amount of an engineered PrAg protein, as defined herein, and a therapeutically effective amount of therapeutic co-factor, as defined herein, to a subject in need thereof.

In a specific aspect, the invention includes methods of treating cancer in a subject comprising administering a therapeutically effective amount of an engineered PrAg protein, as defined herein, to a subject in need thereof. The invention also includes methods of treating cancer in a subject comprising administering a therapeutically effective amount of an engineered PrAg protein, as defined herein, and a therapeutically effective amount of therapeutic co-factor, as defined herein, to a subject in need thereof.

In the methods of treatment disclosed herein, the engineered PrAg protein may be in a pharmaceutical formulation. The therapeutic co-factor may also be in a pharmaceutical formulation. In some aspects, the engineered PrAg protein and the therapeutic co-factor are in the same pharmaceutical formulation.

In another selected aspect, the invention includes methods of treating cancer in a subject comprising (a) administering a first pharmaceutical formulation to a subject in need thereof wherein the first pharmaceutical formulation comprises a therapeutically effective amount of an engineered PrAg protein, as defined herein, and (b) administering a second pharmaceutical formulation to the subject wherein the second pharmaceutical formulation comprises a therapeutically effective amount of a therapeutic co-factor, as defined herein, thereby treating cancer in the subject.

In a further selected aspect, the invention includes methods of treating cancer in a subject comprising administering a pharmaceutical formulation to a subject in need thereof comprising a therapeutically effective amount of an engineered PrAg protein, as defined herein, and a therapeutically effective amount of a therapeutic co-factor, as defined herein, thereby treating cancer in the subject.

The order in which the engineered PrAg proteins and therapeutic co-factors are administered to a subject when the methods of the invention are practiced may vary. Thus, a portion or all of the engineered PrAg protein may be administered to the subject before administration of the therapeutic co-factor begins. Similarly, a portion or all of the therapeutic co-factor may be administered to the subject before administration of the engineered PrAg protein begins. Alternatively, the engineered PrAg proteins and therapeutic co-factors may be co-administered, such as when administered in the same pharmaceutical formulation.

It will be apparent that the cancer on which the methods may be practiced will comprise cells that express an anthrax toxin PrAg protein receptor as well as a membrane-anchored serine protease that acts on the activation site engineered into the PrAg protein.

PrAg protein receptors expressed by the cancer cells include, but are not limited to, tumor endothelial marker-8 (TEM8) and capillary morphogenesis gene-2 (CMG2).

Suitable membrane-anchored serine proteases expressed by the cancer cells include, but are not limited to, one or more of testisin, hepsin, and matriptase.

The methods of treatment provided herein can be used to treat a variety of diseases and conditions, limited only in that cells associated with the disease or condition, such as tumor cells of a cancer, express an anthrax toxin PrAg protein receptor as well as a membrane-anchored serine protease that acts on the activation site engineered into the PrAg protein. Exemplary diseases and conditions include, but are not limited to, cancer and tumors. Cancers that may be treated using the methods of the invention potential include all cancers, including all solid tumors, as well as hematological tumors, such as leukemia. In one aspect, the cancers that may be treated using the methods of the invention include, but are not limited to, ovarian cancer, cervical cancer, pancreatic cancer, prostate cancer, and lung cancer. The cancer may be a benign cancer or a metastatic cancer. The cancer may be one that is resistant to other treatments, such as a cancer resistant to radiotherapy or chemotherapy.

The therapeutic co-factor that may be used in these methods is limited only in that it can enter a cell through PrAg-induced cellular pores and have a therapeutic effect on the cell. The therapeutic co-factor may be a cytotoxic co-factor or a non-cytotoxic co-factor. Exemplary cytotoxic co-factors include, but are not limited to, one or more of LF, EF, FP59, and LFn-CdtB. Exemplary non-cytotoxic co-factors include, but are not limited to, one or more of peptide fragments, antigens and epitopes, growth factors, enzymes, and antibodies and functional fragments or mimetics thereof.

Polynucleotide, Expression Vectors, Host Cells and Method of Making

The present invention also includes polynucleotide sequences encoding each of the engineered PrAg proteins defined herein, as well as complementary strands thereof. These polynucleotide sequences include those encoding engineered PrAg proteins having the amino acid sequence set forth in SEQ ID NO:1 where the furin activation site consisting of amino acids 193-200 is replaced by a membrane-anchored serine protease activation site selected from the group consisting of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6), and sequence variants thereof having about 90% or more sequence identity over their entire length.

These polynucleotide sequences also include those encoding engineered PrAg proteins having the amino acid sequence set forth in SEQ ID NO:3 where the furin activation site consisting of amino acids 164-171 is replaced by a membrane-anchored serine protease activation site selected from the group consisting of FTFRSARL (PCIS; SEQ ID NO:28), IPSRIVGG (TAS; SEQ ID NO:4), PQARITGG (PAS; SEQ ID NO:5), and PRFRITGG (UAS; SEQ ID NO:6), and sequence variants thereof having about 90% or more sequence identity over their entire length.

Specific polynucleotide sequences encompassed within the scope of the invention include the polynucleotide sequences set forth in SEQ ID NO:55 (PrAg-PCIS), SEQ ID NO:49 (PrAg-TAS), SEQ ID NO:51 (PrAg-PAS), and SEQ ID NO:53 (PrAg-UAS).

The skilled artisan will understand that due to the redundancy of the genetic code, there are a large number of different polynucleotide sequences that may encode the engineered PrAg proteins of the invention. The invention therefore also encompasses sequence variants of the polynucleotides defined herein. These sequence variants include those having about 90% or more sequence identity over their entire length, as well as those having about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity over their entire length.

The invention also includes cloning and expression vectors comprising the polynucleotide sequences defined herein, as well as host cells comprising the cloning and expression vectors. Suitable expression vectors include, e.g., *E. coli Bacillus* expression plasmids pYS5 or pYS5-PA33. Suitable host cells include, e.g., *B. anthracis* strains, attenuated *B. anthracis* strains, *B. anthracis* strain BH460.

The invention further includes methods of producing the engineered PrAg proteins defined herein, comprising culturing the host cells under conditions promoting expression of the engineered PrAg proteins encoded by the expression vectors, and recovering the engineered PrAg proteins from the cell cultures.

Pharmaceutical Formulations

While the engineered PrAg proteins may be administered directly to a subject, the methods of the present invention are preferably based on the administration of a pharmaceutical formulation comprising one or more engineered PrAg proteins and a pharmaceutically acceptable carrier or diluent. Thus, the invention includes pharmaceutical formulations comprising one or more of the engineered PrAg proteins defined herein and a pharmaceutically acceptable carrier or diluent.

Pharmaceutically acceptable carriers and diluents are commonly known and will vary depending on the particular engineered PrAg protein being administered and the mode of administration. Examples of suitable carriers and diluents include saline, buffered saline, dextrose, water-for-injection, glycerol, ethanol, and combinations thereof, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin), hydrophilic and hydrophobic carriers, and combinations thereof. Hydrophobic carriers include, for example, fat emulsions, lipids, PEGylated phospholipids, polymer matrices, biocompatible polymers, liposhperes, vesicles, particles, and liposomes, other stabilizing agents, solubilizing agents and surfactants, buffers and preservatives, tonicity agents, bulking agents, and lubricating agents. The formulations comprising engineered PrAg proteins will typically have been prepared using engineered PrAg proteins from cultures prepared in the absence of any non-human components, such as animal serum (e.g., bovine serum albumin).

The pharmaceutical formulations of the present invention may be formulated, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration.

Parenteral formulations using hydrophobic carriers include, for example, fat emulsions and formulations containing lipids, liposhperes, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

Depending on the means of administration, the dosage may be administered all at once, such as with an oral formulation in a capsule or liquid, or slowly over a period of time, such as with an intramuscular or intravenous administration.

The amount of engineered PrAg proteins, alone or in a pharmaceutical formulation, administered to a subject is an amount effective for the treatment of a disease or condition, such as cancer. Thus, therapeutically effective amounts of the engineered PrAg proteins are administered to subjects when the methods of the present invention are practiced. In general, between about 0.1 ug/kg and about 1000 mg/kg of the engineered PrAg protein per body weight of the subject is administered. Suitable ranges also include between about 50 ug/kg and about 500 mg/kg, and between about 10 ug/kg and about 100 mg/kg. However, the amount of engineered PrAg protein administered to a subject will vary between wide limits, depending upon the location, source, extent and severity of the disease, the age and condition of the subject to be treated, etc. A physician will ultimately determine appropriate dosages to be used.

The amount of the selected compound or co-factor administered in conjunction with the engineered PrAg proteins, alone or in a pharmaceutical formulation, is also an amount effective for the treatment of a disease or condition, such as cancer, in the subject. Thus, therapeutically effective amounts of the selected compound or co-factor are administered to subjects when the methods of the present invention are practiced. While the amount of the selected compound or co-factor administered to a subject will vary widely depending on the identity of the selected compound or co-factor, as well as the disease or condition being treated, in general, between about 0.001 ug/kg and about 1000 mg/kg of the selected compound or co-factor per body weight of the subject is administered. Suitable ranges also include between about 50 ug/kg and about 500 mg/kg, and between about 10 ug/kg and about 100 mg/kg.

Administration frequencies of the engineered PrAg proteins and pharmaceutical formulations comprising the engineered PrAg proteins will vary depending on factors that include the location of the disease, the identity of the disease, the severity of the disease, and the mode of administration, among other factors. As non-limiting examples, each formulation may be independently administered 4, 3, 2 or once daily, every other day, every third day, every fourth day, every fifth day, every sixth day, once weekly, every eight days, every nine days, every ten days, bi-weekly, monthly and bi-monthly. The concentration of the protein in the formulation may vary or be the same in each formulation.

The duration of treatment will depend on relevant factors concerning the disease and will be best determined by the attending physician. However, continuation of treatment is contemplated to last for a number of days, weeks, or months.

In each embodiment and aspect of the invention, the subject is a human, a non-human primate, bird, horse, cow, goat, sheep, a companion animal, such as a dog, cat or rodent, or other mammal.

The invention also provides a kit comprising one or more containers filled with one or more engineered PrAg proteins or pharmaceutical formulations comprising one or more engineered PrAg proteins. The kit may also comprise one or more containers filled with one or more co-factors or pharmaceutical formulations comprising one or more co-factors.

The kit may further include instructions for use. Associated with the kit may further be a notice in the form prescribed by a governmental agency regulating the manufacture, use or sale of pharmaceuticals or biological products, which notice reflects approval by the agency of manufacture, use or sale for human administration.

III. EXAMPLES

Example 1

PrAg-PCIS

The membrane-anchored serine protease testisin (PRSS21) is synthesized with a 17-amino acid carboxy-terminal hydrophobic extension that is post-transcriptionally modified with a glycosyl-phosphatidylinositol (GPI) linkage that serves to anchor the protease to the extracellular side of the plasma membrane [49-52]. Testisin has remarkably specific tissue distribution, being constitutively expressed in abundance only in spermatocytes, where it has a specific role in male fertility [53-55]. Yet, testisin possesses the characteristics of a Cancer/Testis Antigen (CTA), a group of proteins whose expression is normally restricted to testis, but which are frequently aberrantly activated in tumors [56,57].

Testisin is strongly overexpressed in human invasive epithelial ovarian cancers, as well as cervical cancers, while being undetectable in normal ovarian or cervical tissues. In an RT-PCR study of ovarian tumors, Shigemasa et al. [58] reported that testisin was present in 80-90% of stage 2 or 3 disease. Bignotti et al. [59] also found testisin expressed in primary and metastatic ovarian tumors. Overexpression of testisin in ovarian tumor cells resulted in increased colony formation in soft agar and increased xenograft tumor growth in severe combined immunodeficient (SCID) mice [60]. Its increased expression has also been found to enhance matrigel invasion of cervical cancer cells [61]. Conversely, reduction of endogenous testisin expression via siRNA-mediated knockdown in ovarian and cervical tumor cell lines led to reduced colony formation, reduced invasion in cell culture, and reduced cellular resistance to the chemotherapy drug adriamycin [60,61]. The selective expression of testisin by human tumors relative to its normally restricted expression in testis, combined with the relationship of testisin expression to tumorigenic processes, suggested that testisin is an attractive target for anti-tumor therapeutic approaches.

In light of these studies, an engineered PrAg protein comprising a testisin cleavage site in place of the furin cleavage site was produced. This engineered PrAg protein is termed PrAg-PCIS. In particular, eight amino acids flanking the native furin cleavage site within PrAg (RKKRSTSA; SEQ ID NO:56) were replaced with a sequence that can be cleaved by testisin. The amino acid of PrAg-PCIS is provided in SEQ ID NO:54 and the nucleic acid sequence encoding the protein is provided in SEQ ID NO:55.

As shown in below, alteration of the cleavage site abrogated furin activation and resulted in a potent anti-tumor prodrug. The engineered PrAg-PCIS protein is a testisin substrate that is cleaved and activated by testisin in vitro and in cell culture, and it has potent anti-tumor cell activity when combined with a recombinant LF-Pseudomonas exotoxin based payload (FP59). Moreover, in vivo administration of the toxin inhibited growth of established xenograft tumors in mice by inducing tumor necrosis and reducing tumor cell proliferation.

Materials and Methods

Reagents

Enzymes for recombinant DNA preparation were purchased from New England BioLabs. Recombinant mouse testisin (6820-SE-10), human hepsin (4776-SE-10), human prostasin (4599-SE), and HAT (2695-SE) were purchased from R&D Systems. Each protease was activated according to the manufacturer's instructions. Recombinant human thrombin (470HT) and recombinant human uPA (ADG125N) were purchased from American Diagnostica. Recombinant human PCI and mouse anti-PCI antibody were prepared as previously described [80,81]. Briefly, recombinant PCI was prepared in *Escherichia coli* and purified using $Ni^{2+}$-chelate and heparin-sepharose affinity chromatography, as in [81]. Recombinant human furin was provided by Dr. Iris Lindberg (University of Maryland School of Medicine, Baltimore, Md.) [82]. Recombinant human matriptase was provided by Dr. Richard Leduc (Universite de Sherbrooke, Quebec, Canada) [83]. Human aPC was provided by Dr. Li Zhang (University of Maryland Baltimore School of Medicine, Baltimore, Md.) [84]. Aprotinin (A1153) was purchased from Sigma-Aldrich. Rabbit anti-PrAg antibody (no. 5308) was prepared as previously described [16]. Additional antibodies included goat anti-HAI-1 (AF1048) and goat anti-HAI-2 (AF1106) (R&D Systems), rabbit anti-matriptase (IM1014) (Calbiochem), mouse anti-prostasin (612172) (BD Transduction Laboratories), rabbit anti-glyceraldehyde 3-phosphate dehydrogenase (GAPDH) (14C10) (Cell Signaling Technologies), rabbit anti-hepsin (100022) (Cayman Chemical); anti-mouse and anti-rabbit horseradish peroxidase (HRP)-conjugated antibodies (Jackson ImmunoResearch Laboratories), and anti-goat HRP-conjugated antibody (KPL). Mouse Pro1.4.C25.1 anti-testisin antibody was produced by standard procedures from a hybridoma cell line (PTA-6076) (ATCC).

Real-time Quantitative PCR (qPCR)

RNA was isolated from cell lines using the RNeasy Kit (Qiagen). Reverse transcription was performed using Taqman Reverse Transcription Reagents (Applied Biosystems). qPCR was performed using testisin (Hs00199035_ml), hepsin (Hs01056332 _ml), matriptase (Hs00222707_ml), GAPDH (Hs02758991_gl) and beta-actin (β-actin) (Hs99999903) primers and Taqman RT-PCR reagents (Applied Biosystems). mRNA expression levels were normalized to GAPDH or β-actin.

Cell lysis and Immunoblotting

Cells were lysed in cell lysis buffer (150 mM NaCl, 10 mM $CaCl_2$, 50 mM HEPES (pH 7.3), 0.5% Triton X-100, 0.5% NP-40, Complete Mini-EDTA Protease Inhibitor Cocktail (Roche)), and protein concentrations determined by Bradford assay. Samples containing equal protein were heated at 95° C. for 5 minutes in Laemmli sample buffer containing 10% beta-mercaptoethanol and analyzed by SDS-polyacrylamide gel electrophoresis (PAGE), using 4-12% or 10% NuPage Bis-Tris pre-cast gels (Life Technologies), followed by immunoblotting using PVDF membranes (Life Technologies). Membranes were blocked for 30 minutes in 5% (w/v) non-fat milk and then sequentially incubated with primary and HRP-conjugated secondary antibodies. HRP activity was detected using SuperSignal West Pico Chemiluminescent Substrate (Thermo Scientific).

Plasmids and Mutagenesis

A two-step overlap PCR strategy was employed to mutate the cDNA bases encoding the furin cleavage site in the PrAg expression plasmid pYS5-PA33 [85]. pYS5-PA33 (SEQ ID NO:67) served as the template for the first round of PCR using the primers denoted 'A' (below). The resulting PCR reaction was digested with DpnI and the mutant plasmid cloned by standard techniques and used as the template for the second round of PCR using primers denoted 'B' (below). The resulting PCR reaction was digested with DpnI and the final mutant plasmid cloned and verified by DNA sequencing.

```
PrAg-PCIS 'A':
F:
                                        (SEQ ID NO: 57)
5'GCTGCTAGATCGGCGCGTCTAGGACCTACGG3'

R:
                                        (SEQ ID NO: 58)
5'CCGTAGGTCCTAGACGCGCCGATCTAGCAGC3'

PrAg-PCIS 'B':
F:
                                        (SEQ ID NO: 59)
5'CTTCGAATTCATTCACGTTTAGATCGGCGCGTCTAGG3'

R:
                                        (SEQ ID NO: 60)
5'CCTAGACGCGCCGATCTAAACGTGAATGAATTCGAAG3'
```

Expression plasmids encoding human matriptase [86], human HAI-1 [86], and human HAI-2 [87] were provided by Dr. Chen-Yong Lin (Georgetown University, Washington D.C.). cDNA encoding human testisin (GPI-testisin) [51], cloned into pcDNA3.1 expression plasmid (Life Technologies), was mutated by site-directed mutagenesis using the primers denoted below using the QuikChange Mutagenesis kit (Stratagene) to create 'zymogen-locked' activation site (R41A-testisin) and catalytic triad (S238A-testisin) mutants of testisin. Similarly, cDNA encoding human hepsin (WT-hepsin) [88], cloned into pcDNA 3.1, was mutated to create a catalytic triad S353A-hepsin mutant (S353A-hepsin). Cloning and mutagenesis accuracy was verified by DNA sequencing.

```
R41A-testisin:
F:
                                        (SEQ ID NO: 61)
5'GGGTCATCACGTCGGCGATCGTGGGTGG3'

R:
                                        (SEQ ID NO: 62)
5'CCTCTCCACCCACGATCGCCGACGT3'

S238A-testisin:
F:
                                        (SEQ ID NO: 63)
5'CCTGCTTCGGTGACGCAGGCGGACCCTTGG3'

R:
                                        (SEQ ID NO: 64)
5'CAGGCCAAGGGTCCGCCTGCGTCAC3'

S353A-hepsin:
F:
                                        (SEQ ID NO: 65)
5'GCCTGCCAGGGCGACGCGGGTGGTCCCTTTGTG3'

R:
                                        (SEQ ID NO: 66)
5'CACAAAGGGACCACCCGCGTCGCCCTGGCAGGC3'
```

Expression and Purification of PrAg Proteins

Recombinant anthrax toxin protective antigens (PrAg-WT, PrAg-PCIS), recombinant LF, and FP59 were generated and purified as previously described [16,66]. Briefly, expression plasmids containing PrAg sequences contained in the *E. coli Bacillus* expression plasmids pYS5 or pYS5-PA33, were transformed into the non-virulent *B. anthracis* strain BH460. The proteins were secreted into the culture supernatants and purified by ammonium sulfate precipitation and chromatography on a Mono-Q column to high yield and purity, as described [66]. The LF and FP59 used herein have the native N-terminal sequence of AGG [89].

PCI Cleavage Assay

Recombinant hepsin or matriptase (50 nM) were incubated with 50 nM recombinant PCI. Recombinant testisin (50 nM) was incubated with 500 nM recombinant PCI. After 30 minutes of incubation at room temperature, in 50 mM Tris-HCl (pH 7.5), 150 mM NaCl, and 10 mM $CaCl_2$, or at indicated intervals, Laemmli sample buffer containing 10% beta-mercaptoethanol was added to the reactions. Samples were immunoblotted for PCI cleavage or protease-PCI complex formation using anti-PCI, anti-hepsin, or anti-matriptase antibodies.

Peptide Assays

Peptide cleavage assays were performed using 10 nM recombinant testisin, 10 nM recombinant hepsin, or 100 nM recombinant matriptase, and 100 nM chromogenic succinyl-AAPR-p-nitroaniline peptide (Bachem). Reaction absorbance (abs) values were measured at 420 nm using a spectrophotometer (TECAN) at times indicated in the figure legend. The change in absorbance units is relative to the absorbance measured in the absence of peptide substrate. The absorbance of peptide substrate alone did not increase in the absence of protease over time.

In vitro PrAg Cleavage Assays

Recombinant PrAg proteins (1 μM) were incubated with recombinant proteases (50 nM) for 2.5 hours, or indicated intervals, at 30° C., in 50 mM HEPES (pH 7.3), 10 mM $CaCl_2$, 150 mM NaCl, and 0.05% (v/v) Brij-35. Reactions were stopped by addition of Laemmli sample buffer containing 10% beta-mercaptoethanol to the samples. PrAg cleavage was analyzed by SDS-PAGE followed by immunoblotting using anti-PrAg antibody.

For densitometry of PrAg processing, all values were measured using Image J software and normalized to GAPDH expression. Individual PrAg 83-kDa and 63-kDa values for each timepoint are calculated relative to the sum value of PrAg 83-kDa and 63-kDa at that timepoint, which was set equal to 1.

Cell Culture and Transfections

Human cell lines were purchased from American Type Culture Collection (ATCC), with the exception of NCI/ADR-Res cells, which were purchased from the NCI-DCTD repository (Frederick, Md.). Cell lines were cultured and maintained at 37° C. in a 5% $CO_2$/95% air environment in Dulbecco's Modified Eagle's Medium (DMEM) supplemented with 10% heat-inactivated fetal bovine serum (FBS) and 100 units/mL penicillin, 100 μg/mL streptomycin, and 2 mM L-glutamine. All cells were routinely tested and confirmed to be free of mycoplasma contamination. HEK293T cells were transfected with expression plasmids encoding full-length human GPI-anchored testisin (HEK/GPI-testisin), S238A-testisin catalytic triad mutant (HEK/S238A-testisin), R41A-testisin 'zymogen-locked' activation site mutant (HEK/R41A-testisin), or vector alone (HEK/vector) using Lipofectamine 2000 (Life Technologies). Two stably-transfected pools of each transfection were obtained by selection in hygromycin and testisin/mutant expression determined by immunoblot (data not shown). HeLa cells were transiently transfected or co-transfected with expression plasmids encoding matriptase (WT-matriptase), prostasin [90], hepsin (WT-hepsin), S353A-hepsin catalytic triad mutant (S353A-hepsin), HAI-1, HAI-2, or vector alone (vector) using Lipofectamine 2000.

Knockdown by RNA Interference HeLa cells were transfected with 20 nM testisin-specific STEALTH siRNAs (HSS116894; HSS173992) (Life Technologies) or 20 nM luciferase-specific negative control (Luc-siRNA) (Life Technologies) using Dharmafect 1 (Dharmacon). After 48 hours, cells were harvested for analysis of testisin mRNA and protein expression, or used in MTT cytotoxicity assays. The efficiency of testisin knockdown was analyzed by qPCR and immunoblotting.

MTT Cytotoxicity Assays

Cells were incubated with various concentrations of PrAg-PCIS or PrAg-WT (as indicated in figure legends) and FP59 (50 ng/mL) in growth media for indicated times. Media was replaced with fresh media and cell viability was assayed from 24-48 hours later (as indicated in the figure legends) by adding MTT (3-(4,5-dimethylthiazol-2-yl)-2,5-diphenyltetrazolium bromide) (Millipore) to a final concentration of 1.25 mg/mL, and incubating for 45 minutes to one hour at 37° C. MTT was dissolved in growth media and filtered through a 0.22 μm syringe filter. The formed pigment was solubilized with 0.5% (w/v) SDS, 25 mM HCl, in 90% (v/v) isopropanol. Absorbance was measured using a spectrophotometer (TECAN) at 550 nm and 620 nm (reference wavelength). Values obtained for incubation of cells with PrAg toxins were normalized to those obtained for the cells incubated with FP59 alone (100%). $EC_{50}$ is defined as the concentration (derived from the viability plots) of PrAg toxin required to kill 50% of the cells.

In vivo Tumor Xenograft Models

Female athymic nude mice (NU/NU) (6-8wks old) (Charles River) were housed and monitored according to Institutional Animal Care and Use Committee guidelines, given free access to food and water, and maintained in a 12 hour dark/light environment. $2.5 \times 10^6$ HeLa tumor cells were injected subcutaneously into the right hind flanks of the mice. Upon measurable tumor growth (~50-200 mm$^3$), mice were distributed into cohorts containing mice bearing approximately equal individual tumor volumes and approximately equal average tumor volumes. Each mouse received a 100 μL intratumoral injection, injected into multiple spots in the tumor, every three days for a total of three injections. Tumor dimensions were measured with calipers at indicated timepoints in a blinded manner with respect to tumor treatment. Tumor volume was calculated using the formula 0.5×length×width$^2$. Experiments were concluded when one or more mice reached predetermined endpoints (weight gain>10%, tumor diameter>1 cm, tumor ulceration). Mice were then euthanized and tumors were removed, weighed (in a treatment-blinded manner), fixed in 10% zinc buffer, and stored in 70% ethanol for histology and immunohistochemical analysis.

Histopathological Analysis

Zinc-fixed tumor specimens were embedded in paraffin and 5 μm-thick sections were cut, deparafinized, and stained with hematoxylin and eosin (H&E) using standard procedures, or subjected to immunohistochemical analysis. For immunohistochemistry, samples were rehydrated, endogenous peroxidase activity blocked with 3% hydrogen peroxide in methanol, subjected to antigen retrieval in boiling sodium citrate, and then non-specific binding sites blocked with 5% goat serum. Sections were incubated overnight at 4° C. with 1:100 dilutions of rabbit anti-Ki67 (ab16667) (Abcam), rabbit anti-human activated caspase-3 (9661S) (Cell Signaling Technology), or rat anti-mouse CD31 (553370) (BD Pharmingen), followed by incubation for 30 minutes with 1:200 anti-rat or anti-rabbit biotinylated secondary antibodies. Antibody binding was detected using a Vectastain ABC Kit (Vector Laboratories). Sections were counterstained with hematoxylin, dehydrated, and mounted. Control slides were incubated with primary or secondary antibodies only. Images were obtained using an EVOS FL Auto Cell Imaging System (Life Technologies). Composite images of the whole tumor sections were obtained with a 10X objective and stitched together using the EVOS software, while individual fields were taken using 20× (H&E, Ki67, activated caspase-3) or 40× (CD31) objectives, respectively. Staining was quantified using Image J software (H&E, Ki67, activated caspase-3) and Photoshop (Adobe) (CD31). Quantification, performed in a treatment-blinded manner, was performed by outlining the tumors in the composite images and analyzing the tumor sections for % viable area (H&E) or % positive staining for the immunostained sections. Percentages were calculated using the ratio of viable area or stained area of the tumor to the total tumor area (areas determined by pixel count), as described in [91].

Statistical Analysis

Quantitative data are represented as mean values with their respective standard errors (SEM). Significance (relative to vector or vehicle control groups) was tested using unpaired two-tailed Student's t test, which was calculated using GraphPad software. p values<0.05 were considered statistically significant.

Results

Engineering the Mutant PrAg-PCIS Protein

The eight amino acid sequence $^{164}$RKKRSTSA (SEQ ID NO:56), containing the furin cleavage site (furin cleaves the peptide bond between R—S) in the mature wild-type PrAg protein (PrAg-WT; SEQ ID NO:3), was replaced with the sequence $^{164}$FTFRSARL (SEQ ID NO:28) to create PrAg-PCIS using an overlap PCR strategy. This new substrate sequence was derived from a region of protein C inhibitor (PCI, SERPINA5), within the reactive center loop and close to the C-terminus, and is known to be cleaved by testisin [62], as confirmed (see FIG. 1A), as well as by other serine proteases [63-65]. The mutant and wild-type PrAg cDNAs were expressed in the non-virulent *B. anthracis* strain BH460, and the secreted PrAg proteins purified in high yield using established protocols [66]. Incubation of the PrAg proteins with soluble furin revealed that mutation of the furin cleavage site to that in PrAg-PCIS abrogated furin cleavage, evidenced by its failure to convert the 83-kDa PrAg-PCIS to the activated 63-kDa form (FIG. 1B). PrAg-WT was cleaved by furin, as expected (FIG. 1B).

PrAg-PCIS Toxin is Cytotoxic to a Broad Range of Human Tumor Cells

The combination of PrAg and FP59, a fusion protein consisting of the PrAg binding domain of LF and the catalytic domain of *Pseudomonas aeruginosa* exotoxin A, has been shown to efficiently kill tumor cells following PrAg activation [67]. When translocated into the cytosol by activated PrAg, FP59 induces cytotoxicity by ADP-ribosylation and inhibition of translation elongation factor-2, resulting in inhibition of protein synthesis and the induction of cell death [67-69]. FP59 does not induce cytotoxicity alone, but must be delivered into cells via an activated PrAg protein to induce cell death. To compare the abilities of PrAg-PCIS and PrAg-WT to be activated by tumor cells and to deliver FP59, cytotoxicity assays were performed on a range of human tumor cell lines after treatment with FP59 in combination with PrAg-PCIS (PrAg-PCIS toxin) or PrAg-WT (PrAg-WT toxin). All tumor cell lines showed a dose-dependent sensitivity to the PrAg-PCIS toxin. In 7 of the 9 tumor lines (NCI/ADR-Res, SKOV3, ES-2, OVCAR3, LnCAP, DU-145, and PC3), the PrAg-PCIS toxin showed potent killing effects at doses similar to the PrAg-WT toxin (FIG. 1C). All the cell lines were susceptible to the furin-dependent PrAg-WT, as expected. To determine whether active tumor cell-surface serine proteases were targets of the PrAg-PCIS toxin, ES-2 (ovarian), and DU-145 (prostate) tumor cell lines were pretreated with the cell membrane impermeable serine protease inhibitor aprotinin (FIGS. 1D,E). Serine protease inhibition by aprotinin resulted in significantly reduced PrAg-PCIS toxin-induced cytotoxicity in both cell lines, implicating active cell-surface serine proteases in the mechanism of PrAg-PCIS activation. The incomplete protection from PrAg-PCIS activation conferred by aprotinin could have resulted from partial inhibition of protease activity by aprotinin or toxin activation mediated by serine proteases that are not inhibited by aprotinin.

Protease Selectivity of PrAg-PCIS

Figures 2A, 2B:
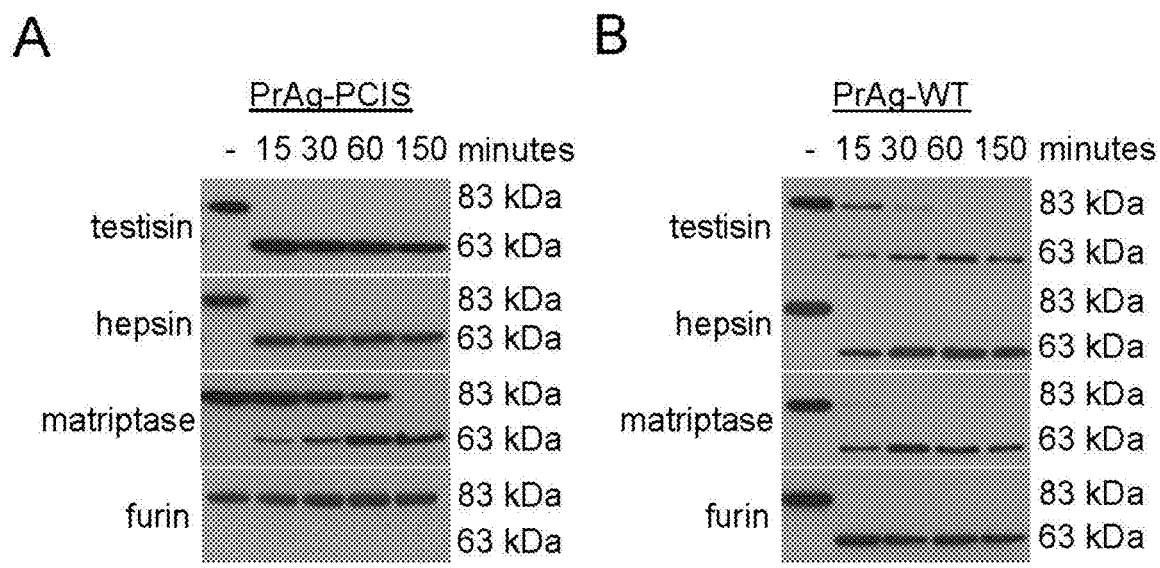
FIGS. 2A-2B. PrAg-PCIS is susceptible to in vitro cleavage activation by testisin, hepsin, and matriptase.

Many pericellular proteases, including the membrane-anchored serine proteases, have preferred recognition sequences for substrate cleavage. Yet, there exists promiscuity in sequence recognition and cleavage, particularly with regard to the amino acids adjacent to the cleavage site. Incubation of PrAg-PCIS with the recombinant catalytic domains of several membrane-anchored serine proteases and other potentially reactive pericellular serine proteases resulted in activation cleavage of PrAg-PCIS from the 83-kDa to the 63-kDa form by the membrane-anchored serine proteases testisin, hepsin (HPN), matriptase (ST14), and to a lesser extent human airway trypsin-like protease (HAT, TMPRSS11D) (FIG. 1B). As noted previously, PrAg-PCIS was not susceptible to cleavage by soluble furin and showed relatively low susceptibility to cleavage by the secreted serine proteases thrombin (F2), activated protein C (aPC, PROC), or uPA (FIG. 1B). To further investigate the susceptibility of PrAg-PCIS to proteolytic cleavage by testisin, hepsin, and matriptase compared to furin, PrAg-PCIS and PrAg-WT proteins were incubated with the respective recombinant serine protease domains and cleavage was assessed at intervals over time. Testisin and hepsin showed complete activation cleavage of PrAg-PCIS within 15 minutes under the assay conditions, whereas matriptase appeared less effective at PrAg-PCIS cleavage (FIG. 2A). As expected, PrAg-WT was effectively cleaved by furin (FIG. 2B). Interestingly, PrAg-WT was susceptible to activation cleavage by each of the three serine proteases, testisin, hepsin, and matriptase (FIGS. 1B, 2B), suggesting a possible role for these membrane-anchored serine proteases in facilitating native PrAg-WT activation and subsequent anthrax toxicity in nature. Analysis of testisin, hepsin, and matriptase mRNA expression in the tumor cell lines susceptible to PrAg-PCIS toxin (FIG. 1C) revealed that the tumor cell lines expressed variable levels of some or all of the three proteases, providing the means for PrAg-PCIS activation (data not shown).

Figure 3A:
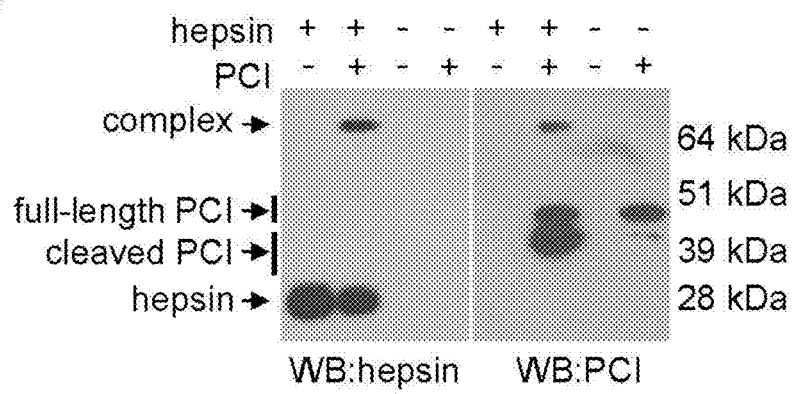
FIGS. 3A-3C. The susceptibility of PrAg-PCIS to proteolytic cleavage by hepsin and matriptase is consistent with their abilities to cleave the RCL of PCI to form protease-serpin inhibitory complexes.
Figure 3B:
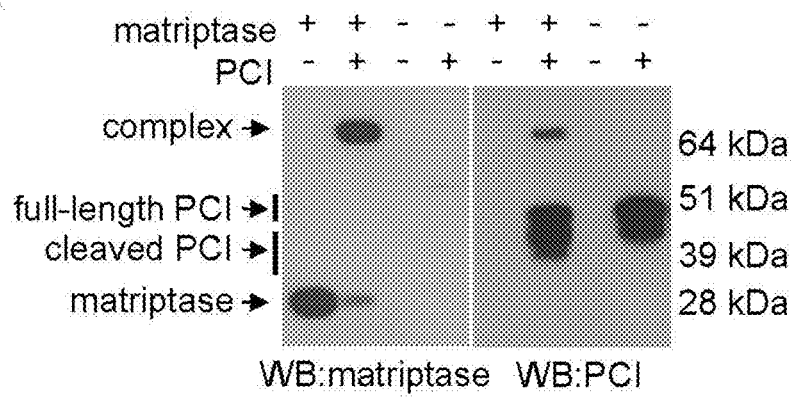

The observation that PrAg-PCIS was susceptible to cleavage by hepsin and matriptase suggested that in addition to native PCI being a substrate of testisin, PCI might be a substrate of these proteases. PCI is a member of the serpin family, whose structure and inhibitory mechanism has been well-characterized [70,71]. Cleavage of the serpin reactive center loop (RCL) can result in the formation of a protease-inhibitory complex, consisting of PCI covalently bound to the serine protease or production of lower molecular weight cleaved forms of PCI [70,71]. Incubation of hepsin and matriptase recombinant catalytic domains with PCI resulted in the appearance of cleaved forms of PCI, as well as higher molecular weight complexes representing SDS-resistant serpin-serine protease inhibitory complexes (FIGS. 3A,B).

Figure 3C:
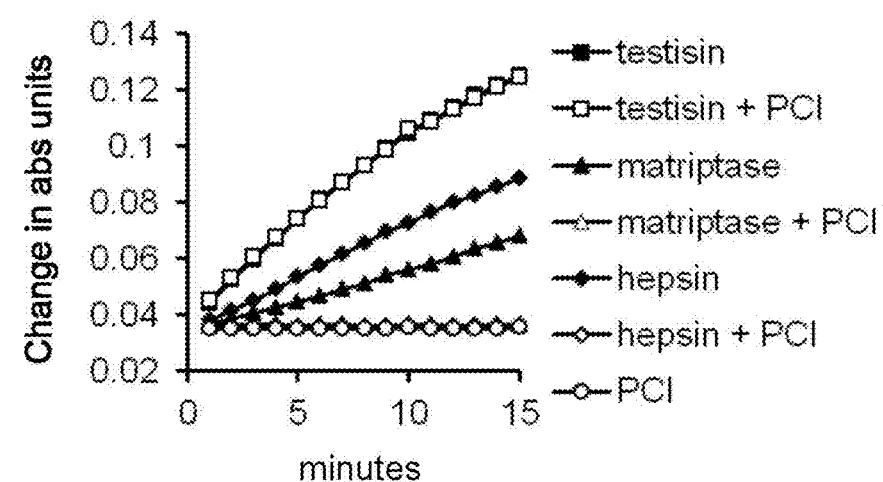

While PCI is a substrate for testisin, inhibitory complexes are not observed when PCI is incubated with testisin (FIG. 1A), and, in addition, testisin cleaves PCI at a second site (FIG. 1A) as reported previously [62]. Assay of testisin, hepsin, and matriptase peptidase activities using a chromogenic peptide in the absence or presence of PCI confirmed that PCI functions as an inhibitor of hepsin and matriptase catalytic activities, but not testisin (FIG. 3C). The abilities of hepsin and matriptase to cleave the RCL of PCI to form protease-serpin complexes, and of PCI to inhibit the catalytic activities of hepsin and matriptase, is consistent with the susceptibility of PrAg-PCIS to proteolytic cleavage by hepsin and matriptase.

Processing of PrAg-PCIS by Cell-expressed GPI-anchored Testisin

Figures 4A, 4B, 4C, 4D:
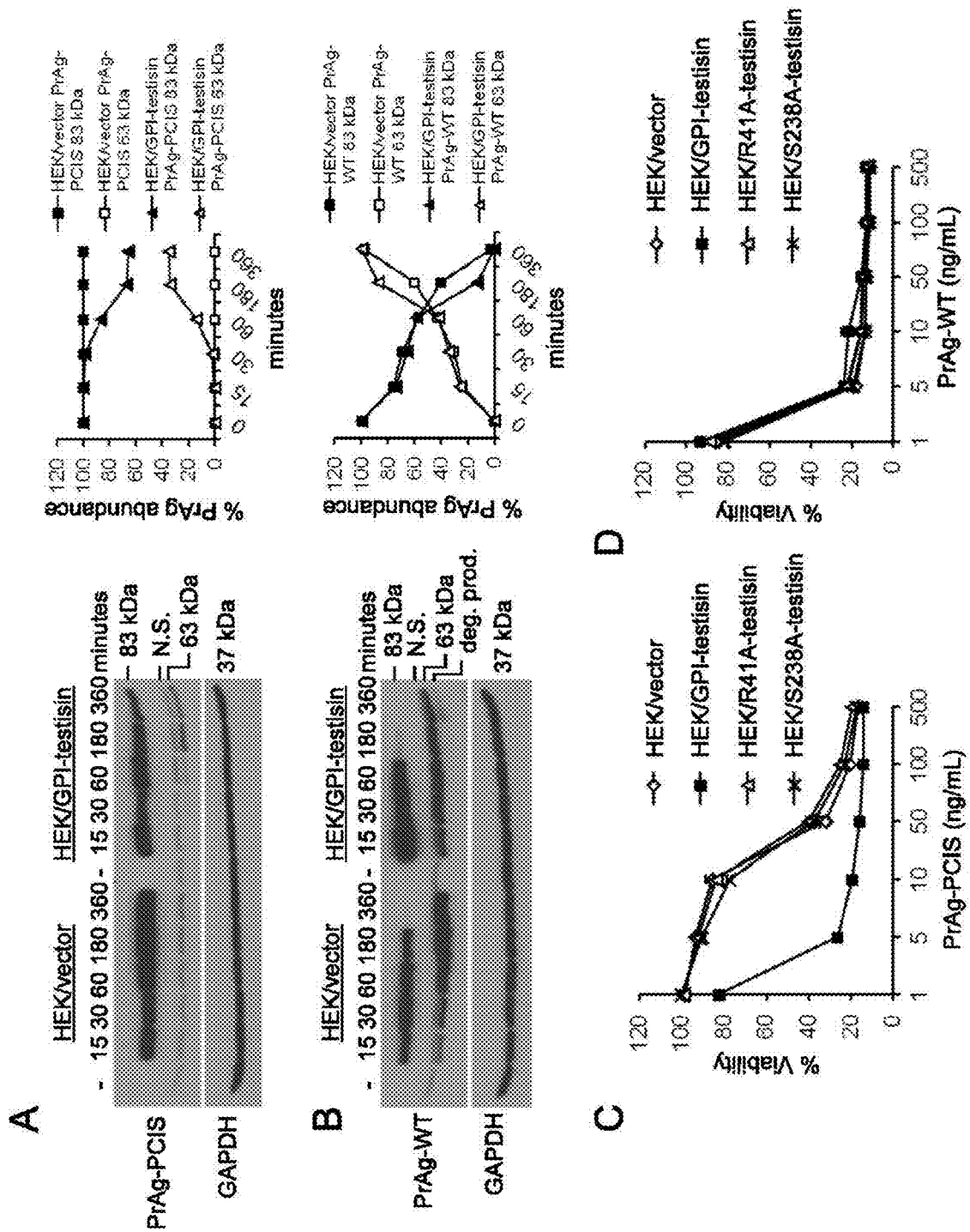
FIGS. 4A-4D. Expression of GPI-anchored testisin in HEK293T cells increases PrAg-PCIS processing and PrAg-PCIS toxin-induced tumor cell killing.

Following activation cleavage on the cell surface, the cleaved PrAg forms an oligomer which is internalized by the cell. To confirm that testisin anchored on a tumor cell surface can process PrAg-PCIS to an activated form, HEK293T cells stably expressing full-length human testisin (HEK/GPI-testisin) or vector alone (HEK/vector) were exposed to PrAg-PCIS or PrAg-WT for various times up to 6 hours and assayed for the appearance of the 63-kDa activation product. The processing of PrAg-PCIS to the 63-kDa form was detectable in HEK/GPI-testisin cells within 30 minutes and these levels increased with time (FIG. 4A). Importantly, PrAg-PCIS was not processed in the absence of testisin in HEK/vector cells (FIG. 4A), consistent with the resistance of PrAg-PCIS to cleavage by endogenous furin-like proteases (FIG. 1B). Incubation of the cells with the furin-activatable PrAg-WT results in the rapid processing of 83-kDa PrAg-WT to the activated 63-kDa form within 15 minutes, and by 6 hours, all of the PrAg-WT was processed to the PrAg-WT 63-kDa form in both HEK/GPI-testisin and HEK/vector cells (FIG. 4B). Loss of the 83-kDa PrAg-WT occurred more rapidly in HEK/GPI-testisin cells, possibly reflecting increased processing due to the presence of testisin, in addition to furin.

PrAg-PCIS Toxin is Cytotoxic to Cells Expressing Active GPI-anchored Testisin

To investigate potential tumor cell killing resulting from testisin activation of PrAg-PCIS, cytotoxicity assays were performed using HEK/GPI-testisin and HEK/vector cells.

HEK/GPI-testisin cells showed a dose-dependent sensitivity to killing by PrAg-PCIS toxin (i.e., PrAg-PCIS and FP59) (FIG. 4C), similar to the furin-dependent PrAg-WT toxin (i.e., PrAg-WT and FP59)($EC_{50}$ 3 ng/mL for PrAg-PCIS vs 3 ng/mL for PrAg-WT) (FIGS. 4C,D). HEK/vector cells were 10-fold less sensitive to PrAg-PCIS toxin ($EC_{50}$ 30 ng/mL), while showing similar susceptibility to the furin-dependent PrAg-WT toxin ($EC_{50}$ 3 ng/mL) (FIGS. 4C,D). FP59 and the PrAg proteins did not cause cellular cytotoxicity when incubated with the cells individually (data not shown). These data show that testisin can increase PrAg-PCIS activation and toxin-induced cytotoxicity. The dependence of this activity on active testisin was examined using HEK293T cells stably expressing two catalytically inactive testisin mutants, R41A-testisin and S238A-testisin. The R41A-testisin mutant encodes an Ala for $Arg^{41}$ mutation in the activation site of the testisin zymogen, thus maintaining the enzyme in a 'zymogen locked,' inactive conformation [72]. When HEK293T cells expressing R41A-testisin were incubated with the PrAg-PCIS toxin, viability was similar to that seen in the HEK/vector cell line ($EC_{50}$ 30 ng/mL for HEK/R41A-testisin vs 30 ng/mL for HEK/vector) (FIG. 4C). The S238A-testisin mutant encodes a substitution of Ala for $Ser^{238}$ of the catalytic triad, which is required for the mechanism of peptide bond cleavage by serine proteases [73]. Detection of the S238A-testisin mutant when expressed in HEK293T cells was relatively poor when compared with detection of the R41A-testisin mutant or testisin in these cells (data not shown) for unknown reasons. When incubated with PrAg-PCIS toxin, the presence of S238A-testisin did not result in increased activation of PrAg-PCIS toxin, as viability of the HEK/S238A-testisin cells was similar to that of the HEK/R41A-testisin and HEK/vector alone cell lines ($EC_{50}$ 30 ng/mL) (FIG. 4C). As expected, cells expressing S238A-testisin and R41A-testisin mutants were as susceptible to killing by the furin-dependent PrAg-WT toxin as the HEK/GPI-testisin cells ($EC_{50}$ 3 ng/mL for HEK/S238A-testisin; $EC_{50}$ 3 ng/mL for HEK/R41A-testisin) (FIG. 4D). Together, these data show that testisin activity is responsible for the increased PrAg-PCIS induced cytotoxicity in HEK/GPI-testisin cells.

Tumor Cells Expressing Endogenous Testisin are Killed by the PrAg-PCIS Toxin

Figures 5A, 5B, 5C, 5D, 5E:
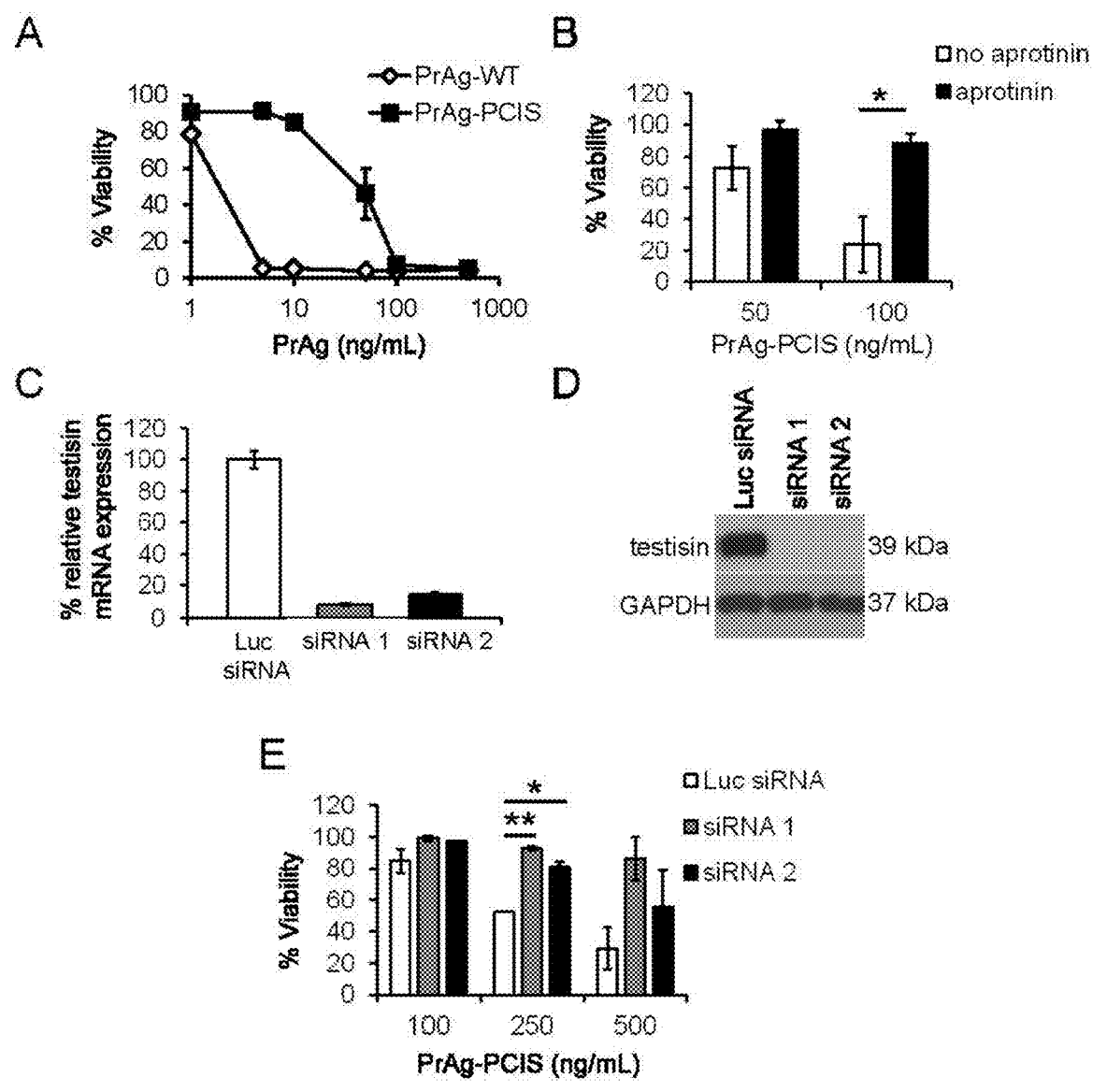

To investigate the activation of PrAg-PCIS toxin (i.e., PrAg-PCIS and FP59) by endogenous testisin in a natural tumor cell system, HeLa cervical cancer cells, which constitutively express testisin [60,74], were treated with the PrAg-PCIS and FP59. Increasing concentrations of PrAg-PCIS resulted in substantial HeLa cell death that was dose-dependent, although HeLa cells were less sensitive to the PrAg-PCIS toxin than to the PrAg-WT toxin (FIG. 5A). The FP59 and the PrAg proteins did not induce cytotoxicity when incubated with the cells individually (data not shown). Pre-incubation of the HeLa cells with aprotinin, which has been shown to inhibit testisin activity [74], prior to the addition of the PrAg-PCIS toxin, resulted in significant attenuation of toxicity (FIG. 5B), demonstrating that PrAg-PCIS toxin-induced cytotoxicity in HeLa cells is dependent on cell-surface serine protease activity, and suggesting that testisin may contribute to PrAg-PCIS activation on HeLa cells. The specific dependence of PrAg-PCIS toxin-induced cytotoxicity on the presence of testisin was revealed following knockdown of testisin expression in HeLa cells using siRNA. Efficient knockdown of testisin mRNA (FIG. 5C) and protein (FIG. 5D) levels were achieved using two independent testisin-specific siRNAs, compared to a control siRNA (Luc-siRNA). Incubation of the siRNA control cells with increasing concentrations of PrAg-PCIS toxin produced a dose-dependent decrease in cell viability, whereas HeLa cells depleted of testisin were relatively resistant to killing by the PrAg-PCIS toxin (FIG. 5E). Together, these data demonstrate that testisin is a significant contributor to PrAg-PCIS toxin activation on HeLa cells.

Figures 6A, 6B, 6C, 6D:
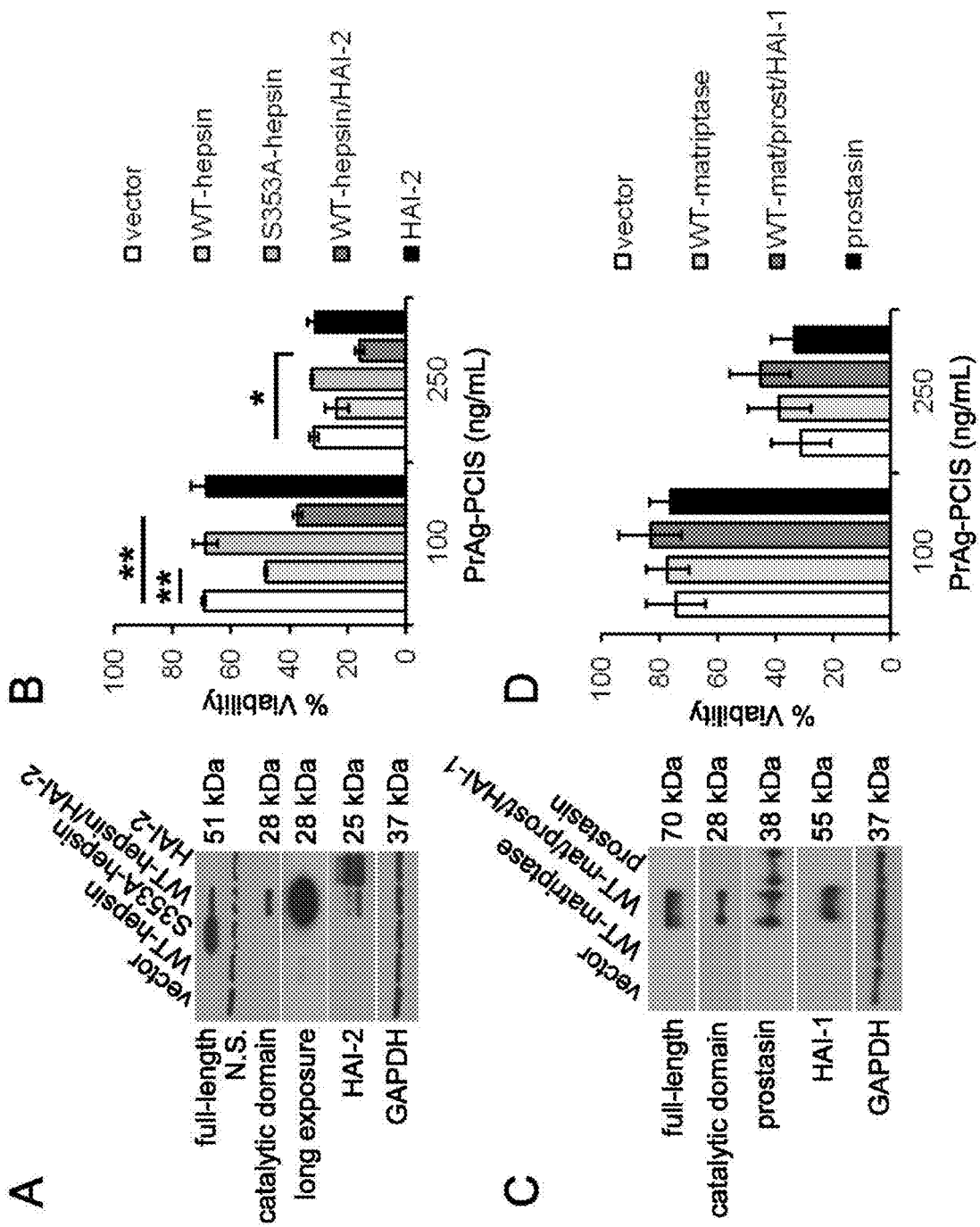

PrAg-PCIS Toxin is Cytotoxic to Tumor Cells Expressing Active Hepsin, but not Matriptase The activation cleavage of PrAg-PCIS by both recombinant matriptase and hepsin in vitro suggested that the full-length forms of these membrane-tethered enzymes could be additional activators of PrAg-PCIS. To test the role of cell-expressed hepsin in activating PrAg-PCIS, HeLa cells were transfected with expression plasmids encoding full-length hepsin or an inactive S353A-hepsin catalytic mutant (FIG. 6A). Because transfection of full-length hepsin results in low levels of detectable hepsin protein (FIG. 6A), hepatocyte growth factor activator inhibitor-2 (HAI-2, SPINT2), which likely functions as a chaperone protein to enhance hepsin protein stability, was also co-expressed with hepsin (FIG. 6A). The expression of hepsin in HeLa cells produced active hepsin, evidenced by the presence of a 28-kDa hepsin catalytic domain, which is produced after activation cleavage of the hepsin zymogen. The presence of full-length hepsin alone resulted in a 30% increase in PrAg-PCIS toxin-induced cytotoxicity in HeLa cells, and the HAI-2-enhanced hepsin activity resulted in a 43% increase in toxin-induced cytotoxicity relative to control cells (FIG. 6B), suggesting that cell surface hepsin is an activator of PrAg-PCIS.

To test the role of cell-expressed matriptase in activating PrAg-PCIS, full-length matriptase was expressed in HeLa cells. Efficient matriptase expression required co-expression with hepatocyte growth factor activator inhibitor-1 (HAI-1, SP INT 1) and prostasin (PRSS8), to enhance matriptase trafficking to the cell surface [75,76] and increase matriptase zymogen activation [77,78] (FIG. 6C). Co-expression of matriptase, HAI-1, and prostasin generated active matriptase as evidenced by the presence of the 28-kDa matriptase catalytic domain, which is produced after activation cleavage of the matriptase zymogen [79] (FIG. 6C). In contrast to hepsin, PrAg-PCIS activation and toxin-induced cytotoxicity was unaffected by the presence of matriptase (FIG. 6D). These data show that although the catalytic domain of matriptase is capable of PrAg-PCIS activation in solution, matriptase may not be a major contributor to PrAg-PCIS toxin activation on the cell surface, whereas hepsin likely contributes to PrAg-PCIS toxin activation on tumor cells that express hepsin.

PrAg-PCIS Toxin Inhibits Tumor Growth in a Preclinical Xenograft Mouse Model

Figures 7A, 7B, 7C, 7D:
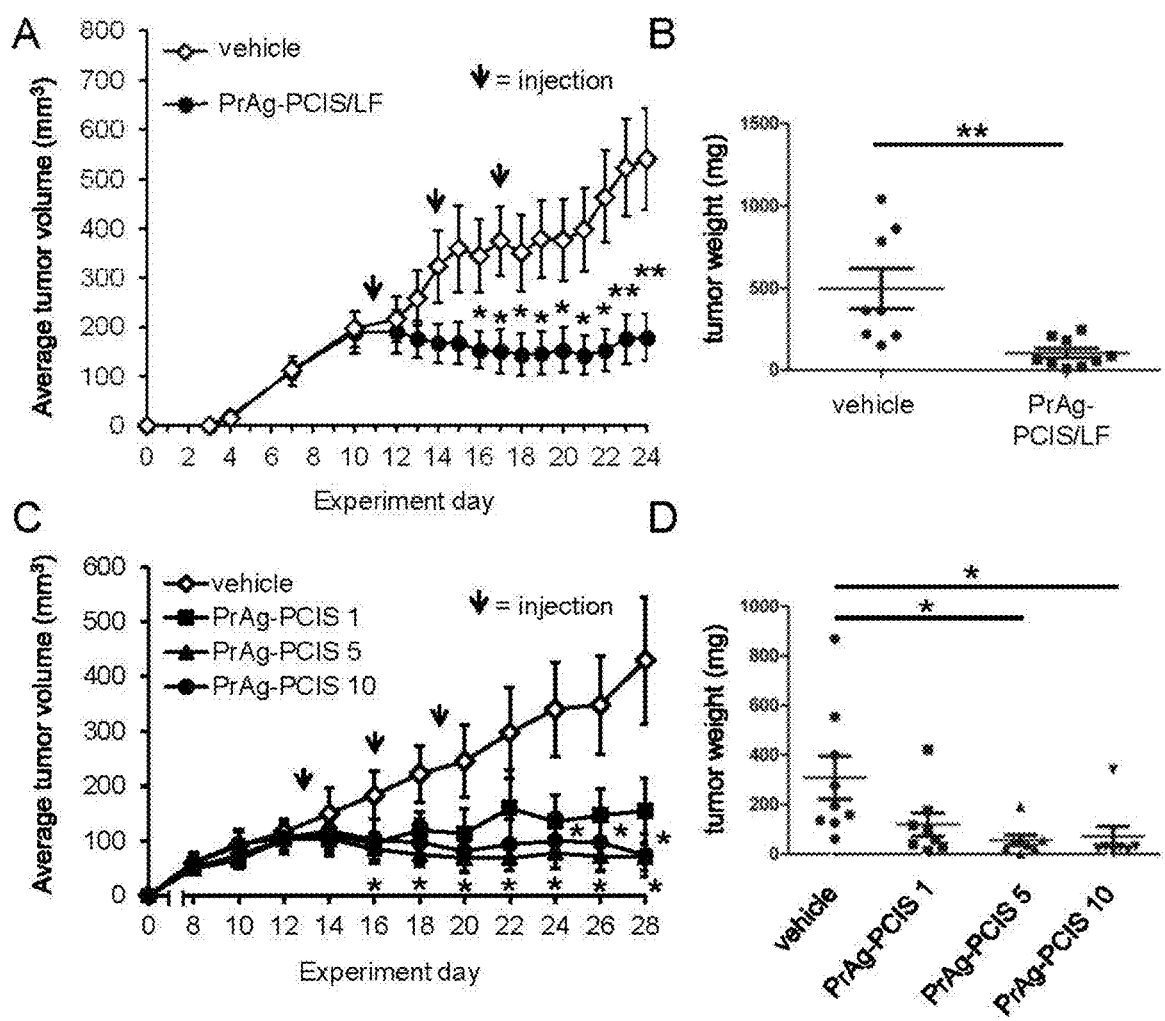
FIG. 7D) Tumor weights obtained after resection of tumors in FIG. 7C). *p<0.05, **p<0.01.

The ability of the PrAg-PCIS toxin to inhibit tumor growth in vivo was examined using a xenograft mouse model. Athymic female nude mice bearing subcutaneous HeLa tumors received three intratumoral injections (one every three days) of PrAg-PCIS toxin (10 μg PrAg-PCIS and 5 μg LF) or vehicle alone (PBS), and tumor growth was assessed by caliper measurements. LF was used in vivo in place of FP59 to avoid any off-target effects that may be associated with non-specific uptake of the very effective protein translation inhibitor FP59 [27]. After the first injection of PrAg-PCIS toxin, tumor growth arrested and did not increase compared with vehicle treated tumors, over the course of the experiment (FIG. 7A). Tumors were harvested and weighed up to 7 days after the final treatment. Tumor weights correlated well with measures of tumor volumes, with the mouse cohort that received PrAg-PCIS toxin showing a significant 5-fold reduction in average tumor weight relative to the cohort treated with vehicle alone (FIG. 7B).

The dose-dependence of tumor growth inhibition by PrAg-PCIS toxin was also investigated using this xenograft model. Cohorts of mice bearing subcutaneous HeLa tumors received three injections (one every three days) composed of 10 μg, 5 μg, 1 μg PrAg-PCIS toxin, or vehicle (5 μg LF in PBS). Tumor growth as assessed by caliper measurements again showed tumor growth arrest in all 3 cohorts treated with PrAg-PCIS toxin compared with vehicle alone treated animals over the course of the experiment (FIG. 7C). The tumor weights obtained at the end of the experiment correlated well with the measured tumor volumes (FIGS. 7C,D). The tumor volumes measured in mice treated with 10 μg and 5 μg doses of PrAg-PCIS toxin decreased significantly over the course of the experiment, showing 4.3-fold and 5.6-fold reduced average tumor weights, respectively, compared to vehicle alone, at the end of the experiment (FIGS. 7C,D). Tumors treated with the 1 μg dose of PrAg-PCIS toxin showed a non-significant trend toward reduced average tumor volume and average tumor weight relative to mice treated with vehicle alone (FIGS. 7C,D). Treatments with the PrAg-PCIS toxin were well-tolerated by the mice and did not appear to have any overt off-target side effects.

Treated mice did not experience substantial weight loss and necropsies revealed no gross abnormalities or organ damage (data not shown). These data demonstrate a significant effect of the PrAg-PCIS toxin in inhibiting tumor growth in a preclinical mouse model.

Figures 8A, 8B, 8C, 8D, 8E, 8F, 8G, 8H:
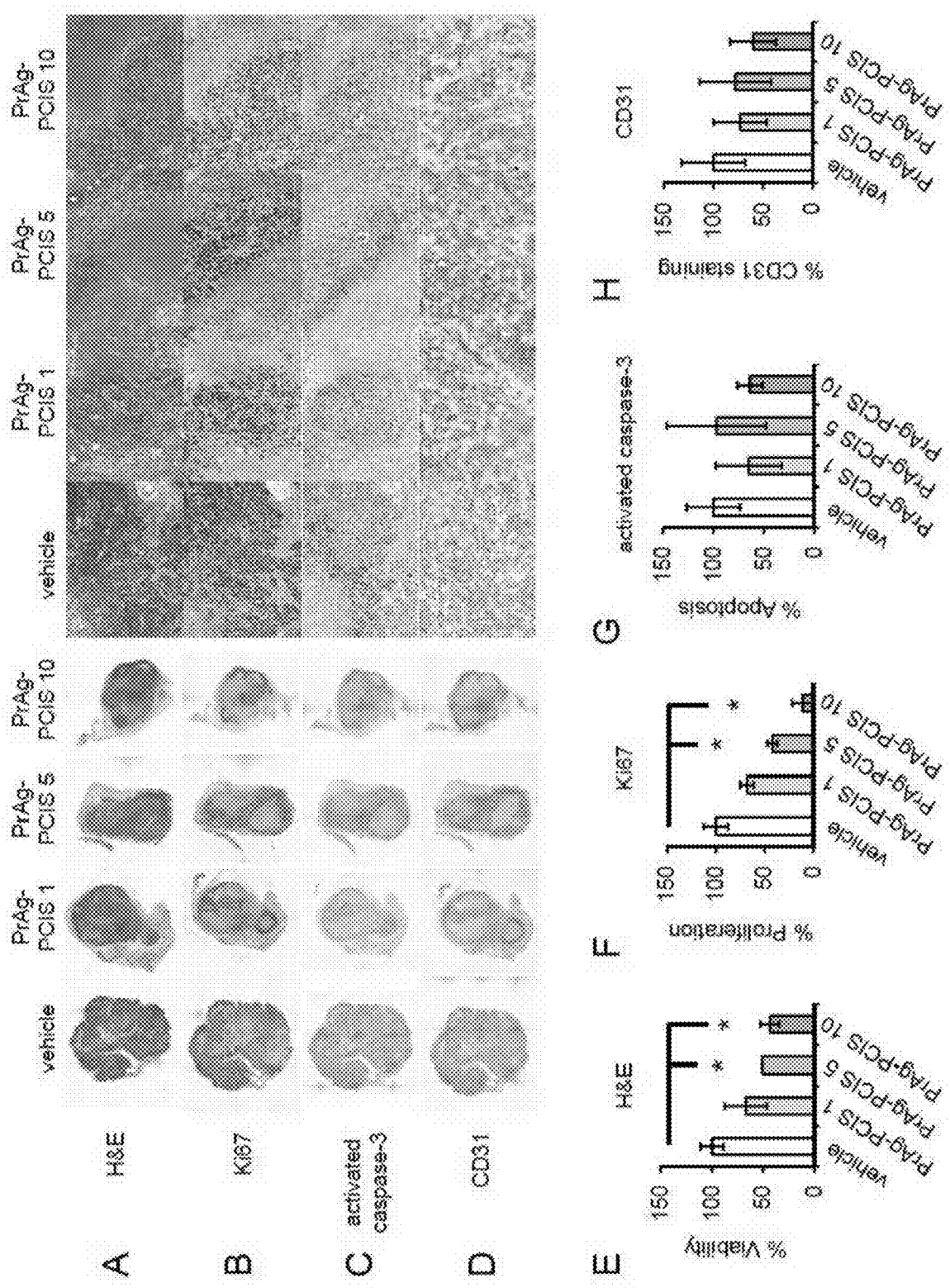
FIGS. 8A-8H. PrAg-PCIS toxin treatment increases tumor necrosis and reduces tumor cell proliferation.

Quantitative histomorphometric analyses were performed on serial sections of the harvested tumors to investigate the mechanistic basis for the potent anti-tumor activity of the PrAg-PCIS toxin. Microscopic analysis of sections stained with hematoxylin/eosin (H&E) showed that tumors exposed to either 10 μg PrAg-PCIS toxin or 5 μg PrAg-PCIS toxin presented with substantial areas of necrosis, as indicated by reduced staining of the tissue and the presence of patches of destroyed tumor with loss of nuclei (FIGS. 8A,E), which was not seen in the vehicle treated control group, which had significantly more viable tumor area (increased approximately 2-fold relative to toxin treated groups) (FIGS. 8A,E). The tumors treated with 1 μg PrAg-PCIS toxin also showed reduced staining and loss of viability, which did not quite reach statistical significance relative to the vehicle treated control group (FIGS. 8A,E). Staining for the proliferation marker Ki67 revealed that tumor cell proliferation in tumors treated with 10 μg PrAg-PCIS toxin or 5 μg PrAg-PCIS toxin was significantly reduced by 3.3-fold and 2.3-fold respectively, relative to vehicle treatment, and was associated only with the remaining viable areas of the tumors (FIGS. 8B,F). Apoptotic cells, evidenced by staining for activated caspase-3, were concentrated in the areas peripheral to the necrotic areas and adjacent to the viable areas of the tumors, but overall differences were not observed amongst the treatment groups (FIGS. 8C,G). Likewise, vessel density, as measured by CD31 staining, appeared not to be significantly affected by PrAg-PCIS toxin treatment and staining of vessels was confined to the viable areas of the tumors (FIGS. 8D,H). This data suggests that PrAg-PCIS toxin treatment inhibits tumor growth through the reduction of tumor cell proliferation and the induction of tumor necrosis.

Example 2

The methods, reagents and techniques described in detail in Example 1 above where use to generate three additional engineered PrAg proteins. The engineered PrAg-TAS protein had the native furin activation site replaced by the testisin zymogen activation site (IPSRIVGG; SEQ ID NO:4). The amino acid of PrAg-TAS is provided in SEQ ID NO:48 and the nucleic acid sequence encoding the protein is provided in SEQ ID NO:49. The engineered PrAg-PAS protein had the native furin activation site replaced by the prostration zymogen activation site (PQARITGG; SEQ ID NO:5). The amino acid of PrAg-PAS is provided in SEQ ID NO:50 and the nucleic acid sequence encoding the protein is provided in SEQ ID NO:51. The engineered PrAg-UAS protein had the native furin activation site replaced by a modified uPA zymogen activation site (PRFRITGG; SEQ ID NO:6). The amino acid of PrAg-UAS is provided in SEQ ID NO:52 and the nucleic acid sequence encoding the protein is provided in SEQ ID NO:53. Details regarding these three proteins, along with the PrAG-PCIS protein and the wild-type anthrax PrAg protein are provided in Table 3. The peptide bond that is cleaved within each of the sequences follows the arginine residue in the P1 position and is designated by a dash and the vertical arrow.

TABLE 3

| PrAg designation | Sequence of PrAg amino acids 164-171 ↓ P4 P3 P2 P1-P1' P2' P3' P4' | Cleavage activation sequence derivation | Predicted protease target(s) |
|---|---|---|---|
| PrAg-WT | R K K R-S T S A | wild-type PrAg | furin |
| PrAg-PCIS | F T F R-S A R L | protein C inhibitor RCL | testisin, others |
| PrAg-PAS | P Q A R-I T G G | prostasin zymogen activation site | hepsin, matriptase |
| PrAg-UAS | P R F R-I T G G | modified uPA zymogen activation site | hepsin, matriptase |
| PrAg-TAS | I P S R-I V G G | testisin zymogen activation site | unknown |

FIG. 9 provides the results from cleavage experiments on the engineered PrAg proteins using the membrane-anchored serine proteases testisin, hepsin, and matriptase. FIG. 9A indicates that each of PrAg-WT, PrAg-PAS, PrAg-PCIS and PrAg-UAS were cleaved into the active, 63 kDa form of the protein by one or more of the noted proteases. FIG. 9A provides the results from time course experiments that showed similar results, and included furin as a positive control for PrAg-WT.

Example 3

In vivo Testing

A. Establishing Orthotopic Xenograft Models of Metastatic Ovarian Cancer.

Using ovarian tumor cell lines transduced with luciferase for in vivo imaging (ES-2-luc), an i.p. orthotopic ovarian xenograft tumor model was established. Published literature indicated that $1\times10^7$ ES-2 cells injected i.p. form overwhelming tumor burden, with ascites, within two to three weeks of injection [104]. Therefore, in order to assess the in vivo i.p. growth of the ES-2-luc cells, establish an optimal cell density for cell injection, and determine whether the luciferase activity levels in the ES-2-luc cells were indeed sufficient to enable in vivo imaging, cohorts of female athymic nude mice (n=2) were injected i.p. with either $1\times10^6$, $5\times10^6$, or $1\times10^7$ ES-2-luc cells, respectively. Ovarian tumor burden was imaged using the IVIS imaging system. Mice injected with $1\times10^7$ ES-2-luc cells developed significant tumor burden in approximately 2 weeks (data not shown), as determined by IVIS imaging, and required euthanasia shortly thereafter due to tumor-induced weight gain, as well as mild cachexia and jaundice, and ascites accumulation. Mice injected with $5 \times 10^6$ ES-2-luc cells also developed significant tumor burden (data not shown), and similar symptoms, with slower onset, requiring euthanasia approximately a week later. One mouse injected with $1 \times 10^6$ ES-2-luc cells developed significant tumor burden (data not shown) after approximately 4 weeks and was euthanized due to similar symptoms, while the other mouse did not develop substantial tumor burden.

At the time of euthanizing the mice, necropsies were performed to visualize the characteristics and extent of ES-2-luc ovarian tumor growth in the peritoneal cavity. In all cases, when significant tumor burden was observed by IVIS imaging, substantial tumor burden was also observed by gross visualization. The ES-2-luc tumor cells were distributed throughout the abdominal cavity, both floating in the ascites as spheroids and attached to various organs and the body wall (data not shown). Due to the aggressive growth kinetics and tumor characteristics of the $5 \times 10^6$ ES-2-luc cell dose in female athymic nude mice, this cellular density was chosen as optimal for further experiments.

B. Establishment of a Well-tolerated Dose(s) for Mutant PrAg Toxin Treatment.

To determine a well-tolerated dose to treat i.p. xenograft ovarian tumor-bearing mice, cohorts of female athymic nude mice were injected i.p. with increasing doses of PrAg-PAS toxin (PrAg proteins combined with LF). LF was used in place of FP59 to avoid any off target effects that may be associated with non-specific uptake of the very effective protein translation inhibitor FP59 [27]. PrAg-PAS toxin was chosen for these experiments because PrAg-PAS was an engineered PrAg protein that was cleaved to an activated form by testisin, hepsin, and matriptase in vitro. Moreover, PrAg-PAS toxin was able to be activated by testisin, hepsin, and matriptase to increase ovarian tumor cell cytotoxicity. Cohorts of female athymic nude mice (n=3) received six i.p. injections of PrAg-PAS toxin over the course of two weeks. Treatment with PrAg-PAS toxin was very well-tolerated. None of the mice treated with the highest dose of PrAg-PAS toxin exhibited any apparent toxicity (data not shown). Based on these results, PrAg-PAS 45/15 (45 µg PrAg-PAS combined with 15 µLF) was identified as the maximum PrAg-PAS toxin dose for further experiments.

C. Treatment with PrAg-PAS Toxin Reduces Tumor Growth and Mmetastasis in an Orthotopic Xenograft Model of Metastatic Ovarian Cancer.

Figure 10:
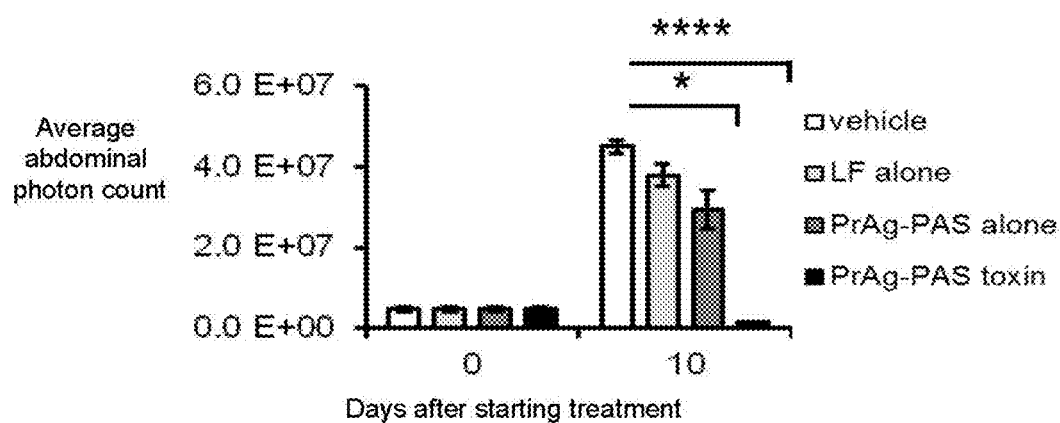
FIG. 10. Treatment with PrAg-PAS toxin reduces ovarian tumor burden. Cohorts of mice (n=5) bearing ES-2-luc i.p. xenograft tumors received four treatments of PrAg-PAS toxin (15 µg PrAg-PAS and 5 µg LF), PrAg-PAS alone (15 LF alone (5 µg), or vehicle (PBS) beginning on day 4. Tumor burden, as measured by luciferase activity levels, was monitored using the IVIS system. Ovarian tumor burden was reduced, as indicated by reduced average luciferase activity levels, in mice treated with PrAg-PAS toxin, but not in mice treated with PrAg-PAS or LF alone, relative to vehicle treated mice. Quantitative data are represented as mean values with their respective standard errors (+/−SEM). *p<0.05; ****p<0.0001.

To determine whether treatment with PrAg-PAS toxin could inhibit ovarian xenograft tumor growth and metastasis, female athymic nude mice were injected i.p. with $5 \times 10^6$ ES-2-luc ovarian tumor cells. After four days, when established tumors were visible by IVIS imaging, mice were divided into four cohorts of five mice, with all mice bearing approximately equal tumor burden. Each cohort received four i.p. injections of PrAg-PAS toxin (15 µg PrAg-PAS combined with 5 µg LF), 15 µg PrAg-PAS alone, 5 µg LF alone, or vehicle alone (PBS). During the course of the experiment, tumor growth was assessed by imaging with the IVIS system (FIG. 10). At the end of the experiment, tumor burden was assessed by performing necropsies.

The results showed that in the mice treated with vehicle alone, ES-2-luc tumor growth proceeded rapidly (FIG. 10), and resulted in the development of ascites, dissemination of small ovarian tumor nodules throughout the peritoneal space (data not shown), and mild symptoms of cachexia and jaundice. Tumor attachment was especially prevalent in high-density blood vessel areas, particularly the diaphragm, surrounding the mesentery arteries, and what appeared to be the pancreas, with some attachment to the body wall and intestinal tract (data not shown). Tumor cells also accumulated near the kidneys, genitourinary tissues, and the spleen. Moreover, accumulation of tumor cells in the vicinity of the liver seemed to result in enlargement of the gallbladder (data not shown). In some cases, vehicle treated mice that presented with symptoms of jaundice also presented with a yellow tinge of the peritoneal cavity and yellow spotting of the liver.

While tumor burden was significant and widespread in vehicle treated mice, mice treated with PrAg-PAS toxin showed significant reductions in average tumor burden over the course of the experiment (FIG. 10), as imaged with the IVIS system. Mice treated with PrAg-PAS toxin had average tumor burden that measured just 3% of the tumor burden present in vehicle-treated mice (data not shown). Tumor burden in mice treated with LF alone was not statistically different than vehicle treated mice (FIG. 10). Mice treated with PrAg-PAS alone had average tumor burden that measured 65% of the tumor burden present in vehicle treated mice (FIG. 10).

Mice treated with PrAg-PAS toxin also showed drastically less tumor burden at the time of euthanasia and performance of necropsies (data not shown). PrAg-PAS toxin-treated mice did not develop ascites, did not present with ovarian tumor cells covering the diaphragm or the tissue surrounding the mesentery arteries, and did not present with any symptoms of cachexia or jaundice (data not shown). Moreover, PrAg-PAS toxin-treated mice did not have tumor nodules abundant on the body cavity wall, tumor nodules spread throughout the abdominal cavity, or swollen gallbladders. While mice receiving PrAg-PAS alone had reductions in tumor burden over the course of the experiment (FIG. 10), relative to the mice treated with vehicle alone, upon performing necropsies the tumor burdens of mice treated with PrAg-PAS or LF alone was still widespread, and largely resembled that in the mice treated with vehicle. The PrAg-PAS or LF alone treated mice presented with similar tumor distribution, development of ascites, and mild symptoms of cachexia and jaundice.

As observed when establishing a tolerated dose, all treatments of PrAg-PAS toxin, or the components alone, were well tolerated. Mice experienced no treatment specific weight loss, symptoms, or gross organ damage as visualized upon performing necropsies. The substantial decrease in tumor burden (by IVIS and necropsy) in mice treated with PrAg-PAS toxin indicated that PrAg-PAS toxin was very effective in reducing ovarian tumor burden and metastasis in vivo in this model. Additionally, the data indicated that the mechanism of effective ovarian tumor killing by PrAg-PAS toxin requires the co-administration of both PrAg-PAS and LF, and is not due to the action of either component in the absence of the other.

D. Treatment with PrAg-PAS Toxin Reduces Established Ovarian Tumor Burden.

Figure 11:
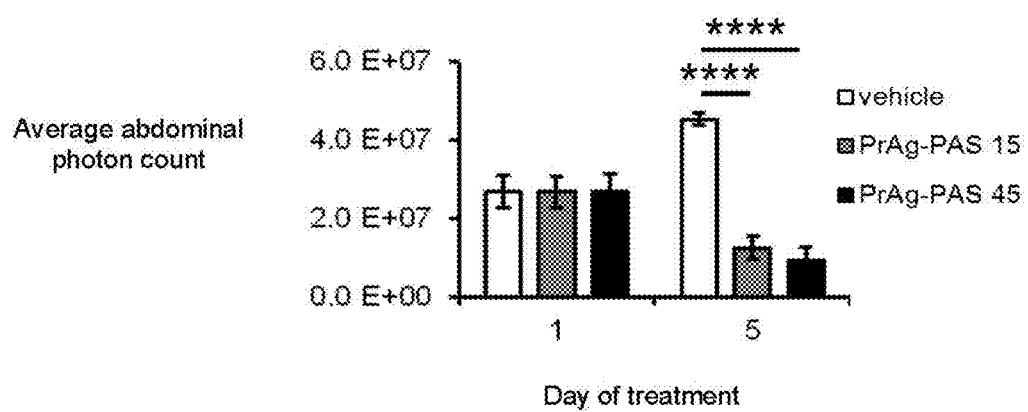
FIG. 11. Treatment with PrAg-PAS toxin reduces advanced-stage ovarian tumor burden. Cohorts of mice (n=5) bearing ES-2-luc i.p. xenograft tumors received two treatments of PrAg-PAS toxin (15 µg or 45 µg PrAg-PAS and 5 µg or 15 µg LF, respectively) or vehicle (PBS) beginning on day 10. Tumor burden, as measured by luciferase activity levels, was monitored using the IVIS system. Ovarian tumor burden was reduced, as indicated by reduced average luciferase activity levels, in mice treated with both doses of PrAg-PAS toxin, relative to vehicle treated mice. Quantitative data are represented as mean values with their respective standard errors (+/−SEM). ****p<0.0001.

To determine whether treatment with PrAg-PAS toxin could reduce established ovarian tumor burden, rather than early ovarian tumor growth (treatment beginning on day 4 after ES-2-luc tumor cell injection), female athymic nude mice were injected i.p. with $5 \times 10^6$ ES-2-luc ovarian tumor cells. After ten days, when significant tumor burden was present, mice were divided into three cohorts of five mice, with all mice bearing approximately equal tumor burden. Each cohort received two i.p. injections of either of two different doses of PrAg-PAS toxin (45 µg PrAg-PAS, 15 µg PrAg-PAS, and 15 µg LF, or 5 µg LF, respectively), or vehicle (PBS). During the course of the experiment, tumor growth was assessed by imaging with the IVIS system (FIG. 11). At the end of the experiment, tumor burden was assessed by performing necropsies.

The results showed that in the mice treated with vehicle alone, ES-2-luc tumor growth proceeded rapidly (FIG. 11), resulting in the development of ascites and the spread of ovarian tumor burden within the peritoneal space (data not shown). Tumor attachment was especially prevalent in high-density blood vessel areas, such as the diaphragm, the mesenteric arteries, what appeared to be the pancreas, and the body wall. Tumor cells also accumulated near the kidneys, genitourinary tissues, and the spleen. While tumor burden was significant and widespread in vehicle-treated mice, mice treated with the two different doses of PrAg-PAS toxin showed significant reductions in average tumor burden over the course of the experiment (FIG. 11), as imaged with the IVIS system. Mice treated with the lowest dose of PrAg-PAS toxin (15 µg PrAg-PAS and 5 µg LF) had average tumor burden that measured approximately 28% of the tumor burden present in vehicle treated mice (FIG. 11). Tumor burden in mice treated with the highest dose of PrAg-PAS toxin (45 µg PrAg-PAS and 15 µg LF) had an average tumor burden that measured approximately 20% of the tumor burden present in vehicle treated mice (FIG. 11).

Mice treated with the two different doses of PrAg-PAS toxin also showed less tumor burden at the time of euthanasia and performance of necropsies (data not shown). PrAg-PAS toxin-treated mice presented with reduced tumor burden specifically covering the tissue surrounding the mesenteric arteries. Tumor burden was also reduced on the body wall and the diaphragm. As observed when establishing a tolerated dose, all treatments of PrAg-PAS toxin, were well tolerated. The decrease in tumor burden (by IVIS and necropsy) in mice treated with the two different doses of PrAg-PAS toxin indicated that PrAg-PAS toxin was able to reduce established tumor burden, in addition to reducing early stage tumor burden.

E. Anti-ovarian Tumor Effect of Mutant PrAg-PAS Toxin is Dependent Upon Proteolytic Activation.

To determine whether the anti-tumor mechanism of PrAg-PAS toxin requires its proteolytic activation, cohorts of female athymic nude mice bearing approximately equal ES-2-luc xenograft ovarian tumor burden received six i.p. treatments of PrAg-PAS toxin, vehicle (PBS), or an un-activatable PrAg toxin, termed PrAg-U7, in which the amino acid sequence that functions as the cleavage site mediating activation of PrAg-PAS was replaced with the amino acid sequence PGG [15]. The replacement with the PGG amino acid sequence renders PrAg-U7 unable to be proteolytically cleaved and activated and therefore unable to oligomerize and ultimately deliver proteins (LF, EF, FP59) into the cytosol to cause cell death. A cohort of mice was also treated with a mutant PrAg toxin that requires activation by both uPA and MMP2/9, termed PrAg-IC (intercomplementing toxin), which contains the same activation sequences as the PrAg-L1 and PrAg-U2 engineered toxins. PrAg-IC had not previously been tested for anti-ovarian tumor efficacy, but had been shown to be efficacious in reducing tumor burden in multiple other tumor models [20, 27]. PrAg-IC was used to assess the relative effectiveness of PrAg-PAS toxin in reducing ovarian tumor burden, and to investigate whether PrAg-PAS toxin was more efficacious in reducing ovarian tumor burden than PrAg-IC toxin.

Figure 12C:
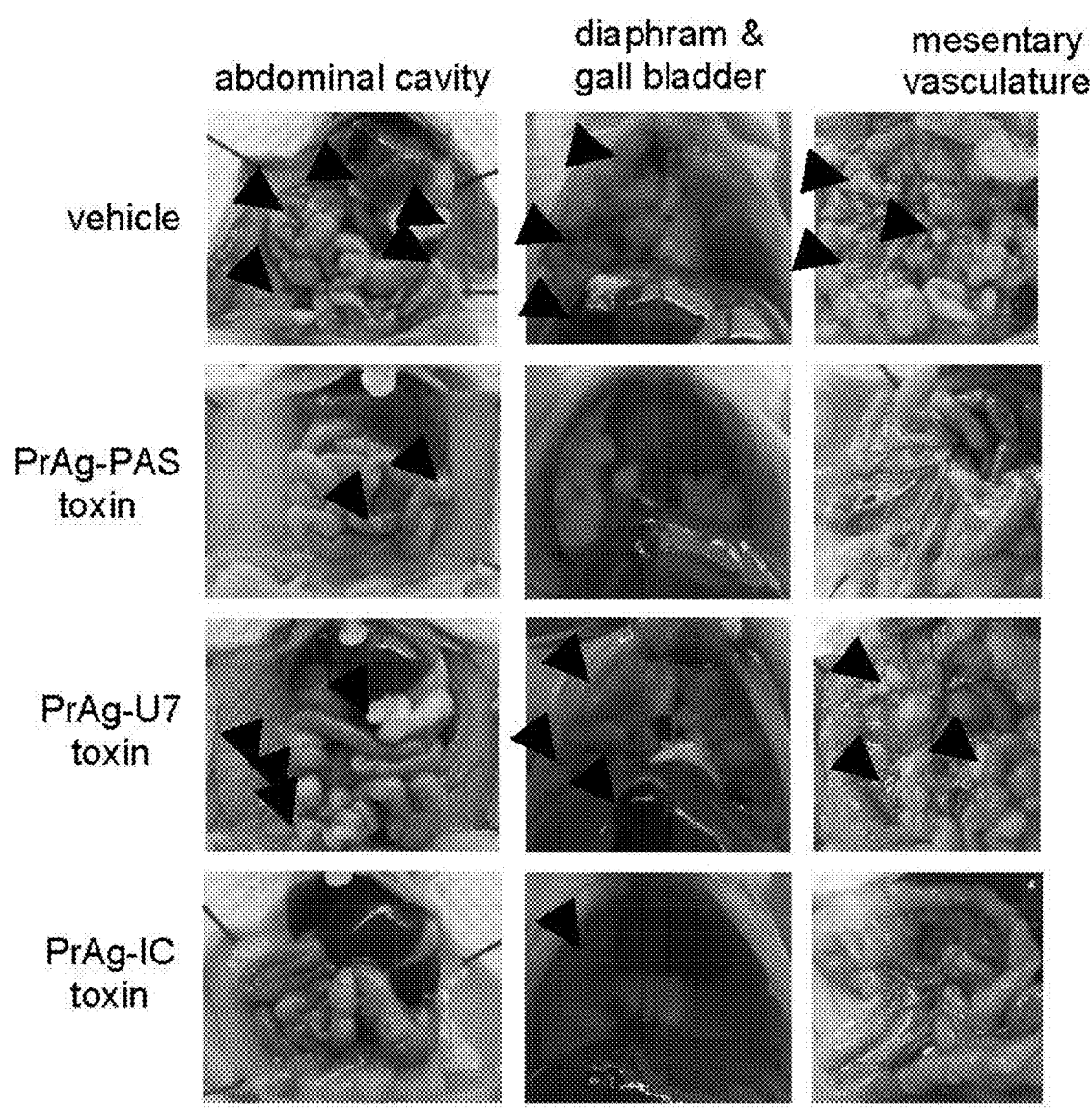

Treatment with PrAg-PAS toxin significantly reduced the average tumor burden of the ES-2-luc tumor-bearing mice, relative to cohorts treated with vehicle (FIGS. 12A,B). Mice treated with PrAg-PAS toxin possessed only 15% of the tumor burden of vehicle-treated mice on day 4, and 2.6% of the tumor burden in vehicle-treated mice on day 9 (FIG. 12A). Notably, mice treated with PrAg-IC toxin also displayed significant reductions in tumor burden that were approximately equal to those seen in PrAg-PAS toxin-treated mice, relative to vehicle-treated mice (FIGS. 12A,B). Mice treated with PrAg-IC toxin possessed 8% the tumor burden of vehicle-treated mice on day 4, and 4% of the tumor burden in vehicle-treated mice on day 9 (FIG. 12A). Mice treated with the un-activatable PrAg-U7 toxin experienced no reductions in tumor burden relative to vehicle-treated mice (FIGS. 12A,B), and developed significant tumor burden, as well as the symptoms of cachexia and jaundice, as noticed previously.

When the mice were euthanized and necropsies were performed, mice treated with PrAg-PAS toxin or PrAg-IC toxin had substantially less tumor burden within the peritoneal cavity than did mice treated with vehicle or PrAg-U7 toxin (data not shown). PrAg-PAS toxin-and PrAg-IC toxin-treated animals possessed few, if any, tumors attached to the diaphragm, wall of the peritoneal cavity, tissue surrounding the mesentery arteries, intestinal tract, or surrounding the major organs. Vehicle- and PrAg-U7 toxin-treated mice had significant tumor accumulation and tumor attachment to these areas. Mice in the vehicle- and PrAg-U7 toxin-treated cohorts also presented with enlarged gall bladders, whereas this was not seen in mice treated with PrAg-PAS toxin or PrAg-IC toxin. As before, all toxin treatments were well tolerated. Mice displayed no treatment-specific weight loss, outward signs of toxicity, or gross organ damage due to treatment with the toxins.

These data demonstrate that proteolytic activation of the PrAg-PAS toxin is required for its anti-ovarian tumor effect, and suggest that in the absence of proteolytic activation, the mutant PrAg toxins are relatively inactive. These data also suggest that PrAg-IC toxin, not previously demonstrated to be effective at treating preclinical models of ovarian cancer, also requires proteolytic activation, and is effective at reducing i.p. ovarian tumor burden and metastasis in this mouse model.

Example 4

Human Cells

Human Ovarian Tumor Cell Lines Possess Cell-surface Trypsin-like Serine Protease Activity.

Figure 13A:
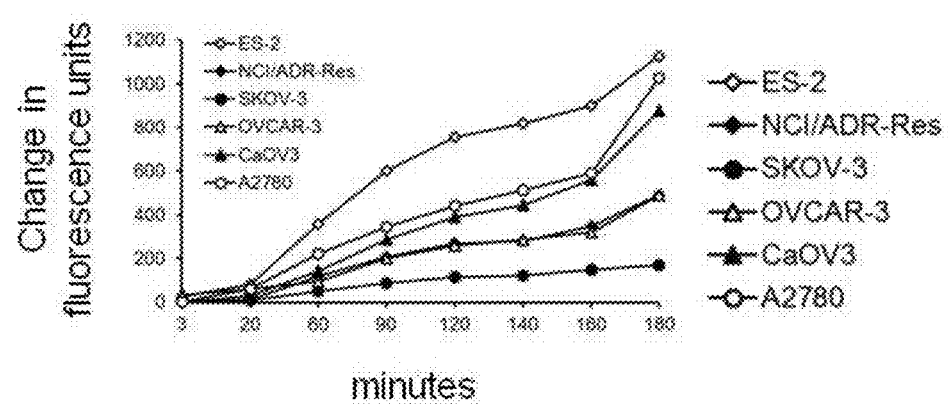
FIG. 13A-13B. Ovarian tumor cell lines possess cell-surface serine protease activity. Ovarian tumor cell lines were incubated with a fluorogenic peptide, Boc-QAR-AMC, in the presence or absence of the serine protease inhibitor AEBSF to investigate whether they possess cell-surface serine protease activity capable of activating the mutant PrAg toxins. Fluorescence values for the peptide in the absence of cells were subtracted from the change in fluorescence units due to serine protease-mediated cleavage of the peptide in presence of the cells (with and without AEBSF).
Figure 13B:
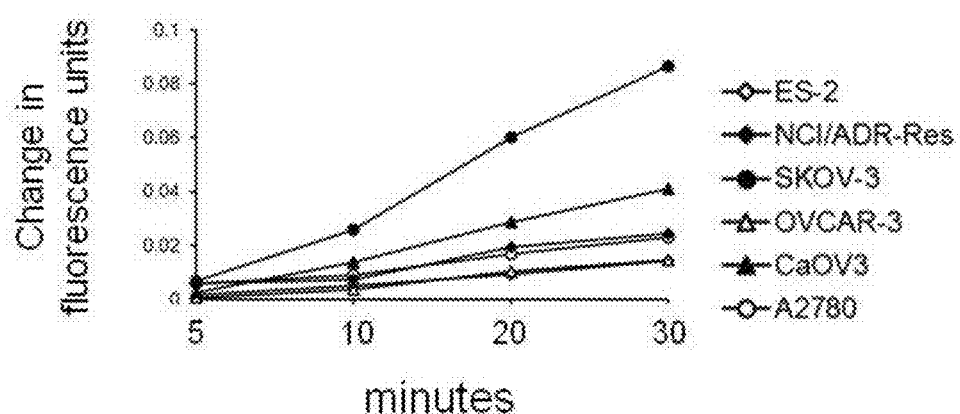

To investigate the expression of cell-surface serine protease activities that might be capable of activating the mutant PrAg toxins, ovarian tumor cell lines were incubated with a fluorogenic peptide that functions as a substrate for membrane-anchored serine proteases. In the presence or absence of the serine protease inhibitor AEBSF, cleavage of the peptide by each of the tumor cell lines resulted in an AEBSF-sensitive increase in fluorescent signal intensity, indicating that each of the tumor cells possessed serine proteases capable of cleaving the peptide (FIGS. 13A,13B). Cleavage of the peptide at two different cell confluencies (~40% and ~90%) suggested that all of these tumor cell lines possessed active cell-surface serine proteases potentially capable of activating the mutant PrAg toxins, but that the proteases are regulated differently depending on the cellular confluence.

Example 5

PrAg-PAS Toxin Treatment Extends Survival in a Murine Xenograft Tumor Model.

Based on the results indicating that PrAg-PAS toxin could significantly reduce i.p. xenograft ovarian tumor burden, it was determined whether the PrAg-PAS toxin-mediated reductions in tumor burden could translate into an extension of mouse survival, and if so whether this activity could exhibit dose-dependence. Therefore, female athymic nude mice injected i.p. with ES-2-luc tumor cells, upon tumor development, were divided into cohorts of equal average tumor burden. The cohorts of mice then received nine i.p. injections composed of different doses of PrAg-PAS toxin (45 µg, 15 µg, or 6 µg PrAg-PAS, in combination with 15 µg, 5 µg, or 2 µg LF, respectively) or vehicle (PBS). Mice were euthanized when they exhibited substantial weight gain (>10%), were moribund, or exhibited other signs of significant malaise and/or distress due to tumor burden. An increase in body weight of >10% was chosen as the primary endpoint in the absence of health conditions caused by tumor burden because it is typical weight gain suggestive of excess tumor burden in the relevant literature.

Figure 14:
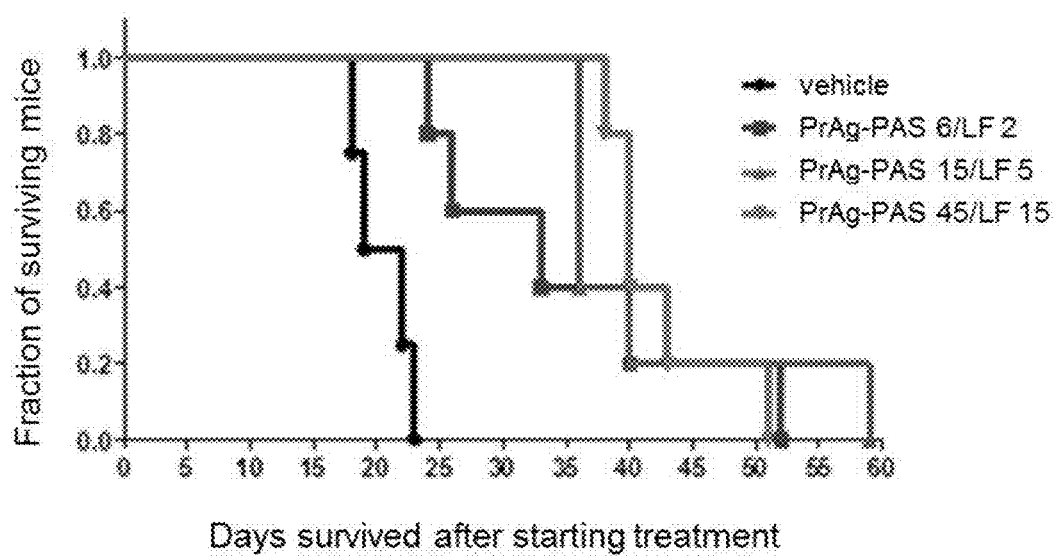
FIG. 14. Treatment with PrAg-PAS toxin extends survival. Cohorts of mice bearing ES-2-luc i.p. xenograft tumors received nine treatments of three different concentrations of PrAg-PAS toxin (45 µg, 15 µg, 6 µg PrAg-PAS and 15 µg, 5 µg, 2 µg LF, respectively), or vehicle (PBS). Tumor burden, as measured by luciferase activity levels, was monitored using the IVIS system (not shown). Treatment with each dose of PrAg-PAS toxin significantly extended survival, relative to vehicle treated mice. Vehicle n=4, PrAg toxin-treated cohorts n=5. *p value of<0.008.

Tumor-bearing mice treated with either of the two highest doses of PrAg-PAS toxin (15 µg or 45 µg of PrAg-PAS, combined with 5 µg or 15 µg of LF, respectively) exhibited significant 2.04-fold and 2.06-fold increases in survival over the course of the experiment, relative to mice treated with vehicle (FIG. 14). Tumor-bearing mice treated with the lowest dose of PrAg-PAS toxin (6 µg PrAg-PAS combined with 2 µg LF) exhibited a significant 1.7-fold increase in survival, relative to mice treated with vehicle (FIG. 14). Upon euthanasia, necropsies were performed. Mice treated with vehicle, as expected, had substantial tumor burden, with tumor distributions similar to those seen previously. At the time of euthanasia, the majority of mice that were treated with the different doses of PrAg-PAS toxin had a recurrence of tumor burden that upon performing necropsies appeared similar that seen in the vehicle-treated mice. Yet, some of the mice did not experience widespread tumors, but rather presented with tumor aggregation only surrounding the liver and adjacent to the spleen, relative to mice treated with vehicle (not shown). The toxin doses were well tolerated by the mice. These data demonstrated a significant, dose-dependent effect of PrAg-PAS toxin treatment in extending survival in a xenograft model of metastatic ovarian cancer.

Example 6

Human Ovarian Tumor Cell Lines are Susceptible to Killing by the Mutant PrAg Toxins.

Figures 15A, 15B, 15C, 15D, 15E, 15F:
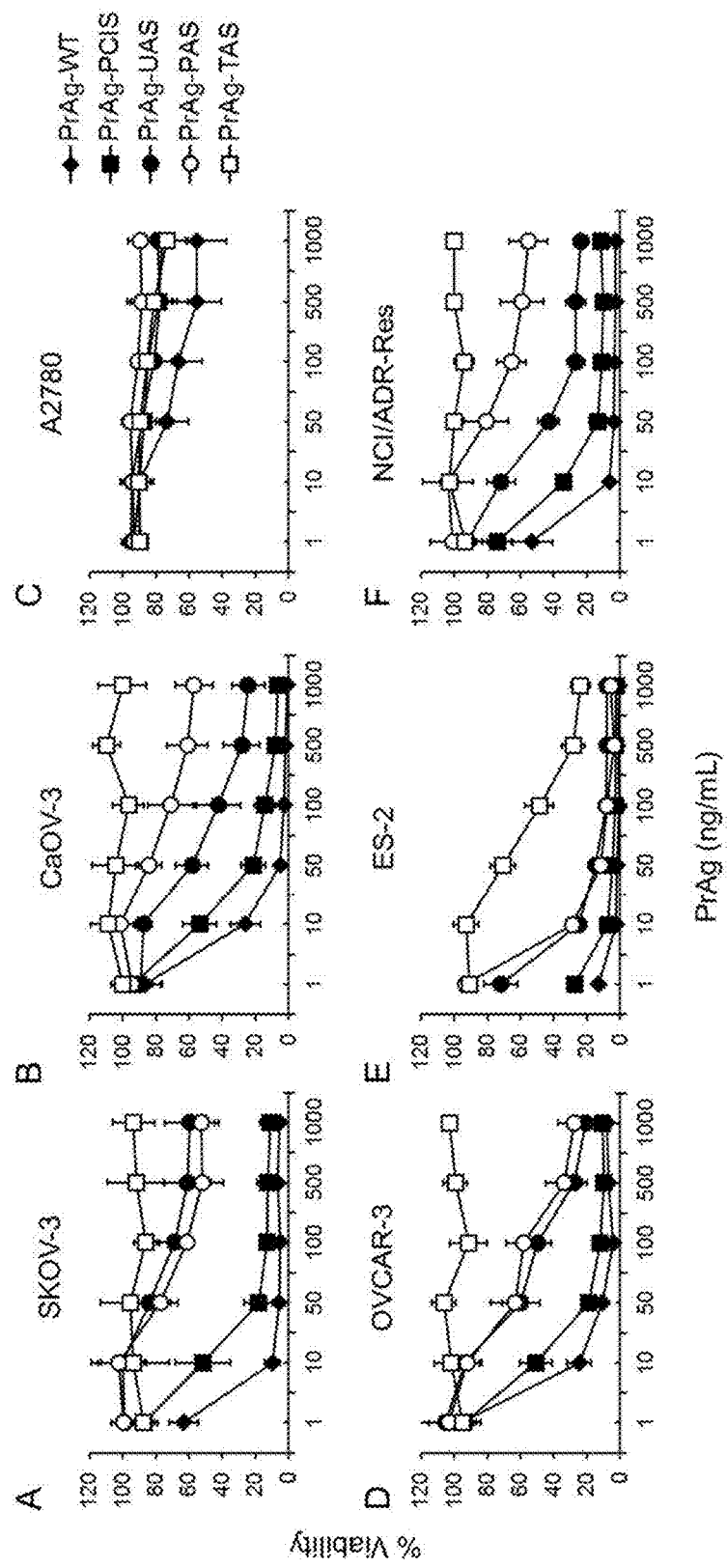
FIGS. 15A-15G. The mutant PrAg toxins induce human ovarian tumor cell cytotoxicity. The human ovarian tumor cell lines FIG. 15A) SKOV-3, FIG. 15B) CaOV-3, FIG. 15C) A2780, FIG. 15D) OVCAR-3, FIG. 15E) ES-2, and FIG. 15F) NCI/ADR-Res were incubated with 0-1000 ng/mL of PrAg-WT, PrAg-PCIS, PrAg-PAS, PrAg-UAS, or PrAg-TAS and FP59 (50 ng/mL) for 48 hours and cell viability was assayed by MTT assay. MTT assays represent the mean of three experiments performed in triplicate. Quantitative data are represented as mean values with their respective standard errors (+/−SEM).
Figure 15G:
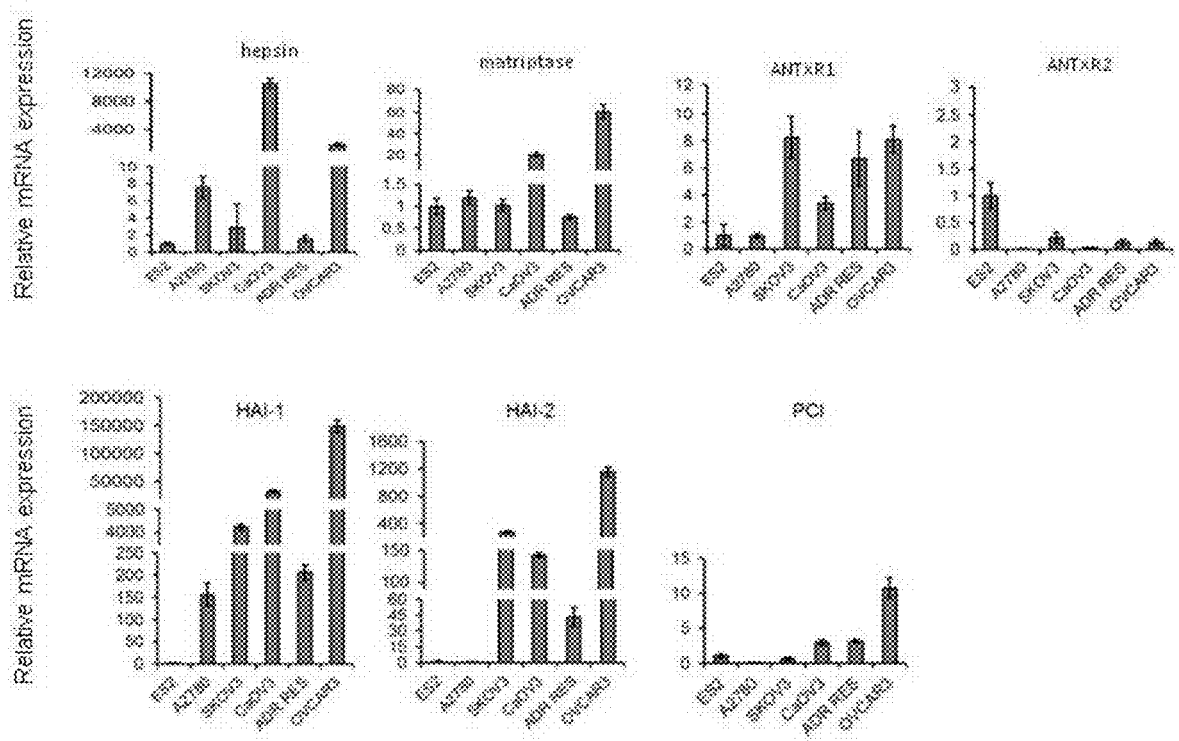

To test the efficacy of the toxins to kill a range of human ovarian cell lines including ADR-Res, OvCAR3, and SKOV3 which are resistant to clinically relevant concentrations of cisplatinin (typical of recurrent ovarian cancers), cell lines were treated with the mutant PrAg toxins and MTT cytotoxicity assays were performed (FIGS. 15A-F). The ovarian tumor cell lines were also incubated with PrAg-WT toxin as a positive control (FIGS. 15A-F). Each of the ovarian tumor cell lines, except A2780, showed a dose-dependent susceptibility to killing by the mutant PrAg toxins (PrAg-PAS, PrAg-UAS, PrAg-PCIS), as well as the PrAg-WT toxin (FIGS. 15A-F). The majority of the cell lines were not susceptible to PrAg-TAS. The ES-2 cells were sensitive to high doses of the PrAg-TAS toxin (FIG. 15D). Of the mutant PrAg toxins, PrAg-PCIS toxin induced the most cytotoxicity in the ovarian tumor cell lines (FIGS. 15A-F). PrAg-PAS toxin and PrAg-UAS toxin appeared to be equally effective at inducing cell death in the majority of the ovarian tumor cell lines (FIGS. 15A-F). Yet, PrAg-UAS toxin was more effective than PrAg-PAS toxin at inducing cell death in NCI/ADR-Res and CaOV-3 cells (FIGS. 15A-F). The A2780 tumor cell line exhibited little to no susceptibility to killing by the mutant PrAg toxins (FIG. 15F). PrAg-WT toxin was the most effective at inducing cytotoxicity in all of the ovarian tumor cell lines, except A2780 (FIGS. 15A-F). since this line expresses anthrax toxin receptors, it is likely that the killing pathway targeted by the cargo, FP59 is not functional in this tumor line. All of these ovarian tumor cell lines also exhibit varying expression levels of proteases and the anthrax toxin receptors (FIG. 15G), required for toxin killing. All together, these findings show that many if not all ovarian tumor cell lines are susceptible to killing by the mutant PrAg toxins.

Example 7

Cisplatin Resistant Ovarian Tumor Cells are Killed by Engineered Anthrax Toxins.

Figures 16A, 16B:
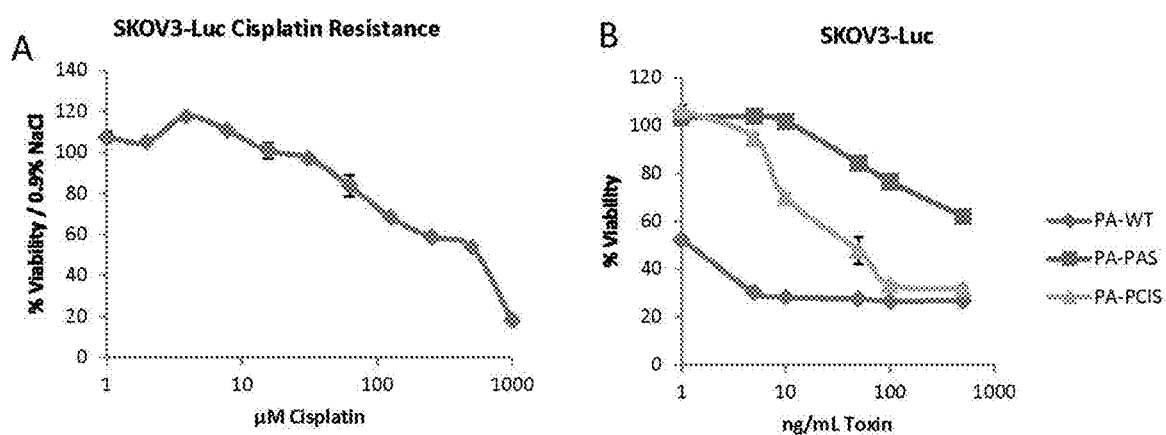
FIGS. 16A-16B. To determine their level of resistance to cisplatin treatment, the luciferase expressing ovarian cancer cell line SKOV3-Luc was treated for 24 hours with varying doses of cisplatin (1-1000 µM). IC50 for the cell was calculated to be 230.4 µM by a non-linear regression best fit model (FIG. 16A). To test if the engineered anthrax toxins would be able to kill the cisplatin resistant cell line SKOV3-Luc cells were incubated with engineered anthrax toxins (0-500 ng/mL) and FP59 (50 ng/mL) for 48 hours after which cell viability was evaluated by MTT assay. Values are the means calculated from one independent experiment performed in triplicate (FIG. 16B).

To confirm the resistance of SKOV-3 cells to cisplatin, SKOV3-Luc ovarian tumor cells (SKOV3 cells expressing luciferase) were treated with varying doses of cisplatin (1-1000 µM) for 24 hrs and the IC50 calculated using a non-linear regression best fit model (FIG. 16A). An IC50 greater than 100 µM is generally considered chemoresistant. The measured IC50 of 230.4 µM for the SKOV3-Luc ovarian tumor cells demonstrates their resistance to platinin chemotherapy. When the SKOV3-Luc was treated with the mutant PrAg toxins it showed dose-dependent susceptibility to PA-PAS and PA-PCIS demonstrating that mutant engineered anthrax toxins are effective against established, chemotherapy resistant ovarian cancers (FIG. 16B).

Example 8

Treatment with PrAg-PAS Toxin Reduces NCl/ADR-Res-Luc ovarian tumor burden.

Figure 17:
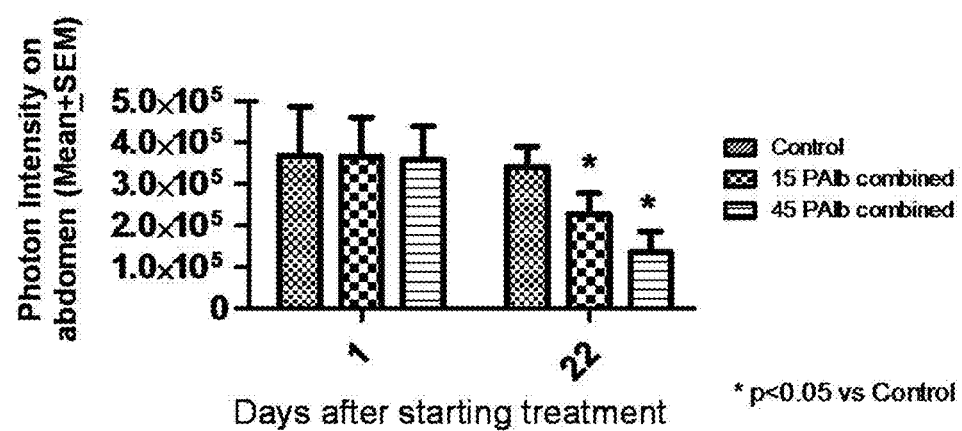
FIG. 17. Treatment with PrAg-PAS toxin reduces ovarian tumor burden in NCI/ADR-Res-Luc xenograft model. Cohorts of mice (n=5) bearing 29 day old NCI/ADR-Res-Luc i.p. xenograft tumors received 6 treatments of PrAg-PAS toxin (15 µg or 45 µg PrAg-PAS and 5 µg or 15 µg LF, respectively) or vehicle (PBS). Tumor burden, as measured by luciferase activity levels, was monitored using the IVIS system. Ovarian tumor burden was reduced, as indicated by reduced average luciferase activity levels, in mice treated with both doses of PrAg-PAS toxin, relative to vehicle treated mice. Quantitative data are represented as mean values with their respective standard errors (+/−SEM). *p<0.05.

To test the in vivo efficacy of the PrAg-PAS toxin to kill platinin-resistant cell line ADR-Res, cohorts of female athymic nude mice were injected with $1.5 \times 10^7$ NCl/ADR-Res-Luc ovarian tumor cells and the tumor allowed to grow for 29 days. This tumor is slower growing that the ES-2-luc cells. Cohorts of mice bearing tumors received 6 injections, 3 per week x 2 weeks (day 1, 4, 6, 8, 11, and 13) of i.p. treatments with PrAg-PAS toxin (15 ug), PrAg-PAS toxin (45 ug), or vehicle alone (FP59 control), starting at day 1. Tumors were imaged 6 days later at day 22. Treatment with PrAg-PAS toxin significantly reduced the average tumor burden of the NCl/ADR-Res-Luc tumor-bearing mice, relative to control cohorts treated with vehicle, at both doses tested (FIG. 17). showing the in vivo efficacy of the toxin treatments in a different ovarian tumor cell line.

Example 9

Human Pancreatic Cancer Cell Lines are Susceptible to Engineered Mutant Anthrax Toxins.

To test the efficacy of the toxins to kill human pancreatic cancer lines were treated with the toxins and viability measured by MTT cytotoxicity assays. Pancreatic cancer cell lines were incubated with engineered anthrax toxins (0-500 ng/mL) and FP59 (50 ng/mL) for 48 hours after which cell viability was evaluated by MTT assay. Each of the pancreatic tumor cell lines showed a dose-dependent susceptibility to killing by the mutant PrAg toxins (PrAg-PAS, PrAg-UAS, PrAg-PCIS or the PrAg-WT toxin (data not shown). These results show that pancreatic tumor cell lines are susceptible to killing by the mutant PrAg toxins.

Example 10

Human Lung Tumors are Susceptible to Killing by the Mutant PrAg Toxins.

To test the efficacy of the mutant toxins to kill lung tumors, the A549 human lung cancer line was treated with each of the toxins and viability measured by MTT cytotoxicity assay. The lung cancer cell line A549 was incubated with engineered anthrax toxins (0-500 ng/mL) and FP59 (50 ng/mL) for 48 hours after which cell viability was evaluated by MTT assay. The lung tumor line showed a dose-dependent susceptibility to killing by all of the mutant PrAg toxins (data not shown). These data show that lung tumors, which exhibit varying expression levels of proteases and the anthrax toxin receptors are likely to be susceptible to killing by the mutant PrAg toxins.

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Sevenich L, Joyce J A. Pericellular proteolysis in cancer. Genes Dev. 2014. 28:2331-2347.
2. Choi K Y, Swierczewska M, Lee S, Chen X. Protease-activated drug development. Theranostics. 2012. 2:156-178.
3. Weidle U H, Tiefenthaler G, Schiller C, Weiss E H, Georges G, Brinkmann U. Prospects of bacterial and plant protein-based immunotoxins for treatment of cancer. Cancer Genomics Proteomics. 2014. 11:25-38.
4. Turk B. Targeting proteases: successes, failures and future prospects. Nat. Rev. Drug Discov. 2006. 5:785-799.
5. Weidle U H, Tiefenthaler G, Georges G. Proteases as activators for cytotoxic prodrugs in antitumor therapy. Cancer Genomics Proteomics. 2014. 11:67-79.
6. Liu S, Zhang Y, Moayeri M, Liu J, Crown D, Fattah R J, Wein A N, Yu Z X, Finkel T, Leppla S H. Key tissue targets responsible for anthrax-toxin-induced lethality. Nature 2013. 501:63-68.
7. Liu S, Moayeri M, Leppla S H. Anthrax lethal and edema toxins in anthrax pathogenesis. Trends Microbiol. 2014. 22:317-325.
8. Hobson J P, Liu S, Rono B, Leppla S H, Bugge T H. Imaging specific cell-surface proteolytic activity in single living cells. Nat. Methods 2006. 3:259-261.
9. Hobson J P, Liu S, Leppla S H, Bugge T H. Imaging specific cell surface protease activity in living cells using reengineered bacterial cytotoxins. Methods Mol. Biol. 2009. 539:115-129.
10. Leppla S H, Arora N, Varughese M. Anthrax toxin fusion proteins for intracellular delivery of macromolecules. J. Appl. Microbiol. 1999. 87:284
11. Bachran C, Hasikova R, Leysath C E, Sastalla I, Zhang Y, Fattah R J, Liu S, Leppla S H. Cytolethal distending toxin B as a cell-killing component of tumor-targeted anthrax toxin fusion proteins. Cell Death. Dis. 2014. 5:e1003
12. Bachran C, Morley T, Abdelazim S, Fattah R J, Liu S, Leppla S H. Anthrax toxin-mediated delivery of the Pseudomonas exotoxin A enzymatic domain to the cytosol of tumor cells via cleavable ubiquitin fusions. MBio. 2013. 4:e00201-e00213.
13. Liao X, Rabideau A E, Pentelute B L. Delivery of antibody mimics into mammalian cells via anthrax toxin protective antigen. Chembiochem. 2014. 15:2458-2466.
14. Verdurmen W P, Luginbuhl M, Honegger A, Pluckthun A. Efficient cell-specific uptake of binding proteins into the cytoplasm through engineered modular transport systems. J. Control Release 2015. 200:13-22.
15. Liu S, Bugge T H, Leppla S H. Targeting of tumor cells by cell surface urokinase plasminogen activator-dependent anthrax toxin. J. Biol. Chem. 2001. 276:17976-17984.
16. Liu S, Netzel-Arnett S, Birkedal-Hansen H, Leppla S H. Tumor cell-selective cytotoxicity of matrix metalloproteinase-activated anthrax toxin. Cancer Res. 2000. 60:6061-6067.
17. Abi-Habib R J, Singh R, Liu S, Bugge T H, Leppla S H, Frankel A E. A urokinase-activated recombinant anthrax toxin is selectively cytotoxic to many human tumor cell types. Mol. Cancer Ther. 2006. 5:2556-2562.
18. Liu S, Aaronson H, Mitola D J, Leppla S H, Bugge T H. Potent antitumor activity of a urokinase-activated engineered anthrax toxin. Proc. Natl. Acad. Sci. U.S.A 2003. 100:657-662.
19. Alfano R W, Leppla S H, Liu S, Bugge T H, Ortiz J M, Lairmore T C, Duesbery N S, Mitchell I C, Nwariaku F, Frankel A E. Inhibition of tumor angiogenesis by the matrix metalloproteinase-activated anthrax lethal toxin in an orthotopic model of anaplastic thyroid carcinoma. Mol. Cancer Ther. 2010. 9:190-201.
20. Schafer J M, Peters D E, Morley T, Liu S, Molinolo A A, Leppla S H, Bugge T H. Efficient targeting of head and neck squamous cell carcinoma by systemic administration of a dual uPA and MMP-activated engineered anthrax toxin. PLoS. One. 2011. 6:e20532
21. Liu S, Wang H, Currie B M, Molinolo A, Leung H J, Moayeri M, Basile J R, Alfano R W, Gutkind J S, Frankel A E, Bugge T H, Leppla S H. Matrix metalloproteinase-activated anthrax lethal toxin demonstrates high potency in targeting tumor vasculature. J. Biol. Chem. 2008. 283:529-540.
22. Phillips D D, Fattah R J, Crown D, Zhang Y, Liu S, Moayeri M, Fischer E R, Hansen B T, Ghirlando R, Nestorovich E M, Wein A N, Simons L, Leppla S H et al. Engineering anthrax toxin variants that exclusively form octamers and their application to targeting tumors. J. Biol. Chem. 2013. 288:9058-9065.
23. Abi-Habib R J, Singh R, Leppla S H, Greene J J, Ding Y, Berghuis B, Duesbery N S, Frankel A E. Systemic anthrax lethal toxin therapy produces regressions of subcutaneous human melanoma tumors in athymic nude mice. Clin. Cancer Res. 2006. 12:7437-7443.
24. Alfano R W, Leppla S H, Liu S, Bugge T H, Duesbery N S, Frankel A E. Potent inhibition of tumor angiogenesis by the matrix metalloproteinase-activated anthrax lethal toxin: implications for broad anti-tumor efficacy. Cell Cycle 2008. 7:745-749.

25. Chen K H, Liu S, Bankston L A, Liddington R C, Leppla S H. Selection of anthrax toxin protective antigen variants that discriminate between the cellular receptors TEM8 and CMG2 and achieve targeting of tumor cells. J. Biol. Chem. 2007. 282:9834-9845.

26. Wein A N, Liu S, Zhang Y, McKenzie A T, Leppla S H. Tumor therapy with a urokinase plasminogen activator-activated anthrax lethal toxin alone and in combination with paclitaxel. Invest New Drugs 2013. 31:206-212.

27. Peters D E, Hoover B, Cloud L G, Liu S, Molinolo A A, Leppla S H, Bugge T H. Comparative toxicity and efficacy of engineered anthrax lethal toxin variants with broad anti-tumor activities. Toxicol. Appl. Pharmacol. 2014. 279:220-229.

28. Coussens L M, Fingleton B, Matrisian L M. Matrix metalloproteinase inhibitors and cancer: trials and tribulations. Science 2002. 295:2387-2392.

29. Hooper J D, Clements J A, Quigley J P, Antalis T M. Type II transmembrane serine proteases. Insights into an emerging class of cell surface proteolytic enzymes. J. Biol. Chem. 2001. 276:857-860.

30. Antalis T M, Bugge T H, Wu Q. Membrane-anchored serine proteases in health and disease. Prog. Mol. Biol. Transl. Sci. 2011. 99:1-50.

31. Viloria C G, Peinado J R, Astudillo A, Garcia-Suarez O, Gonzalez M V, Suarez C, Cal S. Human DESC1 serine protease confers tumorigenic properties to MDCK cells and it is upregulated in tumours of different origin. Br. J. Cancer 2007. 97:201-209.

32. Szabo R, Rasmussen A L, Moyer A B, Kosa P, Schafer J M, Molinolo A A, Gutkind J S, Bugge T H. c-Met-induced epithelial carcinogenesis is initiated by the serine protease matriptase. Oncogene 2011. 30:2003-2016.

33. Wu S R, Cheng T S, Chen W C, Shyu H Y, Ko C J, Huang H P, Teng C H, Lin C H, Johnson M D, Lin C Y, Lee M S. Matriptase is involved in ErbB-2-induced prostate cancer cell invasion. Am. J. Pathol. 2010. 177: 3145-3158.

34. Kim S, Kang H Y, Nam E H, Choi M S, Zhao X F, Hong C S, Lee J W, Lee J H, Park Y K. TMPRSS4 induces invasion and epithelial-mesenchymal transition through upregulation of integrin alpha5 and its signaling pathways. Carcinogenesis 2010. 31:597-606.

35. Chen Y W, Lee M S, Lucht A, Chou F P, Huang W, Havighurst T C, Kim K, Wang J K, Antalis T M, Johnson M D, Lin C Y. TMPRSS2, a serine protease expressed in the prostate on the apical surface of luminal epithelial cells and released into semen in prostasomes, is misregulated in prostate cancer cells. Am. J. Pathol. 2010. 176: 2986-2996.

36. Tanimoto H, Shigemasa K, Tian X, Gu L, Beard J B, Sawasaki T, O'Brien T J. Transmembrane serine protease TADG-15 (ST14/Matriptase/MT-SP1): expression and prognostic value in ovarian cancer. Br. J. Cancer 2005. 92:278-283.

37. Wu Q, Parry G. Hepsin and prostate cancer. Front Biosci. 2007. 12:5052-5059.

38. Santin A D, Cane'S, Bellone S, Bignotti E, Palmieri M, Las Casas L E, Anfossi S, Roman J J, O'Brien T, Pecorelli S. The novel serine protease tumor-associated differentially expressed gene-15 (matriptase/MT-SP1) is highly overexpressed in cervical carcinoma. Cancer 2003. 98:1898-1904.

39. Miao J, Mu D, Ergel B, Singavarapu R, Duan Z, Powers S, Oliva E, Orsulic S. Hepsin colocalizes with desmosomes and induces progression of ovarian cancer in a mouse model. Int. J. Cancer 2008. 123:2041-2047.

40. Wu F, Wu Q. Corin-mediated processing of pro-atrial natriuretic peptide in human small cell lung cancer cells. Cancer Res. 2003. 63:8318-8322.

41. Wallrapp C, Hahnel S, Muller-Pillasch F, Burghardt B, Iwamura T, Ruthenburger M, Lerch M M, Adler G, Gress T M. A novel transmembrane serine protease (TMPRSS3) overexpressed in pancreatic cancer. Cancer Res. 2000. 60:2602-2606.

42. Vaarala M H, Porvari K, Kyllonen A, Lukkarinen O, Vihko P. The TMPRSS2 gene encoding transmembrane serine protease is overexpressed in a majority of prostate cancer patients: detection of mutated TMPRSS2 form in a case of aggressive disease. Int. J. Cancer 2001. 94:705-710.

43. Lee J W, Yong S S, Choi J J, Lee S J, Kim B G, Park C S, Lee J H, Lin C Y, Dickson R B, Bae D S. Increased expression of matriptase is associated with histopathologic grades of cervical neoplasia. Hum. Pathol. 2005. 36:626-633.

44. Saleem M, Adhami V M, Zhong W, Longley B J, Lin C Y, Dickson R B, Reagan-Shaw S, Jarrard D F, Mukhtar H. A novel biomarker for staging human prostate adenocarcinoma: overexpression of matriptase with concomitant loss of its inhibitor, hepatocyte growth factor activator inhibitor-1. Cancer Epidemiol.Biomarkers Prey. 2006. 15:217-227.

45. Jin J S, Chen A, Hsieh D S, Yao C W, Cheng M F, Lin Y F. Expression of serine protease matriptase in renal cell carcinoma: correlation of tissue microarray immunohistochemical expression analysis results with clinicopathological parameters. Int. J. Surg. Pathol. 2006. 14:65-72.

46. Vogel L K, Saebo M, Skjelbred C F, Abell K, Pedersen E D, Vogel U, Kure E H. The ratio of Matriptase/HAI-1 mRNA is higher in colorectal cancer adenomas and carcinomas than corresponding tissue from control individuals. BMC. Cancer 2006. 6:176

47. Jin J S, Hsieh D S, Loh S H, Chen A, Yao C W, Yen C Y. Increasing expression of serine protease matriptase in ovarian tumors: tissue microarray analysis of immunostaining score with clinicopathological parameters. Mod. Pathol. 2006. 19:447-452.

48. List K, Szabo R, Molinolo A, Sriuranpong V, Redeye V, Murdock T, Burke B, Nielsen B S, Gutkind J S, Bugge T H. Deregulated matriptase causes ras-independent multistage carcinogenesis and promotes ras-mediated malignant transformation. Genes Dev. 2005. 19:1934-1950.

49. Scarman A L, Hooper J D, Boucaut K J, Sit M L, Webb G C, Normyle J F, Antalis T M. Organization and chromosomal localization of the murine Testisin gene encoding a serine protease temporally expressed during spermatogenesis. Eur. J. Biochem. 2001. 268:1250-1258.

50. Inoue M, Isobe M, Itoyama T, Kido H. Structural analysis of esp-1 gene (PRSS 21). Biochem. Biophys. Res. Commun. 1999. 266:564-568.

51. Hooper J D, Nicol D L, Dickinson J L, Eyre H J, Scarman A L, Normyle J F, Stuttgen M A, Douglas M L, Loveland K A, Sutherland G R, Antalis T M. Testisin, a new human serine proteinase expressed by premeiotic testicular germ cells and lost in testicular germ cell tumors. Cancer Res. 1999. 59:3199-3205.

52. Honda A, Yamagata K, Sugiura S, Watanabe K, Baba T. A mouse serine protease TESPS is selectively included into lipid rafts of sperm membrane presumably as a glycosylphosphatidylinositol-anchored protein. J. Biol. Chem. 2002. 277:16976-16984.

53. Kawano N, Kang W, Yamashita M, Koga Y, Yamazaki T, Hata T, Miyado K, Baba T. Mice Lacking Two Sperm 53. Serine Proteases, ACR and PRSS21, Are Subfertile, but the Mutant Sperm Are Infertile In Vitro. Biol. Reprod. 2010.
54. Yamashita M, Honda A, Ogura A, Kashiwabara S, Fukami K, Baba T. Reduced fertility of mouse epididymal sperm lacking Prss21/Tesp5 is rescued by sperm exposure to uterine microenvironment. Genes Cells 2008. 13: 1001-1013.
55. Netzel-Arnett S, Bugge T H, Hess R A, Carnes K, Stringer B W, Scarman A L, Hooper J D, Tonks I D, Kay G F, Antalis T M. The glycosylphosphatidylinositol-anchored serine protease PRSS21 (testisin) imparts murine epididymal sperm cell maturation and fertilizing ability. Biol. Reprod. 2009. 81:921-932.
56. Fratta E, Coral S, Covre A, Parisi G, Colizzi F, Danielli R, Nicolay H J, Sigalotti L, Maio M. The biology of cancer testis antigens: putative function, regulation and therapeutic potential. Mol. Oncol. 2011. 5:164-182.
57. Mirandola L, Cannon J, Cobos E, Bernardini G, Jenkins M R, Kast W M, Chiriva-Internati M. Cancer testis antigens: novel biomarkers and targetable proteins for ovarian cancer. Int. Rev. Immunol. 2011. 30:127-137.
58. Shigemasa K, Underwood L J, Beard J, Tanimoto H, Ohama K, Parmley T H, O'Brien T J. Overexpression of testisin, a serine protease expressed by testicular germ cells, in epithelial ovarian tumor cells. J. Soc. Gynecol. Investig. 2000. 7:358-362.
59. Bignotti E, Tassi R A, Calza S, Ravaggi A, Bandiera E, Rossi E, Donzelli C, Pasinetti B, Pecorelli S, Santin A D. Gene expression profile of ovarian serous papillary carcinomas: identification of metastasis-associated genes. Am J Obstet. Gynecol. 2007. 196:245-11.
60. Tang T, Kmet M, Corral L, Vartanian S, Tobler A, Papkoff J. Testisin, a glycosyl-phosphatidylinositol-linked serine protease, promotes malignant transformation in vitro and in vivo. Cancer Res. 2005. 65:868-878.
61. Yeom S Y, Jang H L, Lee S J, Kim E, Son H J, Kim B G, Park C. Interaction of testisin with maspin and its impact on invasion and cell death resistance of cervical cancer cells. FEBS Lett. 2010. 584:1469-1475.
62. Yang H, Wahlmuller F C, Sarg B, Furtmuller M, Geiger M. A+-helix of protein C inhibitor (PCI) is a cell-penetrating peptide that mediates cell membrane permeation of PCI. J. Biol. Chem. 2015. 290:3081-3091.
63. Hobson J P, Netzel-Arnett S, Szabo R, Rehault S M, Church F C, Strickland D K, Lawrence D A, Antalis T M, Bugge T H. Mouse DESC1 is located within a cluster of seven DESC1-like genes and encodes a type II transmembrane serine protease that forms serpin inhibitory complexes. J. Biol. Chem. 2004. 279:46981-46994.
64. Suzuki K. The multi-functional serpin, protein C inhibitor: beyond thrombosis and hemostasis. J. Thromb. Haemost. 2008. 6:2017-2026.
65. Prohaska T A, Wahlmuller F C, Furtmuller M, Geiger M. Interaction of protein C inhibitor with the type II transmembrane serine protease enteropeptidase. PLoS. One. 2012. 7:e39262
66. Pomerantsev A P, Pomerantseva O M, Moayeri M, Fattah R, Tallant C, Leppla S H. A *Bacillus anthracis* strain deleted for six proteases serves as an effective host for production of recombinant proteins. Protein Expr. Purif. 2011. 80:80-90.
67. Arora N, Klimpel K R, Singh Y, Leppla S H. Fusions of anthrax toxin lethal factor to the ADP-ribosylation domain of *Pseudomonas* exotoxin A are potent cytotoxins which are translocated to the cytosol of mammalian cells. J. Biol. Chem. 1992. 267:15542-15548.
68. Arora N, Leppla S H. Residues 1-254 of anthrax toxin lethal factor are sufficient to cause cellular uptake of fused polypeptides. J. Biol. Chem. 1993. 268:3334-3341.
69. Gupta P K, Liu S, Batavia M P, Leppla S H. The diphthamide modification on elongation factor-2 renders mammalian cells resistant to ricin. Cell Microbiol. 2008. 10:1687-1694.
70. Gettins PG. Serpin structure, mechanism, and function. Chem. Rev. 2002. 102:4751-4804.
71. Geiger M. Protein C inhibitor, a serpin with functions in- and outside vascular biology. Thromb. Haemost. 2007. 97:343-347.
72. Lazure C. The peptidase zymogen proregions: nature's way of preventing undesired activation and proteolysis. Curr. Pharm. Des 2002. 8:511-531.
73. Hedstrom L. Serine protease mechanism and specificity. Chem. Rev. 2002. 102:4501-4524.
74. Driesbaugh K H, Buzza M S, Martin E W, Conway G D, Kao J P, Antalis T M. Proteolytic activation of the protease-activated receptor (PAR)-2 by the glycosylphosphatidylinositol-anchored serine protease testisin. J. Biol. Chem. 2015. 290:3529-3541.
75. Oberst M D, Williams C A, Dickson R B, Johnson M D, Lin C Y. The activation of matriptase requires its noncatalytic domains, serine protease domain, and its cognate inhibitor. J. Biol. Chem. 2003. 278:26773-26779.
76. Oberst M D, Chen L Y, Kiyomiya K, Williams C A, Lee M S, Johnson M D, Dickson R B, Lin C Y. HAI-1 regulates activation and expression of matriptase, a membrane-bound serine protease. Am. J. Physiol Cell Physiol 2005. 289:C462-C470.
77. Friis S, Uzzun S K, Godiksen S, Peters D E, Lin C Y, Vogel L K, Bugge T H. A matriptase-prostasin reciprocal zymogen activation complex with unique features: prostasin as a non-enzymatic co-factor for matriptase activation. J. Biol. Chem. 2013. 288:19028-19039.
78. Buzza M S, Martin E W, Driesbaugh K H, Desilets A, Leduc R, Antalis T M. Prostasin is required for matriptase activation in intestinal epithelial cells to regulate closure of the paracellular pathway. J. Biol. Chem. 2013. 288: 10328-10337.
79. Buzza M S, Netzel-Arnett S, Shea-Donohue T, Zhao A, Lin C Y, List K, Szabo R, Fasano A, Bugge T H, Antalis T M. Membrane-anchored serine protease matriptase regulates epithelial barrier formation and permeability in the intestine. Proc. Natl. Acad. Sci. U.S.A 2010. 107: 4200-4205.
80. Phillips J E, Cooper S T, Potter E E, Church F C. Mutagenesis of recombinant protein C inhibitor reactive site residues alters target proteinase specificity. J. Biol. Chem. 1994. 269:16696-16700.
81. Rehault S M, Zechmeister-Machhart M, Fortenberry Y M, Malleier J, Binz N M, Cooper S T, Geiger M, Church F C. Characterization of recombinant human protein C inhibitor expressed in *Escherichia coli*. Biochim. Biophys. Acta 2005. 1748:57-65.
82. Kacprzak M M, Peinado J R, Than M E, Appel J, Henrich S, Lipkind G, Houghten R A, Bode W, Lindberg I. Inhibition of furin by polyarginine-containing peptides: nanomolar inhibition by nona-D-arginine. J. Biol. Chem. 2004. 279:36788-36794.
83. Desilets A, Longpre J M, Beaulieu M E, Leduc R. Inhibition of human matriptase by eglin c variants. FEBS Lett. 2006. 580:2227-2232.
84. Gabre J, Chabasse C, Cao C, Mukhopadhyay S, Siefert S, Bi Y, Netzel-Arnett S, Sarkar R, Zhang L. Activated protein C accelerates venous thrombus resolution through heme oxygenase-1 induction. J. Thromb. Haemost. 2014. 12:93-102.
85. Klimpel K R, Molloy S S, Thomas G, Leppla S H. Anthrax toxin protective antigen is activated by a cell surface protease with the sequence specificity and catalytic properties of furin. Proc. Natl. Acad. Sci. U.S.A 1992. 89:10277-10281.
86. Oberst M, Anders J, Xie B, Singh B, Ossandon M, Johnson M, Dickson R B, Lin C Y. Matriptase and HAI-1 are expressed by normal and malignant epithelial cells in vitro and in vivo. Am. J. Pathol. 2001. 158:1301-1311.
87. Tsai C H, Teng C H, Tu Y T, Cheng T S, Wu S R, Ko C J, Shyu H Y, Lan S W, Huang H P, Tzeng S F, Johnson M D, Lin C Y, Hsiao P W et al. HAI-2 suppresses the invasive growth and metastasis of prostate cancer through regulation of matriptase. Oncogene 2014. 33:4643-4652.
88. Xuan J A, Schneider D, Toy P, Lin R, Newton A, Zhu Y, Finster S, Vogel D, Mintzer B, Dinter H, Light D, Parry R, Polokoff M et al. Antibodies neutralizing hepsin protease activity do not impact cell growth but inhibit invasion of prostate and ovarian tumor cells in culture. Cancer Res. 2006. 66:3611-3619.
89. Gupta P K, Moayeri M, Crown D, Fattah R J, Leppla S H. Role of N-terminal amino acids in the potency of anthrax lethal factor. PLoS. One. 2008. 3:e3130
90. Netzel-Arnett S, Currie B M, Szabo R, Lin C Y, Chen L M, Chai K X, Antalis T M, Bugge T H, List K. Evidence for a matriptase-prostasin proteolytic cascade regulating terminal epidermal differentiation. J. Biol. Chem. 2006. 281:32941-32945.
91. Tse G H, Marson L P. A comparative study of 2 computer-assisted methods of quantifying brightfield microscopy images. Appl. Immunohistochem. Mol. Morphol. 2013. 21:464-470.
92. Martin E W, Buzza M S, Driesbaugh K H et al. Targeting the membrane-anchored serine protease testisin with a novel engineered anthrax toxin prodrug to kill tumor cells and reduce tumor burden. Oncotarget. 2015.
93. Neurath, H. and R. L. Hill. The Proteins, Academic Press, New York. 1997.
94. Cunningham, B C, Wells, J A. High-resolution epitope mapping of hGH-receptor interactions by alanine-scanning mutagenesis. Science 1989. 244:1081-1085.
95. Hilton, D J et al., Saturation mutagenesis of the WSXWS motif of the erythropoietin receptor. J. Biol. Chem. 1996. 271:4699-4708.
96. de Vos, A M et al. Human growth hormone and extracellular domain of its receptor: crystal structure of the complex. Science. 1992. 255:306-312.
97. Smith, L J et al. Human interleukin 4. The solution structure of a four-helix bundle protein. J. Mol. Biol. 1992. 224:899-904.
98. Wlodaver, A et al. Crystal structure of human recombinant interleukin-4 at 2.25 A resolution. FEBS Lett. 1992. 309:59-64.
99. Reidhaar-Olson, J F, Sauer, R T. Combinatorial cassette mutagenesis as a probe of the informational content of protein sequences. Science. 1988. 241:53-57.
100. Bowie, J U, Sauer, R T. Identifying determinants of folding and activity for a protein of unknown structure. Proc. Natl. Acad. Sci. USA. 1989. 86:2152-2156.
101. WO 95/17413.
102. WO 95/22625.
103. Rabideau, A E, Pentelute, B L. Delivery of Non-Native Cargo into Mammalian Cells Using Anthrax Lethal Toxin. ACS Chem. Biol. 2016. 11:1490-1501.
104. Shaw T J, Senterman M K, Dawson K, Crane C A, Vanderhyden B C. Characterization of intraperitoneal, orthotopic, and metastatic xenograft models of human ovarian cancer. Mol Ther. 2004;10:1032-1042.

What is claimed is:

1. An engineered protective antigen (PrAg), comprising:
   (a) the amino acid sequence set forth in SEQ ID NO:1, wherein furin activation site within amino acids 189-204 of SEQ ID NO:1 is replaced by a membrane-anchored serine protease activation site selected from the group consisting of (i) FTFRSARL (PCIS; SEQ ID NO:28); (ii) IPSRIVGG (TAS; SEQ ID NO:4); (iii) PQARITGG (PAS; SEQ ID NO:5); and (iv) PRFRITGG (UAS; SEQ ID NO:6),
   (b) the amino acid sequence of (a) lacking the N-terminal, 29 amino acid signal peptide, or
   (c) a sequence of (a) or (b) having 95% or more sequence identity over the entire length of the sequence of (a) or (b).

2. The engineered PrAg protein of claim 1, wherein the furin activation site consists of amino acids 193-200 of SEQ ID NO:1.

3. A method of inducing pore formation in a cell comprising contacting a cell with an engineered PrAg protein of claim 1 under conditions promoting pore formation in the cell, wherein the cell expresses an anthrax toxin PrAg protein receptor and a membrane-anchored serine protease.

4. The method of claim 3, wherein the receptor is one or more of tumor endothelial marker-8 (TEM8) and capillary morphogenesis gene-2 (CMG2).

5. The method of claim 3, wherein the membrane-anchored serine protease is one or more of testisin, hepsin, and matriptase.

* * * * *

SEQUENCE LISTING

```
<160> NUMBER OF SEQ ID NOS: 67

<210> SEQ ID NO 1
<211> LENGTH: 764
<212> TYPE: PRT
<213> ORGANISM: Bacillus anthracis

<400> SEQUENCE: 1

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125
```

-continued

```
Ala Ser Asn Ser Asn Lys Ile Arg Leu Glu Lys Gly Arg Leu Tyr Gln
130                 135                 140
Ile Lys Ile Gln Tyr Gln Arg Glu Asn Pro Thr Glu Lys Gly Leu Asp
145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
                180                 185                 190
Arg Lys Lys Arg Ser Thr Ser Ala Gly Pro Thr Val Pro Asp Arg Asp
                195                 200                 205
Asn Asp Gly Ile Pro Asp Ser Leu Glu Val Glu Gly Tyr Thr Val Asp
210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
                260                 265                 270
Asp Lys Asn Val Ser Pro Glu Ala Arg His Pro Leu Val Ala Ala Tyr
                275                 280                 285
Pro Ile Val His Val Asp Met Glu Asn Ile Ile Leu Ser Lys Asn Glu
290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
                340                 345                 350
Phe Ser Asn Ser Asn Ser Ser Thr Val Ala Ile Asp His Ser Leu Ser
                355                 360                 365
Leu Ala Gly Glu Arg Thr Trp Ala Glu Thr Met Gly Leu Asn Thr Ala
370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
                420                 425                 430
Ile Leu Ala Pro Asn Asn Tyr Tyr Pro Ser Lys Asn Leu Ala Pro Ile
                435                 440                 445
Ala Leu Asn Ala Gln Asp Asp Phe Ser Ser Thr Pro Ile Thr Met Asn
450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
                485                 490                 495
Arg Val Arg Val Asp Thr Gly Ser Asn Trp Ser Glu Val Leu Pro Gln
                500                 505                 510
Ile Gln Glu Thr Thr Ala Arg Ile Ile Phe Asn Gly Lys Asp Leu Asn
                515                 520                 525
Leu Val Glu Arg Arg Ile Ala Ala Val Asn Pro Ser Asp Pro Leu Glu
530                 535                 540
Thr Thr Lys Pro Asp Met Thr Leu Lys Glu Ala Leu Lys Ile Ala Phe
```

```
                545                 550                 555                 560
Gly Phe Asn Glu Pro Asn Gly Asn Leu Gln Tyr Gln Gly Lys Asp Ile
                    565                 570                 575
Thr Glu Phe Asp Phe Asn Phe Asp Gln Gln Thr Ser Gln Asn Ile Lys
                580                 585                 590
Asn Gln Leu Ala Glu Leu Asn Ala Thr Asn Ile Tyr Thr Val Leu Asp
            595                 600                 605
Lys Ile Lys Leu Asn Ala Lys Met Asn Ile Leu Ile Arg Asp Lys Arg
        610                 615                 620
Phe His Tyr Asp Arg Asn Asn Ile Ala Val Gly Ala Asp Glu Ser Val
625                 630                 635                 640
Val Lys Glu Ala His Arg Glu Val Ile Asn Ser Ser Thr Glu Gly Leu
                    645                 650                 655
Leu Leu Asn Ile Asp Lys Asp Ile Arg Lys Ile Leu Ser Gly Tyr Ile
                660                 665                 670
Val Glu Ile Glu Asp Thr Glu Gly Leu Lys Glu Val Ile Asn Asp Arg
            675                 680                 685
Tyr Asp Met Leu Asn Ile Ser Ser Leu Arg Gln Asp Gly Lys Thr Phe
        690                 695                 700
Ile Asp Phe Lys Lys Tyr Asn Asp Lys Leu Pro Leu Tyr Ile Ser Asn
705                 710                 715                 720
Pro Asn Tyr Lys Val Asn Val Tyr Ala Val Thr Lys Glu Asn Thr Ile
                    725                 730                 735
Ile Asn Pro Ser Glu Asn Gly Asp Thr Ser Thr Asn Gly Ile Lys Lys
                740                 745                 750
Ile Leu Ile Phe Ser Lys Lys Gly Tyr Glu Ile Gly
            755                 760

<210> SEQ ID NO 2
<211> LENGTH: 2295
<212> TYPE: DNA
<213> ORGANISM: Bacillus anthracis

<400> SEQUENCE: 2
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata tcatgtaac aatgtgggta     360 gatgaccaag aagtgattaa taagcttcct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta     540
caattgccag aattaaaaca aaatcttcg aattcaagaa aaaagagatc gacgtctgca     600
ggacctacgg ttccagaccg tgacaatgat ggaatccctg attcattaga ggtagaagga     660
tatacggttg atgtcaaaaa taaagaact tttctttcac catggatttc taatattcat     720
gaaaagaaag gattaaccaa atataaaatca tctcctgaaa aatggagcac ggcttctgat     780
ccgtacagtg atttcgaaaa ggttacagga cggattgata gaatgtgatc accagaggca     840
agacaccccc ttgtggcagc ttatccgatt gtacatgtag atatggagaa tattattctc     900
```

```
tcaaaaaatg aggatcaatc cacacagaat actgatagtc aaacgagaac aataagtaaa      960
aatacttcta caagtaggac acatactagt gaagtacatg gaaatgcaga agtgcatgcg     1020
tcgttctttg atattggtgg gagtgtatct gcaggattta gtaattcgaa ttcaagtacg     1080
gtcgcaattg atcattcact atctctagca ggggaaagaa cttgggctga acaatgggt      1140 ttaaataccg ctgatacagc aagattaaat gccaatatta gatatgtaaa tactgggacg     1200
gctccaatct acaacgtgtt accaacgact tcgttagtgt taggaaaaaa tcaaacactc     1260
gcgacaatta aagctaagga aaaccaatta agtcaaatac ttgcacctaa taattattat     1320
ccttctaaaa acttggcgcc aatcgcatta aatgcacaag acgatttcag ttctactcca     1380
attacaatga attacaatca atttcttgag ttagaaaaaa cgaaacaatt aagattagat     1440
acggatcaag tatatgggaa tatagcaaca tacaattttg aaaatggaag agtgagggtg     1500
gatacaggct cgaactggag tgaagtgtta ccgcaaattc aagaaacaac tgcacgtatc     1560
atttttaatg gaaaagattt aaatctggta gaaaggcgga tagcggcggt taatcctagt     1620
gatccattag aaacgactaa accggatatg acattaaaag aagcccttaa aatagcattt     1680
ggatttaacg aaccgaatgg aaacttacaa tatcaaggga aagacataac cgaatttgat     1740
tttaatttcg atcaacaaac atctcaaaat atcaagaatc agttagcgga attaaacgca     1800
actaacatat atactgtatt agataaaatc aaattaaatg caaaaatgaa tattttaata     1860
agagataaac gttttcatta tgatagaaat aacatagcag ttggggcgga tgagtcagta     1920
gttaaggagg ctcatagaga agtaattaat tcgtcaacag agggattatt gttaaatatt     1980
gataaggata taagaaaaat attatcaggt tatattgtag aaattgaaga tactgaaggg     2040
cttaaagaag ttataaatga cagatatgat atgttgaata tttctagttt acggcaagat     2100
ggaaaaacat ttatagattt taaaaaatat aatgataaat taccgttata tataagtaat     2160
cccaattata aggtaaatgt atatgctgtt actaaagaaa acactattat taatcctagt     2220
gagaatgggg atactagtac caacgggatc aagaaaattt taatctttc taaaaaaggc      2280 tatgagatag gataa                                                     2295
```

<210> SEQ ID NO 3  
<211> LENGTH: 735  
<212> TYPE: PRT  
<213> ORGANISM: Bacillus anthracis

<400> SEQUENCE: 3

```
Glu Val Lys Gln Glu Asn Arg Leu Leu Asn Glu Ser Glu Ser Ser Ser
  1               5                  10                  15

Gln Gly Leu Leu Gly Tyr Tyr Phe Ser Asp Leu Asn Phe Gln Ala Pro
             20                  25                  30

Met Val Thr Ser Ser Thr Thr Gly Asp Leu Ser Ile Pro Ser Ser
         35                  40                  45

Glu Leu Glu Asn Ile Pro Ser Glu Asn Gln Tyr Phe Gln Ser Ala Ile
     50                  55                  60

Trp Ser Gly Phe Ile Lys Val Lys Ser Asp Glu Tyr Thr Phe Ala
 65                  70                  75                  80

Thr Ser Ala Asp Asn His Val Thr Met Trp Val Asp Asp Gln Glu Val
                 85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
        115                 120                 125
```

Gly Leu Asp Phe Lys Leu Tyr Trp Thr Asp Ser Gln Asn Lys Lys Glu
130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
            165                 170                 175

Asp Arg Asp Asn Asp Gly Ile Pro Asp Ser Leu Glu Val Glu Gly Tyr
            180                 185                 190

Thr Val Asp Val Lys Asn Lys Arg Thr Phe Leu Ser Pro Trp Ile Ser
            195                 200                 205

Asn Ile His Glu Lys Lys Gly Leu Thr Lys Tyr Lys Ser Ser Pro Glu
210                 215                 220

Lys Trp Ser Thr Ala Ser Asp Pro Tyr Ser Asp Phe Glu Lys Val Thr
225                 230                 235                 240

Gly Arg Ile Asp Lys Asn Val Ser Pro Glu Ala Arg His Pro Leu Val
            245                 250                 255

Ala Ala Tyr Pro Ile Val His Val Asp Met Glu Asn Ile Ile Leu Ser
            260                 265                 270

Lys Asn Glu Asp Gln Ser Thr Gln Asn Thr Asp Ser Gln Thr Arg Thr
            275                 280                 285

Ile Ser Lys Asn Thr Ser Thr Ser Arg Thr His Thr Ser Glu Val His
290                 295                 300

Gly Asn Ala Glu Val His Ala Ser Phe Phe Asp Ile Gly Gly Ser Val
305                 310                 315                 320

Ser Ala Gly Phe Ser Asn Ser Asn Ser Ser Thr Val Ala Ile Asp His
            325                 330                 335

Ser Leu Ser Leu Ala Gly Glu Arg Thr Trp Ala Glu Thr Met Gly Leu
            340                 345                 350

Asn Thr Ala Asp Thr Ala Arg Leu Asn Ala Asn Ile Arg Tyr Val Asn
            355                 360                 365

Thr Gly Thr Ala Pro Ile Tyr Asn Val Leu Pro Thr Thr Ser Leu Val
            370                 375                 380

Leu Gly Lys Asn Gln Thr Leu Ala Thr Ile Lys Ala Lys Glu Asn Gln
385                 390                 395                 400

Leu Ser Gln Ile Leu Ala Pro Asn Asn Tyr Tyr Pro Ser Lys Asn Leu
            405                 410                 415

Ala Pro Ile Ala Leu Asn Ala Gln Asp Asp Phe Ser Ser Thr Pro Ile
            420                 425                 430

Thr Met Asn Tyr Asn Gln Phe Leu Glu Leu Glu Lys Thr Lys Gln Leu
            435                 440                 445

Arg Leu Asp Thr Asp Gln Val Tyr Gly Asn Ile Ala Thr Tyr Asn Phe
450                 455                 460

Glu Asn Gly Arg Val Arg Val Asp Thr Gly Ser Asn Trp Ser Glu Val
465                 470                 475                 480

Leu Pro Gln Ile Gln Glu Thr Thr Ala Arg Ile Ile Phe Asn Gly Lys
            485                 490                 495

Asp Leu Asn Leu Val Glu Arg Arg Ile Ala Ala Val Asn Pro Ser Asp
            500                 505                 510

Pro Leu Glu Thr Thr Lys Pro Asp Met Thr Leu Lys Glu Ala Leu Lys
            515                 520                 525

Ile Ala Phe Gly Phe Asn Glu Pro Asn Gly Asn Leu Gln Tyr Gln Gly
530                 535                 540

```
Lys Asp Ile Thr Glu Phe Asp Phe Asn Phe Asp Gln Gln Thr Ser Gln
545                 550                 555                 560

Asn Ile Lys Asn Gln Leu Ala Glu Leu Asn Ala Thr Asn Ile Tyr Thr
            565                 570                 575

Val Leu Asp Lys Ile Lys Leu Asn Ala Lys Met Asn Ile Leu Ile Arg
        580                 585                 590

Asp Lys Arg Phe His Tyr Asp Arg Asn Asn Ile Ala Val Gly Ala Asp
    595                 600                 605

Glu Ser Val Val Lys Glu Ala His Arg Glu Val Ile Asn Ser Ser Thr
610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
        660                 665                 670

Lys Thr Phe Ile Asp Phe Lys Lys Tyr Asn Asp Lys Leu Pro Leu Tyr
    675                 680                 685

Ile Ser Asn Pro Asn Tyr Lys Val Asn Val Tyr Ala Val Thr Lys Glu
690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 4
<211> LENGTH: 8
<212> TYPE: PRT
<213> ORGANISM: Homo sapiens

<400> SEQUENCE: 4

Ile Pro Ser Arg Ile Val Gly Gly
1               5

<210> SEQ ID NO 5
<211> LENGTH: 8
<212> TYPE: PRT
<213> ORGANISM: Homo sapiens

<400> SEQUENCE: 5

Pro Gln Ala Arg Ile Thr Gly Gly
1               5

<210> SEQ ID NO 6
<211> LENGTH: 8
<212> TYPE: PRT
<213> ORGANISM: Homo sapiens

<400> SEQUENCE: 6

Pro Arg Phe Arg Ile Thr Gly Gly
1               5

<210> SEQ ID NO 7
<211> LENGTH: 8
<212> TYPE: PRT
<213> ORGANISM: Homo sapiens

<400> SEQUENCE: 7

Asp Asp Asp Lys Ile Val Gly Gly
1               5
```

```
<210> SEQ ID NO 8
<211> LENGTH: 8
<212> TYPE: PRT
<213> ORGANISM: Homo sapiens

<400> SEQUENCE: 8

Ile Thr Ser Arg Ile Val Gly Gly
1               5

<210> SEQ ID NO 9
<211> LENGTH: 7
<212> TYPE: PRT
<213> ORGANISM: Homo sapiens

<400> SEQUENCE: 9

Ala Gly Gly Arg Ile Val Gly
1               5

<210> SEQ ID NO 10
<211> LENGTH: 7
<212> TYPE: PRT
<213> ORGANISM: Homo sapiens

<400> SEQUENCE: 10

Arg Gln Ala Arg Val Val Gly
1               5

<210> SEQ ID NO 11
<211> LENGTH: 8
<212> TYPE: PRT
<213> ORGANISM: Homo sapiens

<400> SEQUENCE: 11

Pro Ser Ser Arg Ile Val Gly Gly
1               5

<210> SEQ ID NO 12
<211> LENGTH: 8
<212> TYPE: PRT
<213> ORGANISM: Homo sapiens

<400> SEQUENCE: 12

Ala Leu His Arg Ile Ile Gly Gly
1               5

<210> SEQ ID NO 13
<211> LENGTH: 8
<212> TYPE: PRT
<213> ORGANISM: Homo sapiens

<400> SEQUENCE: 13

Ile Thr Pro Lys Ile Val Gly Gly
1               5

<210> SEQ ID NO 14
<211> LENGTH: 8
<212> TYPE: PRT
<213> ORGANISM: Homo sapiens

<400> SEQUENCE: 14

Met Asn Lys Arg Ile Leu Gly Gly
1               5
```

<210> SEQ ID NO 15
<211> LENGTH: 8
<212> TYPE: PRT
<213> ORGANISM: Homo sapiens

<400> SEQUENCE: 15

Pro Val Asp Arg Ile Val Gly Gly
1               5

<210> SEQ ID NO 16
<211> LENGTH: 8
<212> TYPE: PRT
<213> ORGANISM: Homo sapiens

<400> SEQUENCE: 16

Arg Gln Ser Arg Ile Val Gly Gly
1               5

<210> SEQ ID NO 17
<211> LENGTH: 8
<212> TYPE: PRT
<213> ORGANISM: Homo sapiens

<400> SEQUENCE: 17

Tyr Ser Ser Arg Ile Val Gly Gly
1               5

<210> SEQ ID NO 18
<211> LENGTH: 8
<212> TYPE: PRT
<213> ORGANISM: Homo sapiens

<400> SEQUENCE: 18

Lys Thr Pro Arg Val Val Gly Val
1               5

<210> SEQ ID NO 19
<211> LENGTH: 8
<212> TYPE: PRT
<213> ORGANISM: Homo sapiens

<400> SEQUENCE: 19

Leu Ala Ser Arg Ile Val Gly Gly
1               5

<210> SEQ ID NO 20
<211> LENGTH: 8
<212> TYPE: PRT
<213> ORGANISM: Homo sapiens

<400> SEQUENCE: 20

Met Ala Gly Arg Ile Val Gly Gly
1               5

<210> SEQ ID NO 21
<211> LENGTH: 8
<212> TYPE: PRT
<213> ORGANISM: Homo sapiens

<400> SEQUENCE: 21

Gln Ser Leu Arg Ile Val Gly Gly
1               5

<210> SEQ ID NO 22
<211> LENGTH: 7

```
<212> TYPE: PRT
<213> ORGANISM: Homo sapiens

<400> SEQUENCE: 22

Asn Val Asn Arg Ala Ser Gly
1               5

<210> SEQ ID NO 23
<211> LENGTH: 8
<212> TYPE: PRT
<213> ORGANISM: Homo sapiens

<400> SEQUENCE: 23

Thr Gly Asn Lys Ile Val Asn Gly
1               5

<210> SEQ ID NO 24
<211> LENGTH: 8
<212> TYPE: PRT
<213> ORGANISM: Homo sapiens

<400> SEQUENCE: 24

Ser Glu Gln Arg Ile Leu Gly Gly
1               5

<210> SEQ ID NO 25
<211> LENGTH: 8
<212> TYPE: PRT
<213> ORGANISM: Homo sapiens

<400> SEQUENCE: 25

Met Thr Gly Arg Ile Val Gly Gly
1               5

<210> SEQ ID NO 26
<211> LENGTH: 8
<212> TYPE: PRT
<213> ORGANISM: Homo sapiens

<400> SEQUENCE: 26

Ser Thr Gln Arg Ile Val Gln Gly
1               5

<210> SEQ ID NO 27
<211> LENGTH: 8
<212> TYPE: PRT
<213> ORGANISM: Homo sapiens

<400> SEQUENCE: 27

Gln Gly Ser Arg Ile Ile Gly Gly
1               5

<210> SEQ ID NO 28
<211> LENGTH: 8
<212> TYPE: PRT
<213> ORGANISM: Homo sapiens

<400> SEQUENCE: 28

Phe Thr Phe Arg Ser Ala Arg Leu
1               5

<210> SEQ ID NO 29
<211> LENGTH: 8
<212> TYPE: PRT
<213> ORGANISM: Homo sapiens
```

```
<400> SEQUENCE: 29

Ala Ile Pro Met Ser Ile Pro Pro
1               5

<210> SEQ ID NO 30
<211> LENGTH: 8
<212> TYPE: PRT
<213> ORGANISM: Homo sapiens

<400> SEQUENCE: 30

Glu Lys Ala Trp Ser Lys Tyr Gln
1               5

<210> SEQ ID NO 31
<211> LENGTH: 8
<212> TYPE: PRT
<213> ORGANISM: Homo sapiens

<400> SEQUENCE: 31

Ile Thr Leu Leu Ser Ala Leu Val
1               5

<210> SEQ ID NO 32
<211> LENGTH: 8
<212> TYPE: PRT
<213> ORGANISM: Homo sapiens

<400> SEQUENCE: 32

Ile Lys Phe Phe Ser Ala Gln Thr
1               5

<210> SEQ ID NO 33
<211> LENGTH: 8
<212> TYPE: PRT
<213> ORGANISM: Homo sapiens

<400> SEQUENCE: 33

Leu Asn Leu Thr Ser Lys Pro Ile
1               5

<210> SEQ ID NO 34
<211> LENGTH: 8
<212> TYPE: PRT
<213> ORGANISM: Homo sapiens

<400> SEQUENCE: 34

Leu Ser Asp Gln Pro Glu Asn Thr
1               5

<210> SEQ ID NO 35
<211> LENGTH: 8
<212> TYPE: PRT
<213> ORGANISM: Homo sapiens

<400> SEQUENCE: 35

Asn Lys Pro Glu Val Leu Glu Val
1               5

<210> SEQ ID NO 36
<211> LENGTH: 8
<212> TYPE: PRT
<213> ORGANISM: Homo sapiens

<400> SEQUENCE: 36
```

```
Phe Ile Val Arg Ser Lys Asp Gly
1               5

<210> SEQ ID NO 37
<211> LENGTH: 8
<212> TYPE: PRT
<213> ORGANISM: Homo sapiens

<400> SEQUENCE: 37

Ile Thr Ala Tyr Ser Met Pro Pro
1               5

<210> SEQ ID NO 38
<211> LENGTH: 8
<212> TYPE: PRT
<213> ORGANISM: Homo sapiens

<400> SEQUENCE: 38

Leu Thr Pro Met Glu Thr Pro Leu
1               5

<210> SEQ ID NO 39
<211> LENGTH: 8
<212> TYPE: PRT
<213> ORGANISM: Homo sapiens

<400> SEQUENCE: 39

Met Thr Gly Arg Thr Gly His Gly
1               5

<210> SEQ ID NO 40
<211> LENGTH: 8
<212> TYPE: PRT
<213> ORGANISM: Homo sapiens

<400> SEQUENCE: 40

Ile Leu Gln His Lys Asp Glu Leu
1               5

<210> SEQ ID NO 41
<211> LENGTH: 8
<212> TYPE: PRT
<213> ORGANISM: Homo sapiens

<400> SEQUENCE: 41

Ile Ala Gly Arg Ser Leu Asn Pro
1               5

<210> SEQ ID NO 42
<211> LENGTH: 8
<212> TYPE: PRT
<213> ORGANISM: Homo sapiens

<400> SEQUENCE: 42

Phe Met Pro Leu Ser Thr Gln Val
1               5

<210> SEQ ID NO 43
<211> LENGTH: 8
<212> TYPE: PRT
<213> ORGANISM: Homo sapiens

<400> SEQUENCE: 43

Val Ser Ala Arg Met Ala Pro Glu
```

-continued

```
1               5

<210> SEQ ID NO 44
<211> LENGTH: 8
<212> TYPE: PRT
<213> ORGANISM: Homo sapiens

<400> SEQUENCE: 44

Leu Ile Ala Arg Ser Ser Pro Pro
1               5

<210> SEQ ID NO 45
<211> LENGTH: 8
<212> TYPE: PRT
<213> ORGANISM: Homo sapiens

<400> SEQUENCE: 45

Ala Met Ser Arg Met Ser Leu Ser
1               5

<210> SEQ ID NO 46
<211> LENGTH: 8
<212> TYPE: PRT
<213> ORGANISM: Homo sapiens

<400> SEQUENCE: 46

Ala Ile Ser Arg Met Ala Val Leu
1               5

<210> SEQ ID NO 47
<211> LENGTH: 8
<212> TYPE: PRT
<213> ORGANISM: Homo sapiens

<400> SEQUENCE: 47

Ile Pro Val Ile Met Ser Leu Ala
1               5

<210> SEQ ID NO 48
<211> LENGTH: 764
<212> TYPE: PRT
<213> ORGANISM: Artificial Sequence
<220> FEATURE:
<223> OTHER INFORMATION: engineered PrAg-TAS polypeptide

<400> SEQUENCE: 48

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
                20                  25                  30

Gln Glu Asn Arg Leu Leu Asn Glu Ser Glu Ser Ser Ser Gln Gly Leu
            35                  40                  45

Leu Gly Tyr Tyr Phe Ser Asp Leu Asn Phe Gln Ala Pro Met Val Val
        50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
                100                 105                 110

Asp Asn His Val Thr Met Trp Val Asp Asp Gln Glu Val Ile Asn Lys
            115                 120                 125
```

```
Ala Ser Asn Ser Asn Lys Ile Arg Leu Glu Lys Gly Arg Leu Tyr Gln
            130                 135                 140
Ile Lys Ile Gln Tyr Gln Arg Glu Asn Pro Thr Glu Lys Gly Leu Asp
145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
            180                 185                 190
Ile Pro Ser Arg Ile Val Gly Gly Pro Thr Val Pro Asp Arg Asp
            195                 200                 205
Asn Asp Gly Ile Pro Asp Ser Leu Glu Val Glu Gly Tyr Thr Val Asp
210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
            245                 250                 255
Thr Ala Ser Asp Pro Tyr Ser Asp Phe Glu Lys Val Thr Gly Arg Ile
            260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
            290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
            325                 330                 335
Glu Val His Ala Ser Phe Phe Asp Ile Gly Gly Ser Val Ser Ala Gly
            340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
            370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
            405                 410                 415
Asn Gln Thr Leu Ala Thr Ile Lys Ala Lys Glu Asn Gln Leu Ser Gln
            420                 425                 430
Ile Leu Ala Pro Asn Asn Tyr Tyr Pro Ser Lys Asn Leu Ala Pro Ile
            435                 440                 445
Ala Leu Asn Ala Gln Asp Asp Phe Ser Ser Thr Pro Ile Thr Met Asn
450                 455                 460
Tyr Asn Gln Phe Leu Glu Leu Glu Lys Thr Lys Gln Leu Arg Leu Asp
465                 470                 475                 480
Thr Asp Gln Val Tyr Gly Asn Ile Ala Thr Tyr Asn Phe Glu Asn Gly
                485                 490                 495
Arg Val Arg Val Asp Thr Gly Ser Asn Trp Ser Glu Val Leu Pro Gln
                500                 505                 510
Ile Gln Glu Thr Thr Ala Arg Ile Ile Phe Asn Gly Lys Asp Leu Asn
            515                 520                 525
Leu Val Glu Arg Arg Ile Ala Ala Val Asn Pro Ser Asp Pro Leu Glu
530                 535                 540
```

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 49
<211> LENGTH: 2295
<212> TYPE: DNA
<213> ORGANISM: Artificial Sequence
<220> FEATURE:
<223> OTHER INFORMATION: engineered PrAg-TAS polynucleotide

<400> SEQUENCE: 49

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata atcatgtaac aatgtgggta     360
gatgaccaag aagtgattaa taagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta     540
caattgccag aattaaaaca aaaatcttcg aattcaatac cctcgagaat cgtgggtgga     600
ggacctacgg ttccagaccg tgacaatgat ggaatccctg attcattaga ggtagaagga     660
tatacggttg atgtcaaaaa taaagaact tttcttcac catggatttc taatattcat     720
gaaaagaaag gattaaccaa atataaatca tctcctgaaa aatggagcac ggcttctgat     780
ccgtacagtg atttcgaaaa ggttacagga cggattgata agaatgtatc accagaggca     840
```

```
agacacccc ttgtggcagc ttatccgatt gtacatgtag atatggagaa tattattctc      900 tcaaaaatg aggatcaatc cacacagaat actgatagtc aaacgagaac aataagtaaa      960
aatacttcta caagtaggac acatactagt gaagtacatg gaaatgcaga agtgcatgcg    1020
tcgttctttg atattggtgg gagtgtatct gcaggattta gtaattcgaa ttcaagtacg    1080
gtcgcaattg atcattcact atctctagca ggggaaagaa cttgggctga acaatgggt     1140 ttaaataccg ctgatacagc aagattaaat gccaatatta gatatgtaaa tactgggacg    1200
gctccaatct caacgtgtt accaacgact tcgttagtgt taggaaaaaa tcaaacactc      1260
gcgacaatta aagctaagga aaaccaatta agtcaaatac ttgcacctaa taattattat     1320
ccttctaaaa acttggcgcc aatcgcatta aatgcacaag acgatttcag ttctactcca     1380
attacaatga attacaatca atttcttgag ttagaaaaaa cgaaacaatt aagattagat     1440
acggatcaag tatatgggaa tatagcaaca tacaattttg aaaatggaag agtgagggtg     1500
gatacaggct cgaactggag tgaagtgtta ccgcaaattc aagaaacaac tgcacgtatc     1560
atttttaatg gaaaagattt aaatctggta gaaaggcgga tagcggcggt taatcctagt     1620
gatccattag aaacgactaa accggatatg acattaaaag aagcccttaa aatagcattt     1680
ggatttaacg aaccgaatgg aaacttacaa tatcaaggga aagacataac cgaatttgat     1740
tttaatttcg atcaacaaac atctcaaaat atcaagaatc agttagcgga attaaacgca     1800
actaacatat atactgtatt agataaaatc aaattaaatg caaaaatgaa tatttttaata    1860 agagataaac gttttcatta tgatagaaat aacatagcag ttggggcgga tgagtcagta     1920
gttaaggagg ctcatagaga agtaattaat tcgtcaacag agggattatt gttaaatatt    1980
gataaggata taagaaaaat attatcaggt tatattgtag aaattgaaga tactgaaggg    2040
cttaaagaag ttataaatga cagatatgat atgttgaata tttctagttt acggcaagat    2100
ggaaaaacat ttatagattt taaaaaatat aatgataaat taccgttata tataagtaat    2160
cccaattata aggtaaatgt atatgctgtt actaaagaaa acactattat taatcctagt    2220
gagaatgggg atactagtac caacgggatc aagaaaattt taatcttttc taaaaaaggc    2280
tatgagatag gataa                                                     2295
```

<210> SEQ ID NO 50
<211> LENGTH: 764
<212> TYPE: PRT
<213> ORGANISM: Artificial Sequence
<220> FEATURE:
<223> OTHER INFORMATION: engineered PrAg-PAS polypeptide

<400> SEQUENCE: 50

```
Met Lys Lys Arg Lys Val Leu Ile Pro Leu Met Ala Leu Ser Thr Ile
1               5

-continued

```
Phe Ile Lys Val Lys Lys Ser Asp Glu Tyr Thr Phe Ala Thr Ser Ala
                100                 105                 110

Asp Asn His Val Thr Met Trp Val Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Pro Gln Ala Arg Ile Thr Gly Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
```

| | | 515 | | | 520 | | | 525 | | | |
|---|---|---|---|---|---|---|---|---|---|---|---|
| Leu | Val | Glu | Arg | Arg | Ile | Ala | Ala | Val | Asn | Pro | Ser | Asp | Pro | Leu | Glu |
| | | 530 | | | | 535 | | | | 540 | |

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 51
<211> LENGTH: 2295
<212> TYPE: DNA
<213> ORGANISM: Artificial Sequence
<220> FEATURE:
<223> OTHER INFORMATION: engineered PrAg-PAS polynucleotide

<400> SEQUENCE: 51

```
atgaaaaaac gaaaagtgtt aataccatta

```
tatacggttg atgtcaaaaa taaaagaact tttctttcac catggatttc taatattcat    720
gaaaagaaag gattaaccaa atataaatca tctcctgaaa aatggagcac ggcttctgat    780
ccgtacagtg atttcgaaaa ggttacagga cggattgata agaatgtatc accagaggca    840
agacaccccc ttgtggcagc ttatccgatt gtacatgtag atatggagaa attattctc    900
tcaaaaatg aggatcaatc cacacagaat actgatagtc aaacgagaac aataagtaaa    960
aatacttcta caagtaggac acatactagt gaagtacatg gaaatgcaga agtgcatgcg   1020
tcgttctttg atattggtgg gagtgtatct gcaggattta gtaattcgaa ttcaagtacg   1080
gtcgcaattg atcattcact atctctagca ggggaaagaa cttgggctga acaatgggt   1140
ttaaataccg ctgatacagc aagattaaat gccaatatta gatatgtaaa tactgggacg   1200
gctccaatct acaacgtgtt accaacgact tcgttagtgt taggaaaaaa tcaaacactc   1260
gcgacaatta aagctaagga aaccaattaa agtcaaatac ttgcacctaa taattattat   1320
ccttctaaaa acttggcgcc aatcgcatta aatgcacaag acgatttcag ttctactcca   1380
attacaatga attacaatca atttcttgag ttagaaaaaa cgaaacaatt aagattagat   1440
acggatcaag tatatgggaa tatagcaaca tacaattttg aaaatggaag agtgagggtg   1500
gatacaggct cgaactggag tgaagtgtta ccgcaaattc agaaacaac tgcacgtatc   1560
atttttaatg aaaagatttt aaatctggta gaaaggcgga tagcggcggt taatcctagt   1620
gatccattag aaacgactaa accgatatg acattaaaag aagcccttaa aatagcattt   1680
ggatttaacg aaccgaatgg aaacttacaa tatcaaggga agacataac cgaatttgat   1740
tttaatttcg atcaacaaac atctcaaaat atcaagaatc agttagcgga attaaacgca   1800
actaacatat atactgtatt agataaaatc aaattaaatg caaaaatgaa tattttaata   1860
agagataaac gttttcatta tgatagaaat aacatagcag ttggggcgga tgagtcagta   1920
gttaaggagg ctcatagaga agtaattaat tcgtcaacag agggattatt gttaaatatt   1980
gataaggata taagaaaaat attatcaggt tatattgtag aaattgaaga tactgaaggg   2040
cttaaagaag ttataaatga cagatatgat atgttgaata tttctagttt acggcaagat   2100
ggaaaaacat ttatagattt taaaaaatat aatgataaat taccgttata tataagtaat   2160
cccaattata aggtaaatgt atatgctgtt actaaagaaa acactattat taatcctagt   2220
gagaatgggg atactagtac caacgggatc aagaaaattt taatctttc taaaaaggc   2280
tatgagatag gataa                                                   2295

<210> SEQ ID NO 52
<211> LENGTH: 764
<212> TYPE: PRT
<213> ORGANISM: Artificial Sequence
<220> FEATURE:
<223> OTHER INFORMATION: engineered PrAg-UAS polypeptide

<400> SEQUENCE: 52

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
```

```
            65                  70                  75                  80
Asn Ile Pro Ser Glu Asn Gln Tyr Phe Gln Ser Ala Ile Trp Ser Gly
                    85                  90                  95

Phe Ile Lys Val Lys Lys Ser Asp Glu Tyr Thr Phe Ala Thr Ser Ala
                100                 105                 110

Asp Asn His Val Thr Met Trp Val Asp Asp Gln Glu Val Ile Asn Lys
                115                 120                 125

Ala Ser Asn Ser Asn Lys Ile Arg Leu Glu Lys Gly Arg Leu Tyr Gln
130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
                180                 185                 190

Pro Arg Phe Arg Ile Thr Gly Gly Pro Thr Val Pro Asp Arg Asp
                195                 200                 205

Asn Asp Gly Ile Pro Asp Ser Leu Glu Val Glu Gly Tyr Thr Val Asp
210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
                260                 265                 270

Asp Lys Asn Val Ser Pro Glu Ala Arg His Pro Leu Val Ala Ala Tyr
                275                 280                 285

Pro Ile Val His Val Asp Met Glu Asn Ile Ile Leu Ser Lys Asn Glu
                290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
                340                 345                 350

Phe Ser Asn Ser Asn Ser Ser Thr Val Ala Ile Asp His Ser Leu Ser
                355                 360                 365

Leu Ala Gly Glu Arg Thr Trp Ala Glu Thr Met Gly Leu Asn Thr Ala
370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
                420                 425                 430

Ile Leu Ala Pro Asn Asn Tyr Tyr Pro Ser Lys Asn Leu Ala Pro Ile
                435                 440                 445

Ala Leu Asn Ala Gln Asp Asp Phe Ser Ser Thr Pro Ile Thr Met Asn
450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495
```

```
Arg Val Arg Val Asp Thr Gly Ser Asn Trp Ser Glu Val Leu Pro Gln
            500                 505                 510
Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560
Gly Phe Asn Glu Pro Asn Gly Asn Leu Gln Tyr Gln Gly Lys Asp Ile
                565                 570                 575
Thr Glu Phe Asp Phe Asn Phe Asp Gln Gln Thr Ser Gln Asn Ile Lys
            580                 585                 590
Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640
Val Lys Glu Ala His Arg Glu Val Ile Asn Ser Ser Thr Glu Gly Leu
                645                 650                 655
Leu Leu Asn Ile Asp Lys Asp Ile Arg Lys Ile Leu Ser Gly Tyr Ile
            660                 665                 670
Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720
Pro Asn Tyr Lys Val Asn Val Tyr Ala Val Thr Lys Glu Asn Thr Ile
                725                 730                 735
Ile Asn Pro Ser Glu Asn Gly Asp Thr Ser Thr Asn Gly Ile Lys Lys
            740                 745                 750
Ile Leu Ile Phe Ser Lys Lys Gly Tyr Glu Ile Gly
        755                 760
```

<210> SEQ ID NO 53
<211> LENGTH: 2295
<212> TYPE: DNA
<213> ORGANISM: Artificial Sequence
<220> FEATURE:
<223> OTHER INFORMATION: engineered PrAg-UAS polynucleotide

<400> SEQUENCE: 53

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata atcatgtaac aatgtgggta     360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaaagaag tgatttctag tgataactta     540
```

```
caattgccag aattaaaaca aaaatcttcg aattcaccga ggtttagaat cacgggtgga    600
ggacctacgg ttccagaccg tgacaatgat ggaatccctg attcattaga ggtagaagga    660
tatacggttg atgtcaaaaa taaaagaact tttctttcac catggatttc taatattcat    720
gaaagaaag gattaaccaa atataaatca tctcctgaaa aatggagcac ggcttctgat    780
ccgtacagtg atttcgaaaa ggttacagga cggattgata agaatgtatc accagaggca    840
agacaccccc ttgtggcagc ttatccgatt gtacatgtag atatggagaa tattattctc    900
tcaaaaaatg aggatcaatc cacacagaat actgatagtc aaacgagaac aataagtaaa    960
aatacttcta caagtaggac acatactagt gaagtacatg aaatgcaga agtgcatgcg     1020
tcgttctttg atattggtgg gagtgtatct gcaggattta gtaattcgaa ttcaagtacg    1080
gtcgcaattg atcattcact atctctagca ggggaaagaa cttgggctga acaatgggt     1140
ttaaataccg ctgatacagc aagattaaat gccaatatta gatatgtaaa tactgggacg    1200
gctccaatct acaacgtgtt accaacgact tcgttagtgt taggaaaaaa tcaaacactc    1260
gcgacaatta aagctaagga aaaccaatta agtcaaatac ttgcacctaa taattattat    1320
ccttctaaaa acttggcgcc aatcgcatta aatgcacaag acgatttcag ttctactcca    1380
attacaatga attacaatca atttcttgag ttagaaaaaa cgaaacaatt aagattagat    1440
acggatcaag tatatgggaa tatagcaaca tacaattttg aaaatggaag agtgagggtg    1500
gatacaggct cgaactggag tgaagtgtta ccgcaaattc aagaaacaac tgcacgtatc    1560
attttaatg aaagagttt aaatctggta gaaggcgga tagcggcggt taatcctagt      1620
gatccattag aaacgactaa accggatatg acattaaaag aagcccttaa aatagcattt    1680
ggatttaacg aaccgaatgg aaacttacaa tatcaaggga aagacataac cgaatttgat    1740
tttaatttcg atcaacaaac atctcaaaat atcaagaatc agttagcgga attaaacgca    1800
actaacatat atactgtatt agataaaatc aaattaaatg caaaaatgaa tattttaata    1860
agagataaac gttttcatta tgatagaaat aacatagcag ttggggcgga tgagtcagta    1920
gttaaggagg ctcatagaga agtaattaat tcgtcaacag agggattatt gttaaatatt    1980
gataaggata taagaaaaat attatcaggt tatattgtag aaattgaaga tactgaaggg    2040
cttaaagaag ttataaatga cagatatgat atgttgaata tttctagttt acggcaagat    2100
ggaaaaacat ttatagattt taaaaaatat aatgataaat taccgttata tataagtaat    2160
cccaattata aggtaaatgt atatgctgtt actaaagaaa acactattat taatcctagt    2220
gagaatgggg atactagtac caacgggatc aagaaaattt taatcttttc taaaaaaggc    2280
tatgagatag gataa                                                    2295
```

<210> SEQ ID NO 54
<211> LENGTH: 764
<212> TYPE: PRT
<213> ORGANISM: Artificial Sequence
<220> FEATURE:
<223> OTHER INFORMATION: engineered PrAg-PCIS polypeptide

<400> SEQUENCE: 54

```
Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Ser Gln Gly Leu
        35                  40                  45
```

-continued

```
Leu Gly Tyr Tyr Phe Ser Asp Leu Asn Phe Gln Ala Pro Met Val Val
     50                  55                  60
Thr Ser Ser Thr Thr Gly Asp Leu Ser Ile Pro Ser Ser Glu Leu Glu
 65                  70                  75                  80
Asn Ile Pro Ser Glu Asn Gln Tyr Phe Gln Ser Ala Ile Trp Ser Gly
                 85                  90                  95
Phe Ile Lys Val Lys Lys Ser Asp Glu Tyr Thr Phe Ala Thr Ser Ala
                100                 105                 110
Asp Asn His Val Thr Met Trp Val Asp Gln Glu Val Ile Asn Lys
            115                 120                 125
Ala Ser Asn Ser Asn Lys Ile Arg Leu Glu Lys Gly Arg Leu Tyr Gln
130                 135                 140
Ile Lys Ile Gln Tyr Gln Arg Glu Asn Pro Thr Glu Lys Gly Leu Asp
145                 150                 155                 160
Phe Lys Leu Tyr Trp Thr Asp Ser Gln Asn Lys Lys Glu Val Ile Ser
                165                 170                 175
Ser Asp Asn Leu Gln Leu Pro Glu Leu Lys Gln Lys Ser Ser Asn Ser
                180                 185                 190
Phe Thr Phe Arg Ser Ala Arg Leu Gly Pro Thr Val Pro Asp Arg Asp
            195                 200                 205
Asn Asp Gly Ile Pro Asp Ser Leu Glu Val Glu Gly Tyr Thr Val Asp
210                 215                 220
Val Lys Asn Lys Arg Thr Phe Leu Ser Pro Trp Ile Ser Asn Ile His
225                 230                 235                 240
Glu Lys Lys Gly Leu Thr Lys Tyr Lys Ser Ser Pro Glu Lys Trp Ser
                245                 250                 255
Thr Ala Ser Asp Pro Tyr Ser Asp Phe Glu Lys Val Thr Gly Arg Ile
                260                 265                 270
Asp Lys Asn Val Ser Pro Glu Ala Arg His Pro Leu Val Ala Ala Tyr
            275                 280                 285
Pro Ile Val His Val Asp Met Glu Asn Ile Ile Leu Ser Lys Asn Glu
290                 295                 300
Asp Gln Ser Thr Gln Asn Thr Asp Ser Gln Thr Arg Thr Ile Ser Lys
305                 310                 315                 320
Asn Thr Ser Thr Ser Arg Thr His Thr Ser Glu Val His Gly Asn Ala
                325                 330                 335
Glu Val His Ala Ser Phe Phe Asp Ile Gly Gly Ser Val Ser Ala Gly
                340                 345                 350
Phe Ser Asn Ser Asn Ser Ser Thr Val Ala Ile Asp His Ser Leu Ser
            355                 360                 365
Leu Ala Gly Glu Arg Thr Trp Ala Glu Thr Met Gly Leu Asn Thr Ala
370                 375                 380
Asp Thr Ala Arg Leu Asn Ala Asn Ile Arg Tyr Val Asn Thr Gly Thr
385                 390                 395                 400
Ala Pro Ile Tyr Asn Val Leu Pro Thr Thr Ser Leu Val Leu Gly Lys
                405                 410                 415
Asn Gln Thr Leu Ala Thr Ile Lys Ala Lys Glu Asn Gln Leu Ser Gln
                420                 425                 430
Ile Leu Ala Pro Asn Asn Tyr Tyr Pro Ser Lys Asn Leu Ala Pro Ile
            435                 440                 445
Ala Leu Asn Ala Gln Asp Asp Phe Ser Ser Thr Pro Ile Thr Met Asn
450                 455                 460
```

```
Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760
```

<210> SEQ ID NO 55
<211> LENGTH: 2295
<212> TYPE: DNA
<213> ORGANISM: Artificial Sequence
<220> FEATURE:
<223> OTHER INFORMATION: engineered PrAg-PCIS polynucleotide

<400> SEQUENCE: 55

```
atgaaaaaac gaaaagtgtt aataccatta atggcattgt ctacgatatt agtttcaagc     60
acaggtaatt tagaggtgat tcaggcagaa gttaaacagg agaaccggtt attaaatgaa    120
tcagaatcaa gttcccaggg gttactagga tactatttta gtgatttgaa ttttcaagca    180
cccatggtgg ttacctcttc tactacaggg gatttatcta ttcctagttc tgagttagaa    240
aatattccat cggaaaacca atattttcaa tctgctattt ggtcaggatt tatcaaagtt    300
aagaagagtg atgaatatac atttgctact tccgctgata atcatgtaac aatgtgggta    360
```

```
gatgaccaag aagtgattaa taaagcttct aattctaaca aaatcagatt agaaaaagga    420
agattatatc aaataaaaat tcaatatcaa cgagaaaatc ctactgaaaa aggattggat    480
ttcaagttgt actggaccga ttctcaaaat aaaaagaag tgatttctag tgataactta     540
caattgccag aattaaaaca aaaatcttcg aattcattca cgtttagatc ggcgcgtcta    600
ggacctacgg ttccagaccg tgacaatgat ggaatccctg attcattaga ggtagaagga    660
tatacggttg atgtcaaaaa taaagaact tttctttcac catggatttc taatattcat     720
gaaaagaaag gattaaccaa atataaatca tctcctgaaa aatggagcac ggcttctgat    780
ccgtacagtg atttcgaaaa ggttacagga cggattgata agaatgtatc accagaggca    840
agacaccccc ttgtggcagc ttatccgatt gtacatgtag atatggagaa tattattctc    900
tcaaaaaatg aggatcaatc cacacagaat actgatagtc aaacgagaac aataagtaaa    960
aatacttcta caagtaggac acatactagt gaagtacatg gaaatgcaga agtgcatgcg    1020
tcgttctttg atattggtgg gagtgtatct gcaggattta gtaattcgaa ttcaagtacg    1080
gtcgcaattg atcattcact atctctagca ggggaaagaa cttgggctga acaatgggt    1140 ttaaataccg ctgatacagc aagattaaat gccaatatta gatatgtaaa tactgggacg    1200
gctccaatct acaacgtgtt accaacgact tcgttagtgt taggaaaaaa tcaaacactc    1260
gcgacaatta aagctaagga aaaccaatta agtcaaatac ttgcacctaa taattattat    1320
ccttctaaaa acttggcgcc aatcgcatta aatgcacaag acgatttcag ttctactcca    1380
attacaatga attacaatca atttcttgag ttagaaaaaa cgaaacaatt aagattagat    1440
acggatcaag tatatgggaa tatagcaaca tacaattttg aaaatggaag agtgagggtg    1500
gatacaggct cgaactggag tgaagtgtta ccgcaaattc aagaaacaac tgcacgtatc    1560
atttttaatg gaaaagattt aaatctggta gaaaggcgga tagcggcggt taatcctagt    1620
gatccattag aaacgactaa accggatatg acattaaaag aagcccttaa aatagcattt    1680
ggatttaacg aaccgaatgg aaacttacaa tatcaaggga aagacataac cgaatttgat    1740
tttaatttcg atcaacaaac atctcaaaat atcaagaatc agttagcgga attaaacgca    1800
actaacatat atactgtatt agataaaatc aaattaaatg caaaaatgaa tattttaata    1860
agagataaac gttttcatta tgatagaaat aacatagcag ttggggcgga tgagtcagta    1920
gttaaggagg ctcatagaga agtaattaat tcgtcaacag agggattatt gttaaatatt    1980
gataaggata taagaaaaat attatcaggt tatattgtag aaattgaaga tactgaaggg    2040
cttaaagaag ttataaatga cagatatgat atgttgaata tttctagttt acggcaagat    2100
ggaaaaacat ttatagattt taaaaaatat aatgataaat taccgttata tataagtaat    2160
cccaattata aggtaaatgt atatgctgtt actaaagaaa acactattat taatcctagt    2220
gagaatgggg atactagtac caacgggatc aagaaaattt taatctttc taaaaaaggc    2280 tatgagatag gataa                                                   2295
```

<210> SEQ ID NO 56
<211> LENGTH: 8
<212> TYPE: PRT
<213> ORGANISM: Bacillus anthracis

<400> SEQUENCE: 56

Arg Lys Lys Arg Ser Thr Ser Ala
1               5

<210> SEQ ID NO 57

```
<211> LENGTH: 31
<212> TYPE: DNA
<213> ORGANISM: Artificial Sequence
<220> FEATURE:
<223> OTHER INFORMATION: PrAg-PCIS 'A' forward primer

<400> SEQUENCE: 57
gctgctagat cggcgcgtct aggacctacg g                           31

<210> SEQ ID NO 58
<211> LENGTH: 31
<212> TYPE: DNA
<213> ORGANISM: Artificial Sequence
<220> FEATURE:
<223> OTHER INFORMATION: PrAg-PCIS 'A' reverse primer

<400> SEQUENCE: 58
ccgtaggtcc tagacgcgcc gatctagcag c                           31

<210> SEQ ID NO 59
<211> LENGTH: 37
<212> TYPE: DNA
<213> ORGANISM: Artificial Sequence
<220> FEATURE:
<223> OTHER INFORMATION: PrAg-PCIS 'B' forward primer

<400> SEQUENCE: 59
cttcgaattc attcacgttt agatcggcgc gtctagg                     37

<210> SEQ ID NO 60
<211> LENGTH: 37
<212> TYPE: DNA
<213> ORGANISM: Artificial Sequence
<220> FEATURE:
<223> OTHER INFORMATION: PrAg-PCIS 'B' reverse primer

<400> SEQUENCE: 60
cctagacgcg ccgatctaaa cgtgaatgaa ttcgaag                     37

<210> SEQ ID NO 61
<211> LENGTH: 28
<212> TYPE: DNA
<213> ORGANISM: Artificial Sequence
<220> FEATURE:
<223> OTHER INFORMATION: R41A-testisin forward primer

<400> SEQUENCE: 61
gggtcatcac gtcggcgatc gtgggtgg                               28

<210> SEQ ID NO 62
<211> LENGTH: 25
<212> TYPE: DNA
<213> ORGANISM: Artificial Sequence
<220> FEATURE:
<223> OTHER INFORMATION: R41A-testisin reverse primer

<400> SEQUENCE: 62
cctctccacc cacgatcgcc gacgt                                  25

<210> SEQ ID NO 63
<211> LENGTH: 30
<212> TYPE: DNA
<213> ORGANISM: Artificial Sequence
<220> FEATURE:
<223> OTHER INFORMATION: S238A-testisin forward primer

<400> SEQUENCE: 63
```

```
cctgcttcgg tgacgcaggc ggacccttgg                                             30
```

<210> SEQ ID NO 64
<211> LENGTH: 25
<212> TYPE: DNA
<213> ORGANISM: Artificial Sequence
<220> FEATURE:
<223> OTHER INFORMATION: S238A-testisin reverse primer

<400> SEQUENCE: 64

```
caggccaagg gtccgcctgc gtcac                                                  25
```

<210> SEQ ID NO 65
<211> LENGTH: 33
<212> TYPE: DNA
<213> ORGANISM: Artificial Sequence
<220> FEATURE:
<223> OTHER INFORMATION: S353A-testisin forward primer

<400> SEQUENCE: 65

```
gcctgccagg gcgacgcggg tggtcccttt gtg                                         33
```

<210> SEQ ID NO 66
<211> LENGTH: 33
<212> TYPE: DNA
<213> ORGANISM: Artificial Sequence
<220> FEATURE:
<223> OTHER INFORMATION: S353A-testisin reverse primer

<400> SEQUENCE: 66

```
cacaaaggga ccacccgcgt cgccctggca ggc                                         33
```

<210> SEQ ID NO 67
<211> LENGTH: 9031
<212> TYPE: DNA
<213> ORGANISM: Artificial Sequence
<220> FEATURE:
<223> OTHER INFORMATION: Plasmid pYS5-PA33

<400> SEQUENCE: 67

```
caggagaaca aaaacgattt tttgaggaaa gttataaatt attttccgaa cgatatggca            60
agcaaaatat tgcttatgca acagttcata atgatgagca aacccctcac atgcatttag           120
gtgttgtgcc tatgcgtgat ggaaaactgc aaggaaaaaa tgtgtttaat cgtcaagaac           180
tgttatggct acaagataaa ttccccgagc atatgaaaaa cagggttttt gagttgaagc           240
gtggtgaacg tggctctgac cgtaaacata ttgagacagc taaatttaaa aaacaaactt           300
tggaaaaaga gattgatttt ctagaaaaaa atttagcagt taaaaaagat gaatggactg           360
cttatagcga taaagttaaa tcagatttag aagtaccagc gaaacgacac atgaaaagtg           420
ttgaagtgcc aacgggtgaa aagtccatgt ttggtttggg aaaagaaata atgaaaacag           480
aaaagaaacc aaccaaaaat gttgttatat cggagcgtga ttataaaaac ttagtgactg           540
ctgcgagaga taacgatagg ttaaaacagc atgttagaaa tctcatgagt actgatatgg           600
cgagagaata taaaaaatta agtaaagaac atgggcaagt aaagaaaaaa tatagtggtc           660
ttgtagagcg atttaatgaa aatgtaaatg attataatga gttgcttgaa gaaaacaagt           720
ctttaaagtc taaaataagc gatttaaagc gtgatgtgag tttaatctat gaaagcacta           780
aggaattcct taaggaacgt acagacggct aaaagccttt aaaaacgttt taaggggt            840
ttgtagacaa ggtaaaggat aaaacagcac aattccaaga aaaacacgat ttagaaccta           900
```

```
aaaagaacga atttgaacta actcataacc gagaggtaaa aaaagaacga agtcgagatc      960
agggaatgag tttataaaat aaaaaaagca cctgaaaagg tgtctttttt tgatggtttt     1020
gaacttgttc tttcttatct tgatacatat agaaataacg tcatttttat tttagttgct     1080
gaaaggtgcg ttgaagtgtt ggtatgtatg tgttttaaag tattgaaaac ccttaaaatt     1140
ggttgcacag aaaaacccca tctgttaaag ttataagtga ctaaacaaat aactaaatag     1200
atggggttt cttttaatat tatgtgtcct aatagtagca tttattcaga tgaaaaatca     1260
agggttttag tggacaagac aaaaagtgga aaagtgagac catggagaga aaagaaaatc     1320
gctaatgttg attactttga acttctgcat attcttgaat ttaaaaaggc tgaaagagta     1380
aaagattgtg ctgaaatatt agagtataaa caaaatcgtg aaacaggcga agaaagttg      1440
tatcgagtgt ggttttgtaa atccaggctt tgtccaatgt gcaactggag gagagcaatg     1500
aaacatggca ttcagtcaca aaaggttgtt gctgaagtta ttaaacaaaa gccaacagtt     1560
cgttggttgt ttctcacatt aacagttaaa aatgtttatg atggcgaaga attaaataag     1620
agtttgtcag atatggctca aggatttcgc cgaatgatgc aatataaaaa aattaataaa     1680
aatcttgttg gttttatgcg tgcaacggaa gtgacaataa ataataaaga taattcttat     1740
aatcagcaca tgcatgtatt ggtatgtgtg aaccaactt attttaagaa tacagaaaac      1800
tacgtgaatc aaaaacaatg gattcaattt tggaaaaagg caatgaaatt agactatgat     1860
ccaaatgtaa aagttcaaat gattcgaccg aaaaataaat ataaatcgga tatacaatcg     1920
gcaattgacg aaactgcaaa atatcctgta aaggatacgg attttatgac cgatgatgaa     1980
gaaaagaatt tgaacgttt gtctgatttg gaggaaggtt tacaccgtaa aaggttaatc      2040
tcctatggtg gtttgttaaa agaaatacat aaaaaaatta accttgatga cacagaagaa     2100
ggcgatttga ttcatacaga tgatgacgaa aaagccgatg aagatggatt ttctattatt     2160
gcaatgtgga attgggaacg gaaaaattat tttattaaag agtagttcaa caaacgggcc     2220
agtttgttga agattagatg ctataattgt tattaaaagg attgaaggat gcttaggaag     2280
acgagttatt aatagctgaa taagaacggt gctctccaaa tattcttatt tagaaaagca     2340
aatctaaaat tatctgaaaa gggaatgaga atagtgaatg gaccaataat aatgactaga     2400
gaagaaagaa tgaagattgt tcatgaaatt aaggaacgaa tattggataa atatggggat     2460
gatgttaagg ctattggtgt ttatggctct cttggtcgtc agactgatgg gcccttattcg    2520
gatattgaga tgatgtgtgt catgtcaaca gaggaagcag agttcagcca tgaatggaca     2580
accggtgagt ggaaggtgga agtgaatttt gatagcgaag agattctact agattatgca     2640
tctcaggtgg aatcagattg gccgcttaca catggtcaat ttttctctat tttgccgatt     2700
tatgattcag gtggatactt agagaaagtg tatcaaactg ctaaatcggt agaagcccaa     2760
acgttccacg atgcgatttg tgcccttatc gtagaagagc tgtttgaata tgcaggcaaa     2820
tggcgtaata ttcgtgtgca aggaccgaca acatttctac catccttgac tgtacaggta     2880
gcaatggcag gtgccatgtt gattggtctg catcatcgca tctgttatac gacgagcgct     2940
tcggtcttaa ctgaagcagt taagcaatca gatcttcctt caggttatga ccatctgtgc     3000
cagttcgtaa tgtctggtca actttccgac tctgagaaac ttctggaatc gctagagaat     3060
ttctggaatg ggattcagga gtggacagaa cgacacggat atatagtgga tgtgtcaaaa     3120
cgcataccat tttgaacgat gacctctaat aattgttaat catgttggtt acgtatttat     3180
taacttctcc tagtattagt aattatcatg gctgtcatgg cgcattaacg gaataaaggg     3240
tgtgcttaaa tcgggccatt ttgcgtaata agaaaaagga ttaattatga gcgaattgaa     3300
```

```
ttaataataa ggtaatagat ttacattaga aaatgaaagg ggattttatg cgtgagaatg    3360
ttacagtcta tcccggcatt gccagtcggg gatattaaaa agagtatagg tttttattgc    3420
gataaactag gtttcacttt ggttcaccat gaagatggat tcgcagttct aatgtgtaat    3480
gaggttcgga ttcatcctat taaacatata aattctttt tatgttatat atttataaaa    3540
gttctgttta aaaagccaaa aataaataat tatctctttt tatttatatt atattgaaac    3600
taaagtttat taatttcaat ataatataaa tttaatttta tacaaaaagg agaacgtata    3660 tgaaaaacg aaaagtgtta ataccattaa tggcattgtc tacgatatta gtttcaagca    3720
caggtaattt agaggtgatt caggcagaag ttaaacagga gaaccggtta ttaaatgaat    3780
cagaatcaag ttcccagggg ttactaggat actattttag tgatttgaat tttcaagcac    3840
ccatggtggt tacctcttct actacagggg atttatctat tcctagttct gagttagaaa    3900
atattccatc ggaaaaccaa tattttcaat ctgctatttg gtcaggattt atcaaagtta    3960
agaagagtga tgaatataca tttgctactt ccgctgataa tcatgtaaca atgtgggtag    4020
atgaccaaga agtgattaat aaagcttcta attctaacaa aatcagatta gaaaaaggaa    4080
gattatatca aataaaaatt caatatcaac gagaaaatcc tactgaaaaa ggattggatt    4140
tcaagttgta ctggaccgat tctcaaaata aaaagaagt gatttctagt gataacttac    4200
aattgccaga attaaaacaa aaatcttcga attcaagagc tgctagatcg acgtctgcag    4260
gacctacggt tccagaccgt gacaatgatg gaatccctga ttcattagag gtagaaggat    4320
atacggttga tgtcaaaaat aaaagaactt ttctttcacc atggatttct aatattcatg    4380
aaaagaaagg attaaccaaa tataaatcat ctcctgaaaa atggagcacg gcttctgatc    4440
cgtacagtga tttcgaaaag gttacaggac ggattgataa gaatgtatca ccagaggcaa    4500 gacacccct tgtggcagct tatccgattg tacatgtaga tatggagaat attattctct    4560
caaaaaatga ggatcaatcc acacagaata ctgatagtca aacgagaaca ataagtaaaa    4620
atacttctac aagtaggaca catactagtg aagtacatgg aaatgcagaa gtgcatgcgt    4680
cgttctttga tattggtggg agtgtatctg caggatttag taattcgaat tcaagtacgg    4740
tcgcaattga tcattcacta tctctagcag gggaaagaac ttgggctgaa acaatgggtt    4800
taaataccgc tgatacagca agattaaatg ccaatattag atatgtaaat actgggacgg    4860
ctccaatcta caacgtgtta ccaacgactt cgttagtgtt aggaaaaaat caaacactcg    4920
cgacaattaa agctaaggaa aaccaattaa gtcaaatact tgcacctaat aattattatc    4980
cttctaaaaa cttggcgcca atcgcattaa atgcacaaga cgatttcagt tctactccaa    5040
ttacaatgaa ttacaatcaa tttcttgagt tagaaaaaac gaaacaatta agattagata    5100
cggatcaagt atatgggaat atagcaacat acaattttga aaatgaaga gtgagggtgg    5160 atacaggctc gaactggagt gaagtgttac cgcaaattca agaaacaact gcacgtatca    5220
tttttaatgg aaaagattta aatctggtag aaaggcggat agcggcggtt aatcctagtg    5280
atccattaga aacgactaaa ccggatatga cattaaaaga agcccttaaa atagcatttg    5340
gatttaacga accgaatgga aacttacaat atcaagggaa agacataacc gaatttgatt    5400
ttaatttcga tcaacaaaca tctcaaaata tcaagaatca gttagcggaa ttaaacgcaa    5460
ctaacatata tactgtatta gataaaatca aattaaatgc aaaaatgaat attttaataa    5520
gagataaacg ttttcattat gatagaaata acatagcagt tggggcggat gagtcagtag    5580
ttaaggaggc tcatagagaa gtaattaatt cgtcaacaga gggattattg ttaaatattg    5640
```

```
ataaggatat aagaaaaata ttatcaggtt atattgtaga aattgaagat actgaagggc    5700
ttaaagaagt tataaatgac agatatgata tgttgaatat ttctagttta cggcaagatg    5760
gaaaaacatt tatagatttt aaaaaatata atgataaatt accgttatat ataagtaatc    5820
ccaattataa ggtaaatgta tatgctgtta ctaaagaaaa cactattatt aatcctagtg    5880
agaatgggga tactagtacc aacgggatca agaaaatttt aatcttttct aaaaaaggct    5940
atgagatagg ataaggtaat tctaggtgat ttttaaatta tctaaaaaac agtaaaatta    6000
aaacatactc ttttttgtaag aaatacaagg agagtatgtt ttaaacagta atctaaatca    6060
tcataatcct ttgagattgt ttgtaggatc ccgggtaaga attcggctgc taacaaagcc    6120
cgaaaggaag ctgagttggc tgctgccacc gctgagcaat aactagcata accccttggg    6180
gcctctaaac gggtcttgag gggttttttg ctgaaaggag gaactatatc cggatcggag    6240
atcaattctg gcgtaatagc gaagaggccc gcaccgatcg cccttcccaa cagttgcgta    6300
gcctgaatgg cgaatgggac gcgccctgta gcggcgcatt aagcgcggcg ggtgtggtgg    6360
ttacgcgcag cgtgaccgct acacttgcca gcgccctagc gcccgctcct ttcgctttct    6420
tcccttcctt tctcgccacg ttcgccggct ttccccgtca gctctaaat cggggggctcc    6480 ctttagggtt ccgatttagt gctttacggc acctcgaccc caaaaaactt gattagggtg    6540
atggttcacg tagtgggcca tcgccctgat agacggtttt tcgccctttg acgttggagt    6600
ccacgttctt aatagtgga ctcttgttcc aaactgaac aacactcaac cctatctcgg    6660
tctattcttt tgatttataa gggattttgc cgatttcggc ctattggtta aaaaatgagc    6720
tgatttaaca aaaatttaac gcgaatttta acaaaatatt aacgtttaca atttcaggtg    6780
gcacttttcg gggaaatgtg cgcggaaccc ctatttgttt attttctaa atacattcaa    6840 atatgtatcc gctcatgaga caataaccct gataaatgct tcaataatat tgaaaaagga    6900
agagtatgag tattcaacat ttccgtgtcg cccttattcc cttttttgcg cattttgcc    6960 ttcctgttttt tgctcaccca gaaacgctgg tgaaagtaaa agatgctgaa gatcagttgg    7020
gtgcacgagt gggttacatc gaactggatc tcaacagcgg taagatcctt gagagttttc    7080
gccccgaaga acgttttcca atgatgagca cttttaaagt tctgctatgt ggcgcggtat    7140
tatcccgtat tgacgccggg caagagcaac tcggtcgccg catacactat tctcagaatg    7200
acttggttga gtactcacca gtcacagaaa agcatcttac ggatggcatg acagtaagag    7260
aattatgcag tgctgccata agcatgagtg ataacactgc ggccaactta cttctgacaa    7320
cgatcggagg accgaaggag ctaaccgctt ttttcacaa catgggggat catgtaactc    7380
gccttgatcg ttgggaaccg gagctgaatg aagccatacc aaacgacgag cgtgacacca    7440
cgatgcctgt agcaatggca acaacgttgc gcaaactatt aactggcgaa ctacttactc    7500
tagcttcccg gcaacaatta atagactgga tgaggcgga taaagttgca ggaccacttc    7560
tgcgctcggc ccttccggct ggctggttta ttgctgataa atctggagcc ggtgagcgtg    7620
ggtctcgcgg tatcattgca gcactggggc cagatggtaa gccctcccgt atcgtagtta    7680
tctacacgac gggcagtcag gcaactatgg atgaacgaaa tagacagatc gctgagatag    7740
gtgcctcact gattaagcat tggtaactgt cagaccaagt ttactcatat atactttaga    7800
ttgatttaaa acttcatttt taatttaaaa ggatctaggt gaagatcctt tttgataatc    7860
tcatgaccaa aatcccttaa cgtgagtttt cgttccactg agcgtcagac cccgtagaaa    7920
agatcaaagg atcttcttga gatcctttt ttctgcgcgt aatctgctgc ttgcaaacaa    7980
aaaaaccacc gctaccagcg gtggtttgtt tgccggatca agagctacca actctttttc    8040
```

```
cgaaggtaac tggcttcagc agagcgcaga taccaaatac tgtccttcta gtgtagccgt    8100
agttaggcca ccacttcaag aactctgtag caccgcctac atacctcgct ctgctaatcc    8160
tgttaccagt ggctgctgcc agtggcgata agtcgtgtct taccgggttg gactcaagac    8220
gatagttacc ggataaggcg cagcggtcgg gctgaacggg gggttcgtgc acacagccca    8280
gcttggagcg aacgacctac accgaactga gatacctaca gcgtgagcat tgagaaagcg    8340
ccacgcttcc cgaagggaga aaggcggaca ggtatccggt aagcggcagg gtcggaacag    8400
gagagcgcac gagggagctt ccagggggga acgcctggta tctttatagt cctgtcgggt    8460
ttcgccacct ctgacttgag cgtcgatttt tgtgatgctc gtcaggggg ccgagcctat    8520 ggaaaaacgc cagcaacgcg gccttttac ggttcctggc cttttgctgg cctttgctc     8580 acatgttctt tcctgcgtta tcccctgatt ctgtggataa ccgtattacc gcctttgagt    8640
gagctgatac cgctcgccgc agccgaacga ccgagcgcag cgagtcagtg agcgaggaag    8700
cggaagagcg cctgatgcgg tattttctcc ttacgcatct gtgcggtatt tcacaccgca    8760
tatatggtgc actctcagta caatctgctc tgatgccgca tagttaagcc agtatacact    8820
ccgctatcgc tacgtgactg caaggagatg gcgcccaaca gtcccccggc cacggggcct    8880
gccaccatac ccacgccgaa acaagcgctc atgagcccga agtggcgagc ccgatcttcc    8940
ccatcggtga tgtcggcgat ataggcgcca gcaaccgcac ctgtggcgcc ggtgatgccg    9000
gccacgatgc gtccggcgta gaggatcttg a                                   9031
```